US012729198B2

(12) United States Patent
Wang et al.

(10) Patent No.: US 12,729,198 B2
(45) **Date of Patent: *Sep. 8, 2026**

(54) AMIDE OXAZOLE COMPOUND

(71) Applicant: SHANGHAI FOSUN PHARMACEUTICAL INDUSTRIAL DEVELOPMENT CO., LTD., Shanghai (CN)

(72) Inventors: Jianfei Wang, Shanghai (CN); Haizhong Tan, Shanghai (CN); Yang Zhang, Shanghai (CN); Jian Li, Shanghai (CN); Shuhui Chen, Shanghai (CN)

(73) Assignee: Shanghai Fosun Pharmaceutical Industrial Development Co., Ltd., Shanghai (CN)

( * ) Notice: Subject to any disclaimer, the term of this patent is extended or adjusted under 35 U.S.C. 154(b) by 544 days.

This patent is subject to a terminal disclaimer.

(21) Appl. No.: 18/269,065

(22) PCT Filed: Dec. 20, 2021

(86) PCT No.: PCT/CN2021/139649
§ 371 (c)(1),
(2) Date: Jun. 22, 2023

(87) PCT Pub. No.: WO2022/135338
PCT Pub. Date: Jun. 30, 2022

(65) Prior Publication Data

US 2023/0391776 A1 Dec. 7, 2023

(30) Foreign Application Priority Data

Dec. 25, 2020 (CN) ......................... 202011568684.7
Jul. 1, 2021 (CN) ......................... 202110749304.8
Aug. 13, 2021 (CN) ......................... 202110930084.9
Sep. 30, 2021 (CN) ......................... 202111165942.1

(51) Int. Cl.
*C07D 471/04* (2006.01)
*A61P 35/00* (2006.01)
*C07D 487/04* (2006.01)
*C07D 519/00* (2006.01)

(52) U.S. Cl.
CPC ............ *C07D 471/04* (2013.01); *A61P 35/00* (2018.01); *C07D 487/04* (2013.01); *C07D 519/00* (2013.01)

(58) Field of Classification Search
None
See application file for complete search history.

(56) References Cited

U.S. PATENT DOCUMENTS 10,047,104 B2 8/2018 Gummadi et al.
10,160,753 B2 12/2018 Gummadi et al.
10,899,772 B2 1/2021 Bryan et al.
11,419,875 B2 8/2022 Gummadi et al.
2017/0035881 A1 2/2017 Lannutti et al.
2017/0152263 A1 6/2017 Gummadi et al.
2018/0201609 A1 7/2018 Gummadi et al.
2018/0208605 A1 7/2018 Gummadi et al.
2021/0376688 A1 12/2021 Blessing et al.
2022/0267322 A1 8/2022 Wang et al.

FOREIGN PATENT DOCUMENTS

CN 102137592 A 7/2011
CN 106456609 A 2/2017
CN 106456619 A 2/2017
CN 106458982 A 2/2017
CN 108024971 A 5/2018
CN 108026065 A 5/2018
CN 110691589 A 1/2020
CN 110785418 A 2/2020
CN 110835338 A 2/2020
CN 114072401 A 2/2022
JP 2017502088 A 1/2017
JP 2017505337 A 2/2017
JP 2017518348 A 7/2017
JP 2018524365 A 8/2018
JP 2018524372 A 8/2018
JP 2020512343 A 4/2020
JP 2020524663 A 8/2020
(Continued)

OTHER PUBLICATIONS

Jul. 2, 2024 First Action issued in Japan Patent Application No. JP2023538960.
Office Action issued in corresponding Chinese Patent Application No. 202180086314.6, dated Jul. 10, 2025.
Gummadi, et al.; "Discovery of CA-4948, an Orally Bioavailable IRAK4 Inhibitor for Treatment of Hematologic Malignancies", Oct. 14, 2020.
(Continued)

*Primary Examiner* — Sarah Pihonak
*Assistant Examiner* — Donna M Nestor
(74) *Attorney, Agent, or Firm* — Morgan, Lewis & Bockius LLP

(57) ABSTRACT

Provided is an amide oxazole compound, in particular a compound, as represented by formula (IV), or a pharmaceutically acceptable salt thereof.

(IV)

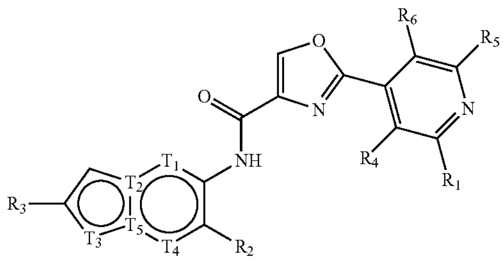

4 Claims, 2 Drawing Sheets

(56) References Cited

FOREIGN PATENT DOCUMENTS

| | | | |
|---|---|---|---|
| JP | 2022500996 | A | 1/2022 |
| JP | 7340680 | B2 | 9/2023 |
| WO | 2005/016928 | A1 | 2/2005 |
| WO | 2015104662 | A1 | 7/2015 |
| WO | 2015104688 | A1 | 7/2015 |
| WO | 2015193846 | A1 | 12/2015 |
| WO | 2017009798 | A1 | 1/2017 |
| WO | 2017009806 | A1 | 1/2017 |
| WO | 2018178947 | A2 | 10/2018 |
| WO | 2018234342 | A1 | 12/2018 |
| WO | 2019089580 | A1 | 5/2019 |
| WO | 2020035020 | A1 | 2/2020 |
| WO | 2020150626 | A1 | 7/2020 |
| WO | 2021004533 | A1 | 1/2021 |

OTHER PUBLICATIONS

International Search Report issued on Mar. 15, 2022 for International application No. PCT/CN2021/139649 with English translation.

Written Opinion of the International Searching Authority issued on Mar. 15, 2022 for International application No. PCT/CN2021/139649 with English translation.

Nov. 13, 2024 Extended European Search Report issued in European Patent Application No. 21909334.1.

Wang et al., "IRAK-4 Inhibitors for Inflammation", Current Topics in Medicinal Chemistry, vol. 9, No. 8, 2009, pp. 724-737.

International Search Report issued in International Application No. PCT/CN2020/101369, dated Oct. 12, 2020.

Office Action issued in corresponding Japanese Patent Application No. 2022-500996, dated Mar. 14, 2023.

Action issued in corresponding Chinese Patent Application No. 202180086314.6, dated Jan. 29, 2026.

Note: PO stands for oral administration, QD stands for once a day and BID stands for twice a day.

AMIDE OXAZOLE COMPOUND

This is a National Phase Application filed under 35 U.S.C. 371 as a national stage of PCT/CN2021/139649, filed Dec. 20, 2021, an application claiming the benefit of Chinese Application No. 202011568684.7, filed Dec. 25, 2020, Chinese Application No. 202110749304.8, filed Jul. 1, 2021, Chinese Application No. 202110930084.9, filed Aug. 13, 2021, and Chinese Application No. 202111165942.1, filed Sep. 30, 2021, the content of each of which is hereby incorporated by reference in its entirety.

TECHNICAL FIELD

The present disclosure relates to a class of amide oxazole compounds, specifically a compound shown in formula (IV) or a pharmaceutically acceptable salt thereof.

BACKGROUND

Interleukin-1 receptor-associated kinase 4 (IRAK4) is a serine/threonine-specific protein kinase, a member of the tyrosine like kinase (TLK) family, and a key node in the innate immune response involving interleukin-1, 18, 33 receptors and Toll-like receptors. Extracellular signal molecules bind with interleukin receptor or Toll-like receptor to form MyD88: IRAK4: IRAK1/2 multiprotein complex, leading to phosphorylation of IRAK1/2 and mediating a series of downstream signal transduction, thus activating p38, JNK and NF-κB signaling pathways, and finally leading to the expression of proinflammatory cytokines. Clinicopathological studies have shown that individuals with IRAK4 mutation have a protective effect on chronic lung disease and inflammatory bowel disease. IRAK4 deficiency itself is not lethal, and individuals can survive until adulthood with a reduced risk of infection with age. Therefore, IRAK4 has become an important therapeutic target for the treatment of inflammatory diseases, immune diseases, tumor diseases and many other diseases. As shown in the following figures, BAY-1 and BAY-2 are small molecule IRAK4 inhibitors developed by Bayer Company, and clinical research on immune and tumor diseases has been carried out.

BAY-1

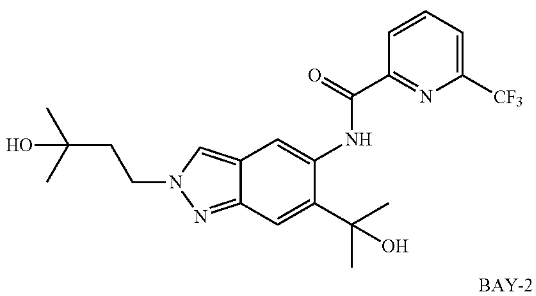

BAY-2

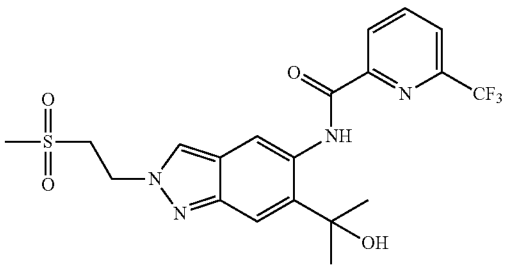

Activated B-cell-like diffuse large B-cell lymphoma (ABC-DLBCL) is a highly invasive and poorly prognostic DLBCL, which is usually characterized by abnormalities of B-cell receptor (BCR) pathway and myeloid-like differentiation factor 88 (MyD88) pathway, which further leads to the continuous activation of nuclear factor KB protein (NF-κB) signaling pathway. CD79 mutation is a common abnormal mutation in BCR pathway, and BTK inhibitors such as Ibrutinib can inhibit the abnormal activation of NF-κB signaling pathway caused by CD79 mutation, thus inhibiting the proliferation of ABC-DLBCL cells. The abnormality of MyD88 pathway is mainly caused by $MyD88^{L265P}$ site mutations, which accounts for about 30%, IRAK4 inhibitors can effectively block the abnormally activated MyD88 signaling pathway and further block the abnormal activation of the NF-κB pathway. However, ABC-DLBCL patients with $MyD88^{L265P}$ mutations have a poor response to BCR inhibitors due to abnormal MyD88 signaling pathway, and a large number of research data from Bayer, Nimbus and AstraZeneca indicate that the combination of IRAK4 inhibitor and BTK inhibitor can significantly improve the in vivo efficacy of Ibrutinib in ABC-DLBCL xenotransplantation animal model. If the abnormalities of BCR pathway and MyD88 pathway can be effectively inhibited at the same time, it will be a more effective way to treat ABC-DLBCL, therefore, developing RAK4 and BTK dual-target inhibitors can obtain double benefits in blocking NF-κB pathway, which is a very efficient and effective strategy in terms of therapeutic mechanism and provides a potentially effective new therapeutic method for ABC-DLBCL patients.

CONTENT OF THE PRESENT INVENTION

The present disclosure provides a compound represented by formula (IV) or a pharmaceutically acceptable salt thereof, (IV)

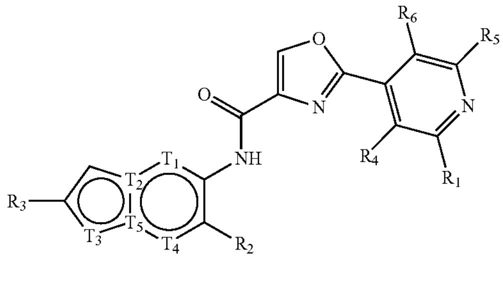

wherein, $T_1$, $T_2$, $T_3$, $T_4$ and $T_5$ are independently selected from CH and N;

the structural unit

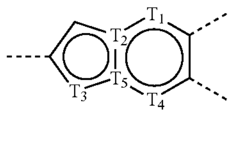

is selected from

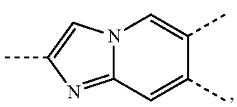

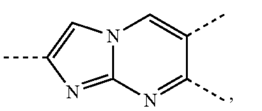

and

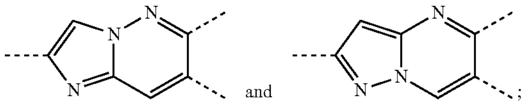

$R_1$ is selected from H, F, Cl, Br, I, OH, CN, $NR_aR_b$, $CH_3$, —C(═O)—$C_{1-3}$ alkyl and $C_{1-3}$ alkoxy, and the $C_{1-3}$ alkyl and $C_{1-3}$ alkoxy are independently and optionally substituted with 1, 2 or 3 halogens;

$R_4$ is selected from H, F, Cl, Br, I, OH, CN, $NR_aR_b$, $C_{1-3}$ alkyl and —C(═O)—$C_{1-3}$ alkyl, and the $C_{1-3}$ alkyl is optionally substituted with 1, 2 or 3 halogens;

or, $R_1$ and $R_4$ are attached to form pyrrolyl with the attached atoms;

$R_2$ is selected from

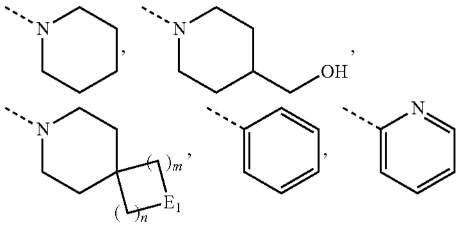

and

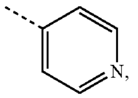

and the

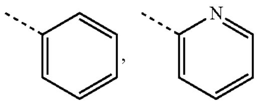

and

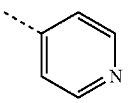

are optionally substituted with one F;

$R_3$ is selected from

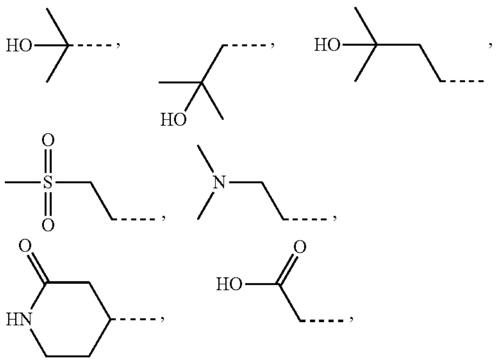

-continued

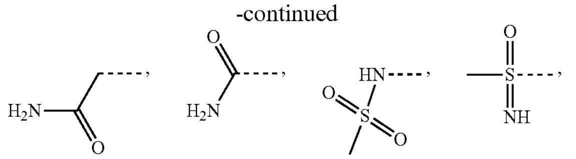

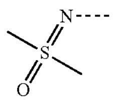

and

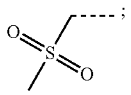

$E_1$ is selected from NH, O and S;

$R_5$ and $R_6$ are independently selected from H, F, Cl, Br, I, OH, CN, —C(═O)—$C_{1-3}$ alkyl and $C_{1-3}$ alkyl, and the $C_{1-3}$ alkyl is optionally substituted with 1, 2 or 3 halogens;

m is 1 or 2;

n is 1 or 2;

$R_a$ is independently selected from H and $C_{1-3}$ alkyl;

$R_b$ is independently selected from H, $C_{1-3}$ alkyl and —C(═O)—$C_{1-3}$ alkyl;

on condition that:

1) when the structural unit

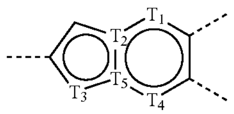

is selected from

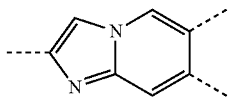

and $R_2$ is selected from

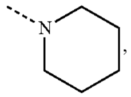

$R_1$ is selected from $NR_aR_b$ and $C_{1-3}$ alkoxy, and the $C_{1-3}$ alkoxy is optionally substituted with 1, 2 or 3 halogens, or $R_1$ and $R_4$ are attached to form pyrrolyl with the attached atoms;

2) when the structural unit

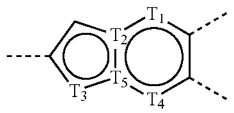

is selected from

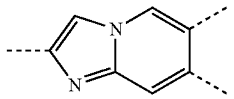

and $R_2$ is selected from

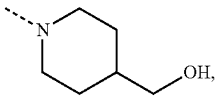

$R_3$ is selected from

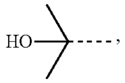
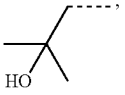
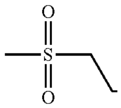
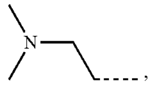
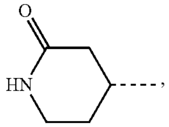
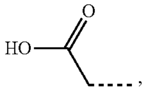
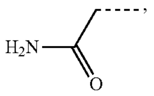
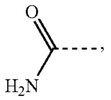
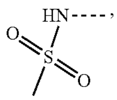
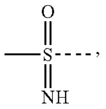
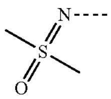
and
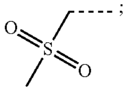

3) when the structural unit

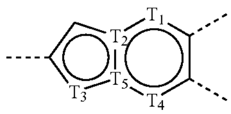

is selected from

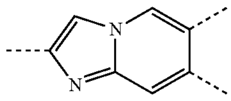

and $R_2$ is selected from

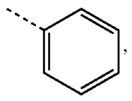

$R_3$ is selected from

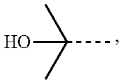
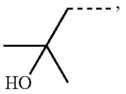
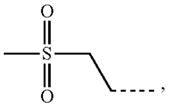
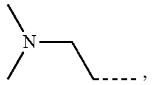
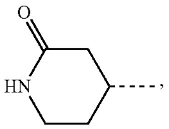
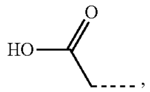
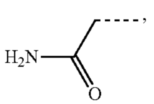
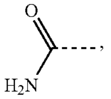
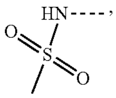
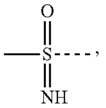
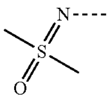
and
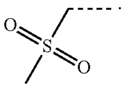

In some embodiments of the present disclosure, the $R_a$ is selected from H, $CH_3$, $CH_2CH_3$ and $CH(CH_3)_2$, and the other variables are as defined in the present disclosure.

In some embodiments of the present disclosure, the $R_b$ is selected from H, $CH_3$, $CH_2CH_3$, $CH(CH_3)_2$, $-C(=O)-CH_3$, $-C(=O)-CH_2CH_3$ and $-C(=O)-C(CH_3)_2$, and the other variables are as defined in the present disclosure.

In some embodiments of the present disclosure, the $R_1$ is selected from H, F, Cl, Br, I, OH, CN, $NR_aR_b$, $CH_3$, $-C(=O)-CH_3$ and $OCH_3$, and the $OCH_3$ is optionally substituted with 1, 2 or 3 halogens, and the other variables are as defined in the present disclosure.

In some embodiments of the present disclosure, the $R_1$ is selected from $NH_2$, $-NHCH_3$, $-N(CH_3)_2$, $-NHC(=O)CH_3$, $CH_3$ and $-OCH_3$, and the other variables are as defined in the present disclosure.

In some embodiments of the present disclosure, the $R_1$ and $R_4$ are attached to form pyrrolyl with the attached atoms, so that the structural fragment

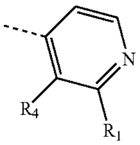

forms

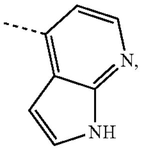

and the other variables are as defined in the present disclosure.

In some embodiments of the present disclosure, the $R_2$ is selected from

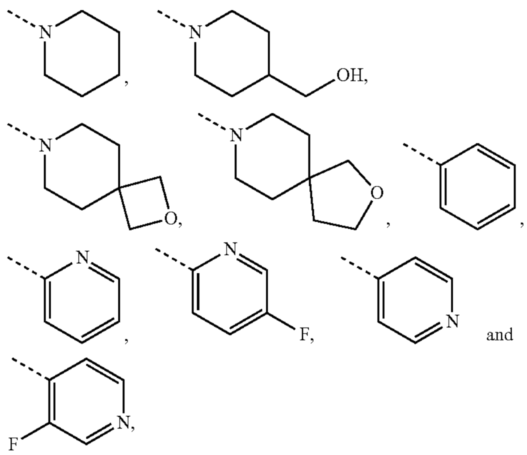

and the other variables are as defined in the present disclosure.

In some embodiments of the present disclosure, the $R_4$, $R_5$ and $R_6$ are independently selected from H, F, Cl, Br, I, OH, CN, $NH_2$, $NH(CH_3)$, $N(CH_3)_2$, $CH_3$, $CH_2CH_3$ and $CH(CH_3)_2$, and the $CH_3$, $CH_2CH_3$ and $CH(CH_3)_2$ are optionally substituted with 1, 2 or 3 F, and the other variables are as defined in the present disclosure.

In some embodiments of the present disclosure, the $R_4$, $R_5$ and $R_6$ are independently selected from H, F, Cl, Br, I, $CH_3$ and $CF_3$, and the other variables are as defined in the present disclosure.

The present disclosure provides a compound represented by formula (II) or a pharmaceutically acceptable salt thereof, (II)

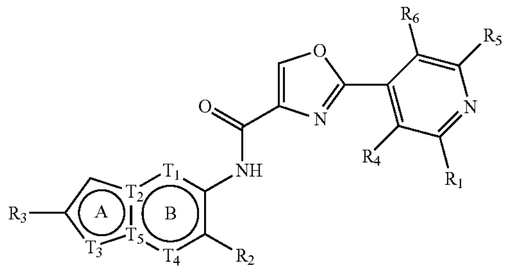

wherein, $T_1$, $T_2$, $T_3$, $T_4$ and $T_5$ are independently selected from CH and N;

the structural unit

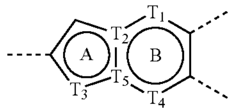

is selected from

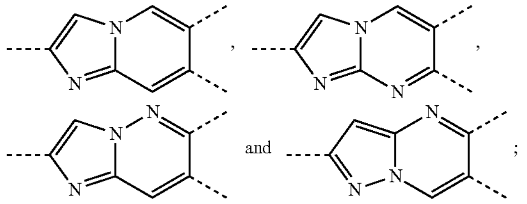

$R_1$ is selected from H, F, Cl, Br, I, OH, CN, $NR_aR_b$, $CH_3$, —C(=O)—$C_{1-3}$ alkyl and $C_{1-3}$ alkoxy, and the $C_{1-3}$ alkyl and $C_{1-3}$ alkoxy are independently and optionally substituted with 1, 2 or 3 halogens;

$R_4$ is selected from H, F, Cl, Br, I, OH, CN, $NR_aR_b$, $C_{1-3}$ alkyl and —C(=O)—$C_{1-3}$ alkyl, and the $C_{1-3}$ alkyl is optionally substituted with 1, 2 or 3 halogens;

or, $R_1$ and $R_4$ are attached to form pyrrolyl with the attached atoms;

$R_2$ is selected from

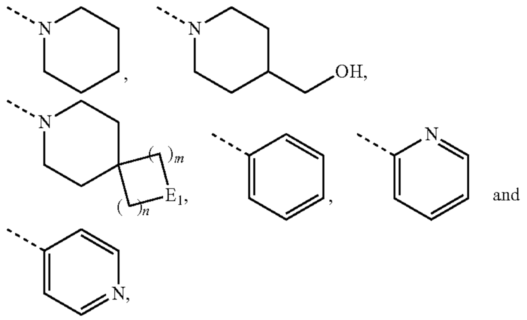

and the

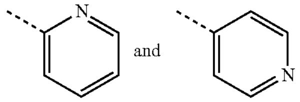

are optionally substituted with one F;

$R_3$ is selected from

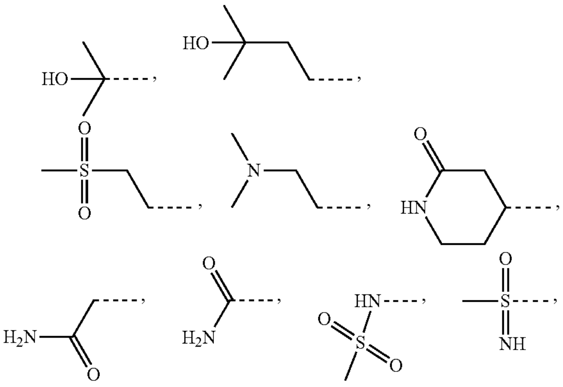

-continued

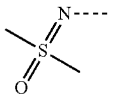 and 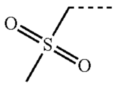;

$E_1$ is selected from NH, O and S;

$R_5$ and $R_6$ are independently selected from H, F, Cl, Br, I, OH, CN, —C(=O)—$C_{1-3}$ alkyl and $C_{1-3}$ alkyl, and the $C_{1-3}$ alkyl is optionally substituted with 1, 2 or 3 halogens;

m is 1 or 2;

n is 1 or 2;

$R_a$ is selected from H and $C_{1-3}$ alkyl;

$R_b$ is selected from H, $C_{1-3}$ alkyl and —C(O)—$C_{1-3}$ alkyl;

on condition that:

1) when the structural unit

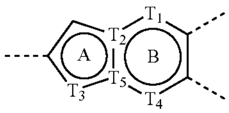

is selected from

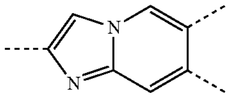

and $R_2$ is selected from

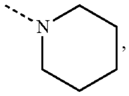, $R_1$ is selected from $NR_aR_b$ and $C_{1-3}$ alkoxy, and the $C_{1-3}$ alkoxy is optionally substituted with 1, 2 or 3 halogens, or $R_1$ and $R_4$ are attached to form pyrrolyl with the attached atoms;

2) when the structural unit

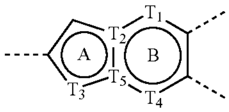

is selected from

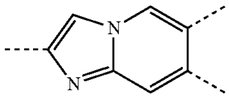

and $R_2$ is selected from

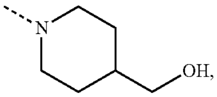, $R_3$ is selected from

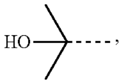, 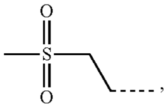, 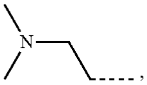, 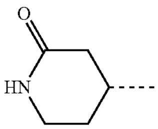, 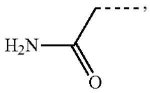, 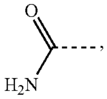, 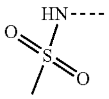, 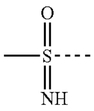, 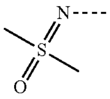 and 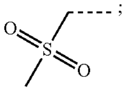;

3) when the structural unit

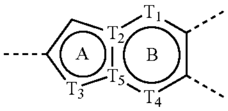

is selected from

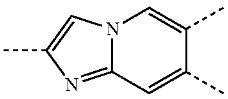

and $R_2$ is selected from

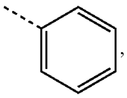, $R_3$ is selected from

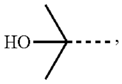, 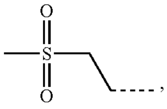,

-continued

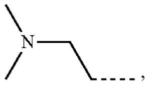, 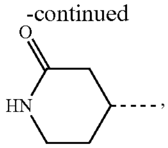, 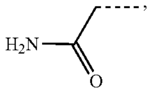, 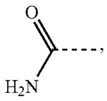, 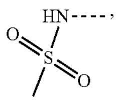, 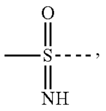, 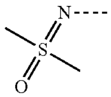 and 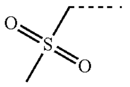.

In some embodiments of the present disclosure, the $R_a$ is selected from H, $CH_3$, $CH_2CH_3$ and $CH(CH_3)_2$, and the other variables are as defined in the present disclosure.

In some embodiments of the present disclosure, the $R_b$ is selected from H, $CH_3$, $CH_2CH_3$, $CH(CH_3)_2$, —C(O)—$CH_3$, —C(O)—$CH_2CH_3$ and —C(O)—$C(CH_3)_2$, and the other variables are as defined in the present disclosure.

In some embodiments of the present disclosure, the $R_1$ is selected from H, F, Cl, Br, I, OH, CN, $NR_aR_b$, $CH_3$, —C(=O)—$CH_3$ and $OCH_3$, and the $OCH_3$ is optionally substituted with 1, 2 or 3 $R_c$, and the other variables are as defined in the present disclosure.

In some embodiments of the present disclosure, the $R_1$ is selected from $NH_2$, —$NHCH_3$, —$N(CH_3)_2$, —NHC(O)$CH_3$, $CH_3$ and —$OCH_3$, and the other variables are as defined in the present disclosure.

In some embodiments of the present disclosure, the $R_1$ and $R_4$ are attached to form a ring with the attached atoms so that the structural fragment

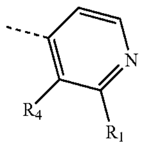

forms

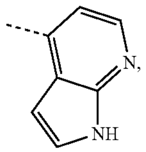

and the other variables are as defined in the present disclosure.

In some embodiments of the present disclosure, the $R_2$ is selected from

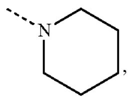, 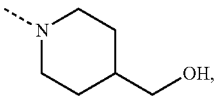

-continued

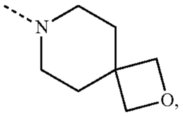 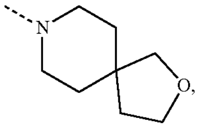 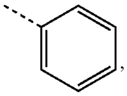, 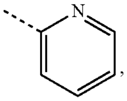, 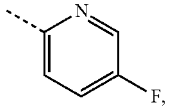 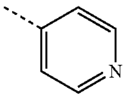 and 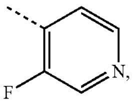

and the other variables are as defined in the present disclosure.

In some embodiments of the present disclosure, the $R_4$, $R_5$ and $R_6$ are independently selected from H, F, Cl, Br, I, OH, CN, $NH_2$, $NH(CH_3)$, $N(CH_3)_2$, $CH_3$, $CH_2CH_3$ and $CH(CH_3)_2$, and the $CH_3$, $CH_2CH_3$ and $CH(CH_3)_2$ are optionally substituted with 1, 2 or 3 F, and the other variables are as defined in the present disclosure.

In some embodiments of the present disclosure, the $R_4$, $R_5$ and $R_6$ are independently selected from H, F, Cl, Br, I, $CH_3$ and $CF_3$, and the other variables are as defined in the present disclosure.

The present disclosure provides a compound represented by formula (II) or a pharmaceutically acceptable salt thereof, (II)

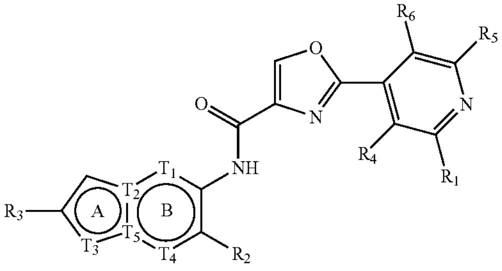

wherein, $T_1$, $T_2$, $T_3$, $T_4$ and $T_5$ are independently selected from CH and N;

the structural unit

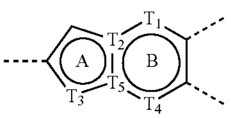

is selected from

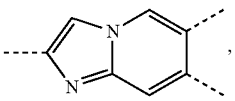, 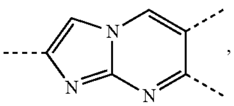,

-continued

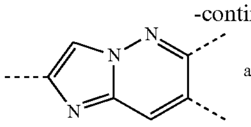 and 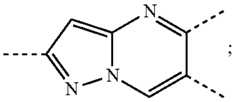 ;

$R_1$ is selected from H, F, Cl, Br, I, OH, CN, $NR_aR_b$, $CH_3$, —C(=O)—$C_{1-3}$ alkyl and $C_{1-3}$ alkoxy, and the $C_{1-3}$ alkyl and $C_{1-3}$ alkoxy are independently and optionally substituted with 1, 2 or 3 $R_c$;

$R_4$ is selected from H, F, Cl, Br, I, OH, CN, $NR_aR_b$, $C_{1-3}$ alkyl and —C(=O)—$C_{1-3}$ alkyl, and the $C_{1-3}$ alkyl is optionally substituted with 1, 2 or 3 $R_d$;

or, $R_1$ and $R_4$ are attached to form pyrrolyl with the attached atoms;

$R_2$ is selected from

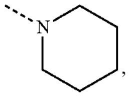 , 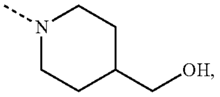

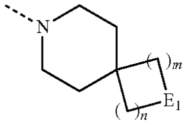 and 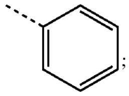 ;

$R_3$ is selected from

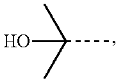 , 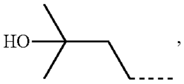 , 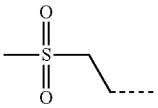 and

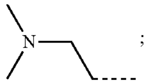 ;

$E_1$ is selected from NH, O and S;

$R_5$ and $R_6$ are independently selected from H, F, Cl, Br, I, OH, CN, —C(=O)—$C_{1-3}$ alkyl and $C_{1-3}$ alkyl, and the $C_{1-3}$ alkyl is optionally substituted with 1, 2 or 3 $R_e$;

m is selected from 1 and 2;

n is selected from 1 and 2;

$R_a$ is selected from H and $C_{1-3}$ alkyl;

$R_b$ is selected from H, $C_{1-3}$ alkyl and —C(O)—$C_{1-3}$ alkyl;

$R_c$ is selected from F, Cl, Br and I;

$R_d$ is selected from F, Cl, Br and I;

$R_e$ is selected from F, Cl, Br and I;

on condition that:

1) when the structural unit

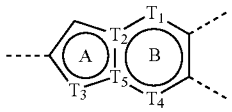

is selected from

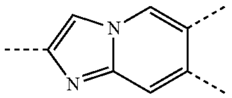

and $R_2$ is selected from

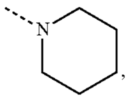 , $R_1$ is selected from $NR_aR_b$ and $C_{1-3}$ alkoxy, and the $C_{1-3}$ alkoxy is optionally substituted with 1, 2 or 3 $R_c$, or $R_1$ and $R_4$ are attached to form pyrrolyl with the attached atoms;

2) when the structural unit

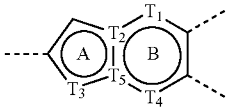

is selected from

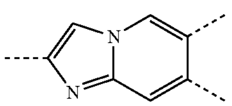

and $R_2$ is selected from

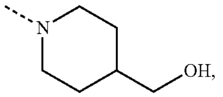

$R_3$ is selected from

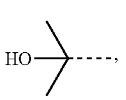 , 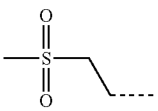 and 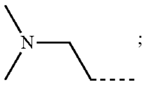 ;

3) when the structural unit

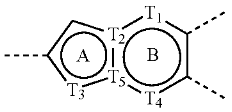

is selected from

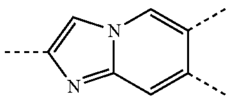

and $R_2$ is selected from

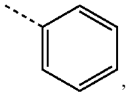, $R_3$ is selected from

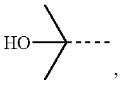, 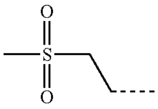 and 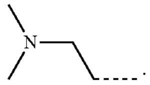.

In some embodiments of the present disclosure, the $R_a$ is selected from H, $CH_3$, $CH_2CH_3$ and $CH(CH_3)_2$, and the other variables are as defined in the present disclosure.

In some embodiments of the present disclosure, the $R_b$ is selected from H, $CH_3$, $CH_2CH_3$, $CH(CH_3)_2$, —C(O)—$CH_3$, —C(O)—$CH_2CH_3$ and —C(O)—$C(CH_3)_2$, and the other variables are as defined in the present disclosure.

In some embodiments of the present disclosure, the $R_1$ is selected from H, F, Cl, Br, I, OH, CN, $NR_aR_b$, $CH_3$, —C(═O)—$CH_3$ and $OCH_3$, and the $OCH_3$ is optionally substituted with 1, 2 or 3 $R_c$, and the other variables are as defined in the present disclosure.

In some embodiments of the present disclosure, the $R_1$ is selected from $NH_2$, —$NHCH_3$, —$N(CH_3)_2$, —NHC(O)$CH_3$ and —$OCH_3$, and the other variables are as defined in the present disclosure.

In some embodiments of the present disclosure, the $R_1$ and $R_4$ are attached to form a ring with the attached atoms so that the structural fragment

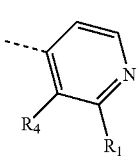

forms

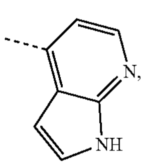

and the other variables are as defined in the present disclosure.

In some embodiments of the present disclosure, the $R_2$ is selected from

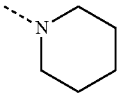, 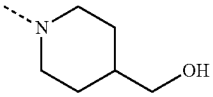, 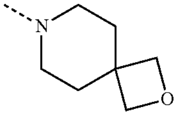, 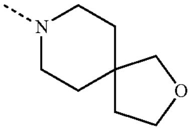 and 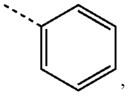, and the other variables are as defined in the present disclosure.

In some embodiments of the present disclosure, the $R_4$, $R_5$ and $R_6$ are independently selected from H, F, Cl, Br, I, OH, CN, $NH_2$, $NH(CH_3)$, $N(CH_3)_2$, $CH_3$, $CH_2CH_3$ and $CH(CH_3)_2$, and the $CH_3$, $CH_2CH_3$ and $CH(CH_3)_2$ are optionally substituted with 1, 2 or 3 F, and the other variables are as defined in the present disclosure.

In some embodiments of the present disclosure, the $R_4$, $R_5$ and $R_6$ are independently selected from H, F, Cl, Br, I, $CH_3$ and $CF_3$, and the other variables are as defined in the present disclosure.

The present disclosure provides a compound represented by formula (I) or a pharmaceutically acceptable salt thereof, (I)

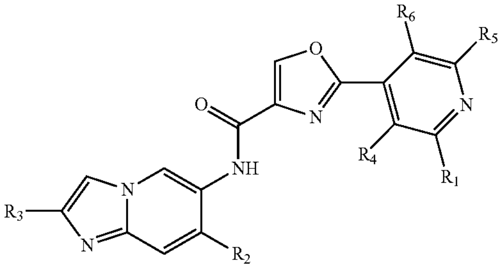

wherein, $R_1$ is selected from H, F, Cl, Br, I, OH, CN, $NR_aR_b$, $CH_3$, —C(═O)—$C_{1-3}$ alkyl and $C_{1-3}$ alkoxy, and the $C_{1-3}$ alkyl and $C_{1-3}$ alkoxy are optionally substituted with 1, 2 or 3 $R_c$;

$R_4$ is selected from H, F, Cl, Br, I, OH, CN, $NR_aR_b$, $C_{1-3}$ alkyl and —C(═O)—$C_{1-3}$ alkyl, and the $C_{1-3}$ alkyl is optionally substituted with 1, 2 or 3 $R_d$;

or, $R_1$ and $R_4$ are attached to form pyrrolyl with the attached atoms;

$R_2$ is selected from

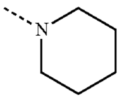, 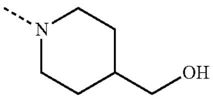,

-continued

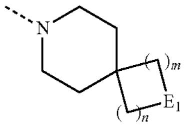

and

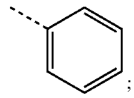

;

$R_3$ is selected from

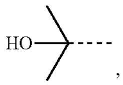

,

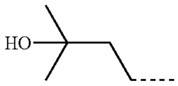

,

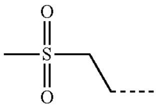

and

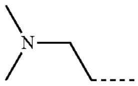

;

$E_1$ is selected from NH, O and S;

$R_5$ and $R_6$ are independently selected from H, F, Cl, Br, I, OH, CN, —C(=O)—$C_{1-3}$ alkyl and $C_{1-3}$ alkyl, and the $C_{1-3}$ alkyl is optionally substituted with 1, 2 or 3 $R_e$;

m is selected from 1 and 2;

n is selected from 1 and 2;

$R_a$ is selected from H and $C_{1-3}$ alkyl;

$R_b$ is selected from H, $C_{1-3}$ alkyl and —C(O)—$C_{1-3}$ alkyl;

$R_c$ is selected from F, Cl, Br and I;

$R_d$ is selected from F, Cl, Br and I;

$R_e$ is selected from F, Cl, Br and I;

on condition that:

1) when $R_2$ is selected from

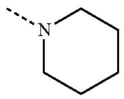

, $R_1$ is selected from $NR_aR_b$ and $C_{1-3}$ alkoxy, the $C_{1-3}$ alkoxy is optionally substituted with 1, 2 or 3 $R_c$, or $R_1$ and $R_4$ are attached to form pyrrolyl with the attached atoms;

2) when $R_2$ is selected from

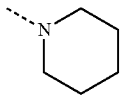

and $R_1$ is selected from $CH_3$, $R_3$ is selected from

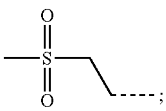

;

3) when $R_2$ is selected from

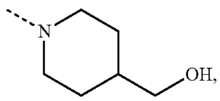

, $R_3$ is selected from

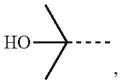

,

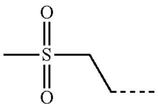

and

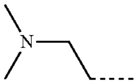

;

4) when $R_2$ is selected from

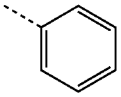

, $R_3$ is selected from

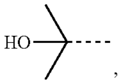

,

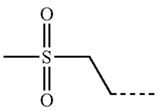

and

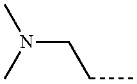

.

In some embodiments of the present disclosure, the $R_a$ is selected from H, $CH_3$, $CH_2CH_3$ and $C(CH_3)_2$, and the other variables are as defined in the present disclosure.

In some embodiments of the present disclosure, the $R_b$ is selected from H, $CH_3$, $CH_2CH_3$, $C(CH_3)_2$, —C(O)—$CH_3$, —C(O)—$CH_2CH_3$ and —C(O)—$C(CH_3)_2$, and the other variables are as defined in the present disclosure.

In some embodiments of the present disclosure, the $R_1$ is selected from H, F, Cl, Br, I, OH, CN, $NR_aR_b$, $CH_3$, —C(=O)—$CH_3$ and $OCH_3$, and the $OCH_3$ is optionally substituted with 1, 2 or 3 $R_c$, and the other variables are as defined in the present disclosure.

In some embodiments of the present disclosure, the $R_1$ is selected from $NH_2$, $NHCH_3$, $N(CH_3)_2$, $NHC(O)CH_3$ and $OCH_3$, and the other variables are as defined in the present disclosure.

In some embodiments of the present disclosure, the $R_1$ and $R_4$ are attached to form a ring with the attached atoms so that the structural fragment

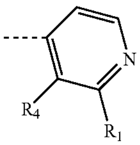

forms

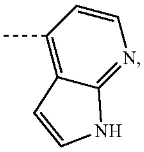

, and the other variables are as defined in the present disclosure.

In some embodiments of the present disclosure, the $R_2$ is selected from

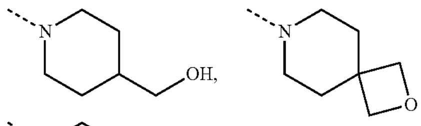

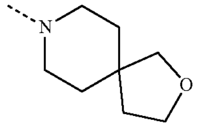

and

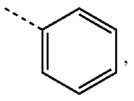

and the other variables are as defined in the present disclosure.

In some embodiments of the present disclosure, the $R_4$, $R_5$ and $R_6$ are independently selected from H, F, Cl, Br, I, OH, CN, $NH_2$, $NH(CH_3)$, $N(CH_3)_2$, $CH_3$, $CH_2CH_3$ and $C(CH_3)_2$, and the $CH_3$, $CH_2CH_3$ and $C(CH_3)_2$ are optionally substituted with 1, 2 or 3 $R_c$, and the other variables are as defined in the present disclosure.

In some embodiments of the present disclosure, the $R_4$, $R_5$ and $R_6$ are independently selected from H, F, Cl, Br, I, $CH_3$ and $CF_3$, and the other variables are as defined in the present disclosure.

In some embodiments of the present disclosure, the compound or the pharmaceutically acceptable salt thereof, wherein the compound is selected from (I)

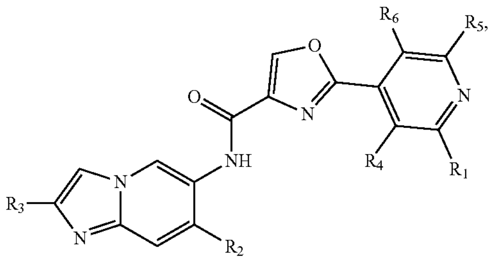

(II-1)

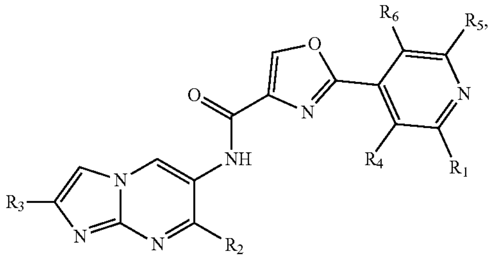

(II-2)

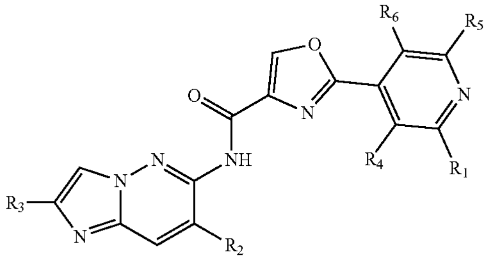

and

-continued (II-3)

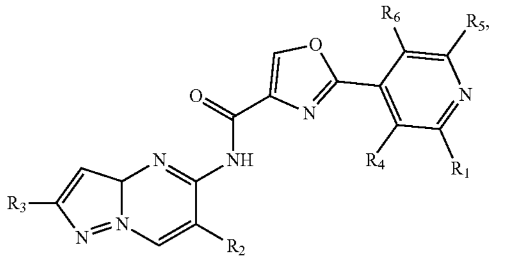

wherein, $R_1$, $R_2$, $R_3$, $R_4$, $R_5$ and $R_6$ are as defined in the present disclosure.

In some embodiments of the present disclosure, the compound or the pharmaceutically acceptable salt thereof, wherein the compound is selected from (III)

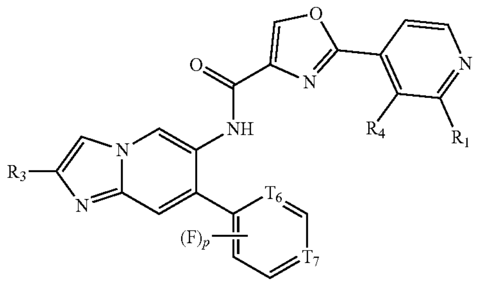

wherein, $R_1$ and $R_4$ are as defined in the present disclosure;

$T_6$ is selected from CH and N;

$T_7$ is selected from CH and N;

and $T_6$ and $T_7$ are not simultaneously N;

$R_3$ is selected from

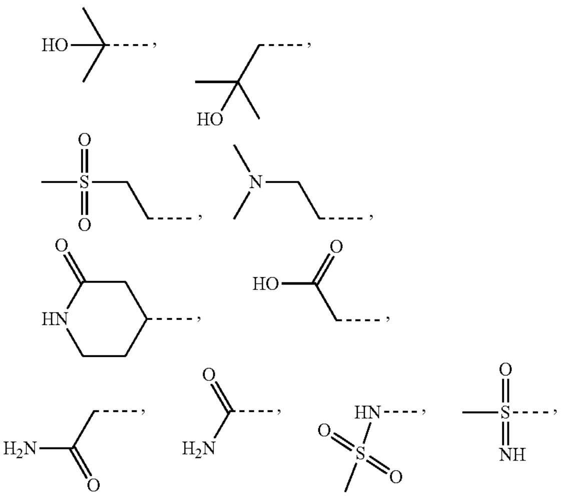

-continued

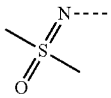

and

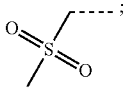

p is 0 or 1.

In some embodiments of the present disclosure, the compound or the pharmaceutically acceptable salt thereof, wherein the compound is selected from (P)

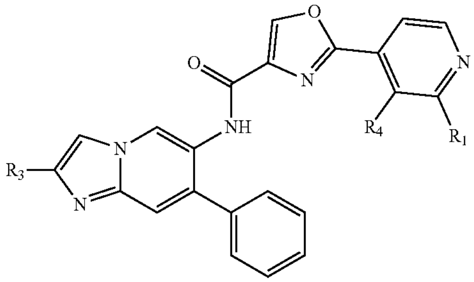

wherein, $R_1$ and $R_4$ are as defined in the present disclosure;

$R_3$ is selected from

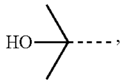

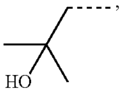

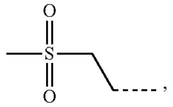

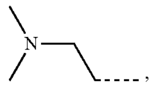

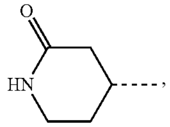

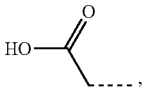

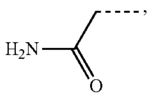

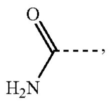

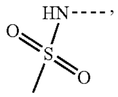

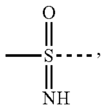

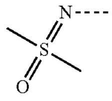

and

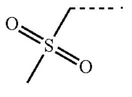

In some embodiments of the present disclosure, the $R_4$ is selected from H, F, Cl, Br, I, OH, CN, $NH_2$, $NH(CH_3)$, $N(CH_3)_2$, $CH_3$, $CH_2CH_3$ and $CH(CH_3)_2$, and the $CH_3$, $CH_2CH_3$ and $CH(CH_3)_2$ are optionally substituted with 1, 2 or 3 F, and the other variables are as defined in the present disclosure.

In some embodiments of the present disclosure, the $R_4$ is selected from H, F, Cl, Br, I, $CH_3$ and $CF_3$, and the other variables are as defined in the present disclosure.

There are also some embodiments of the present disclosure obtained by an arbitrary combination of the above variables.

The present disclosure also provides a compound represented by the following formula or a pharmaceutically acceptable salt thereof,

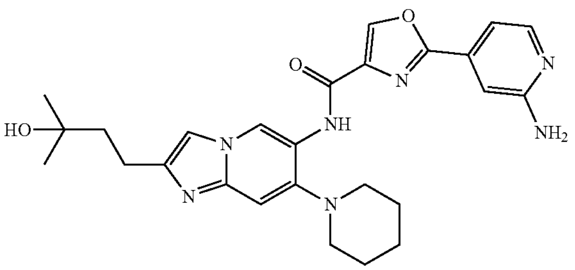

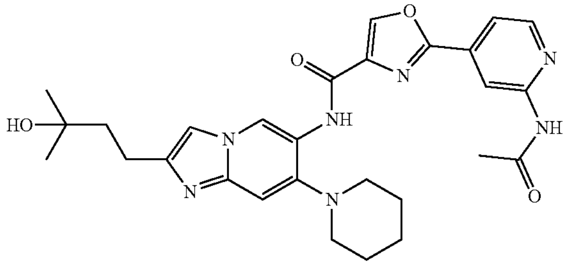

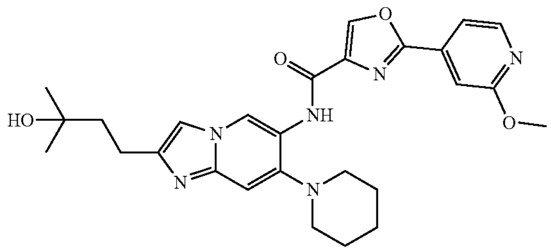

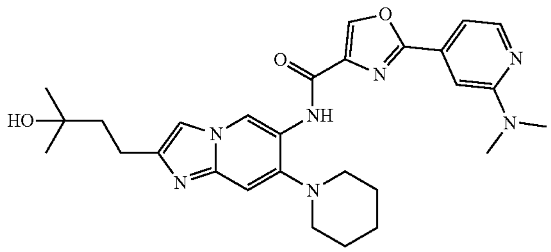

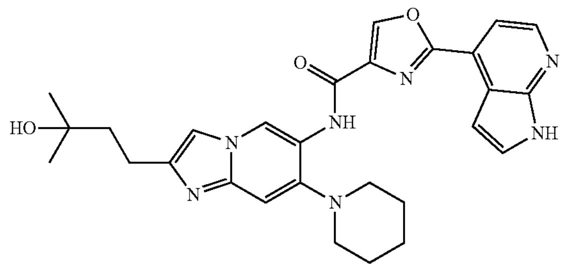

-continued
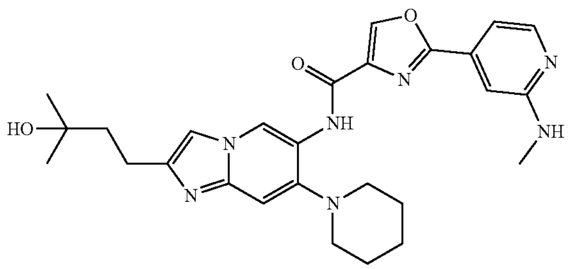
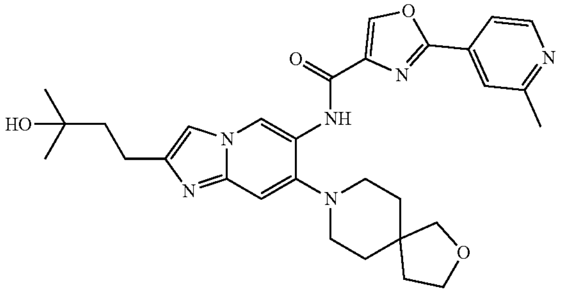
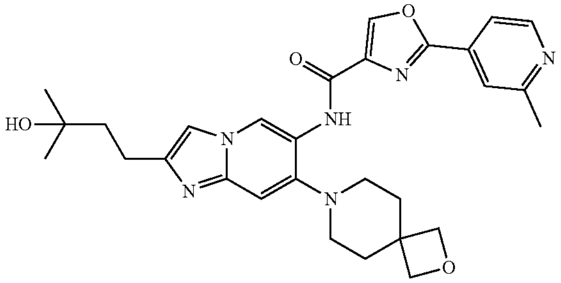
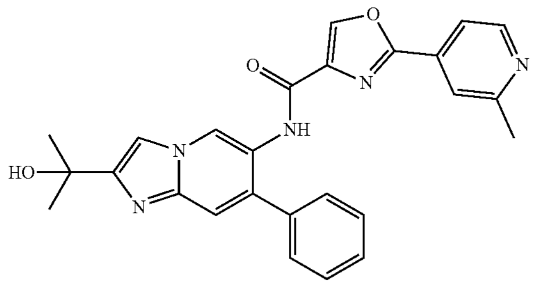
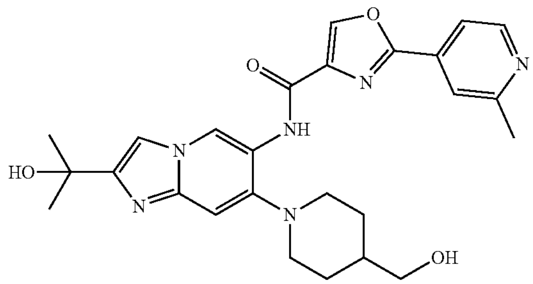
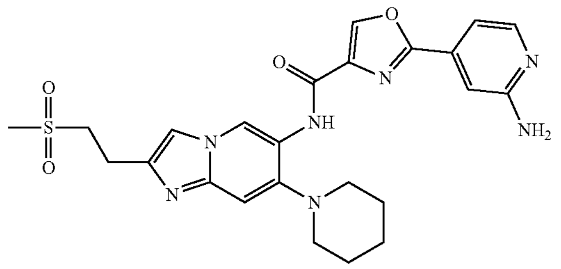
-continued
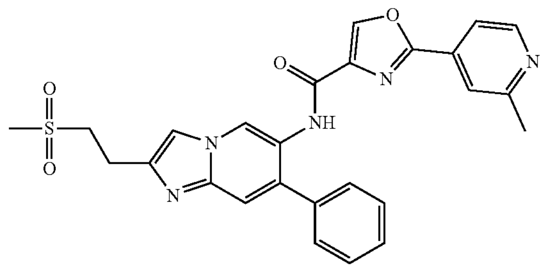
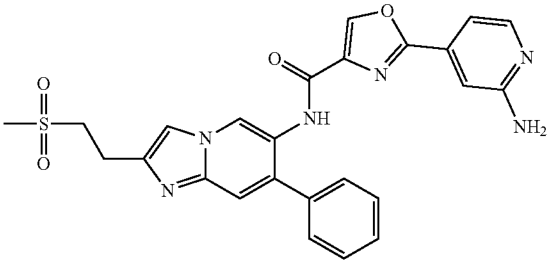
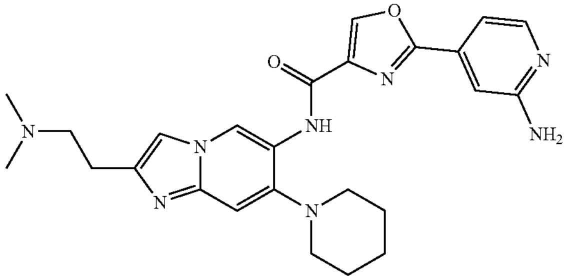
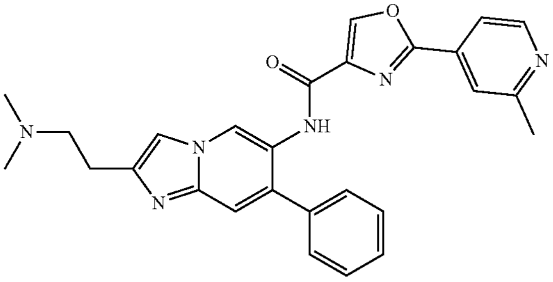
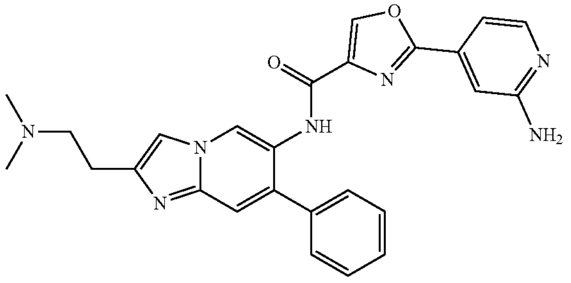
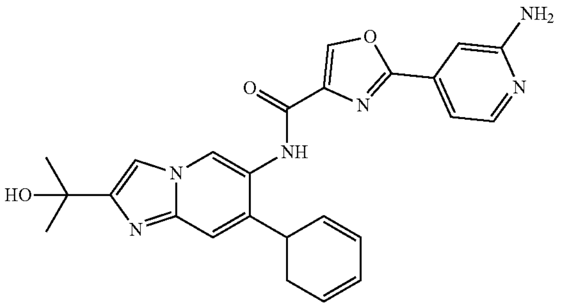

-continued
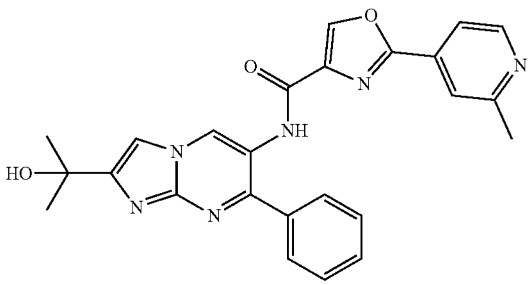
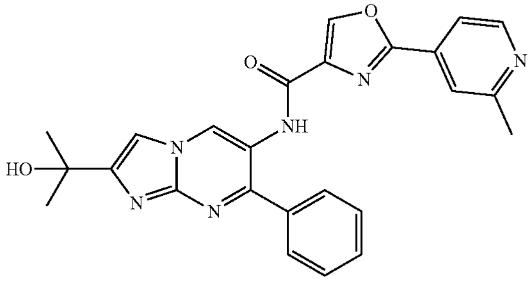
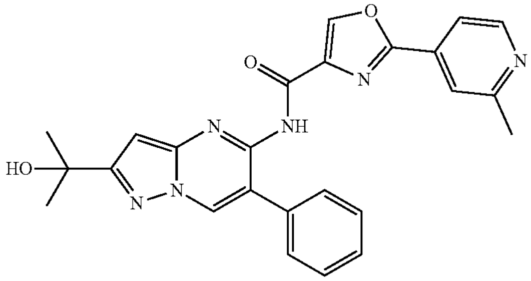
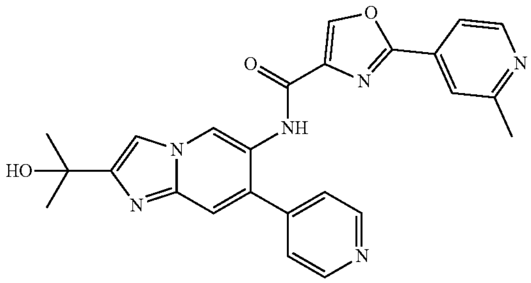
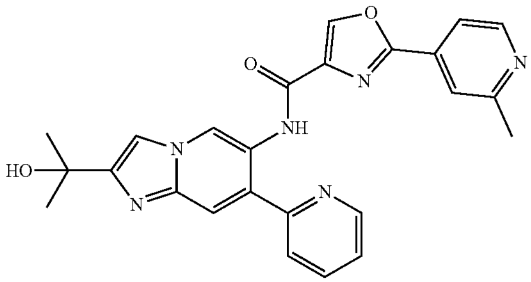
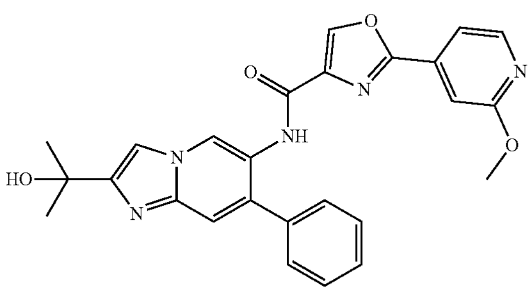
-continued
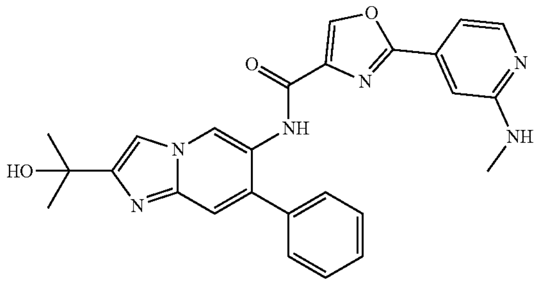
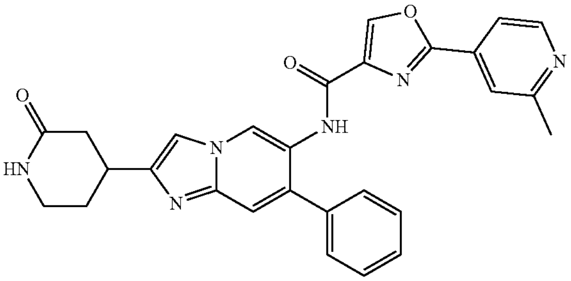
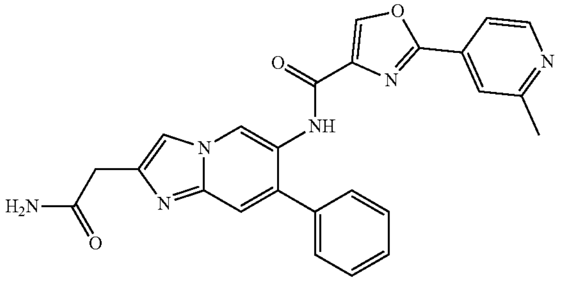
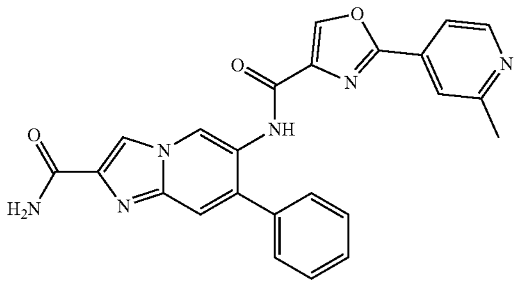
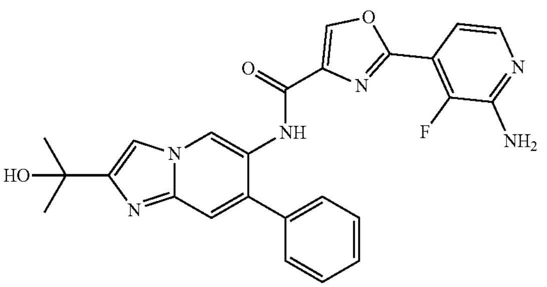
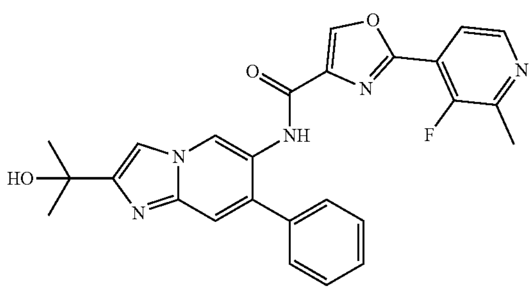

-continued

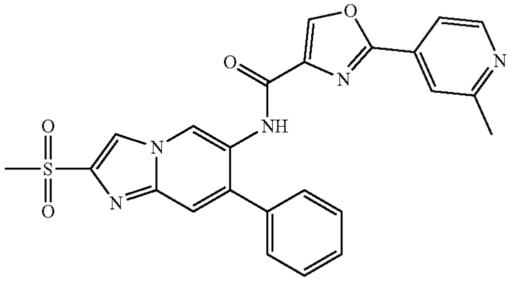

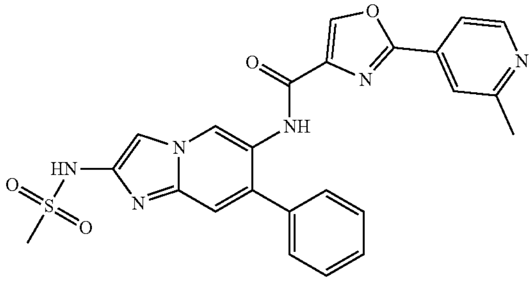

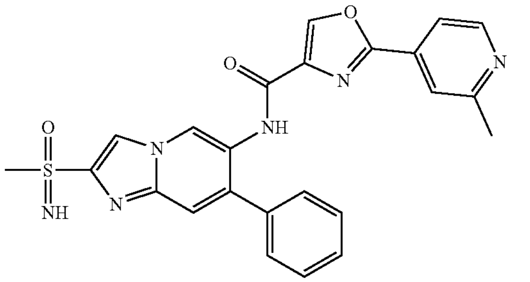

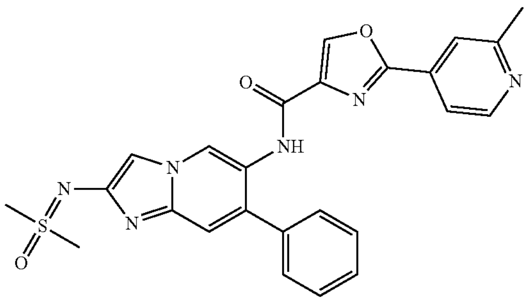

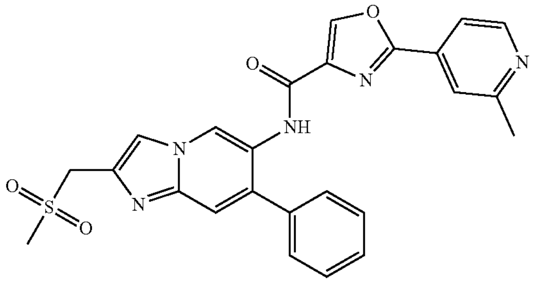

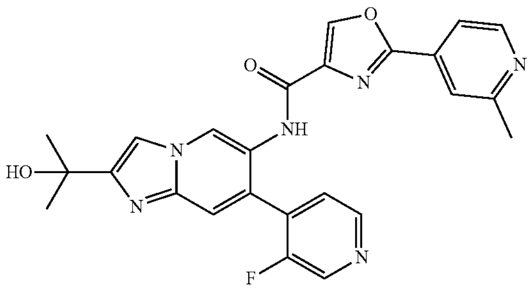

-continued

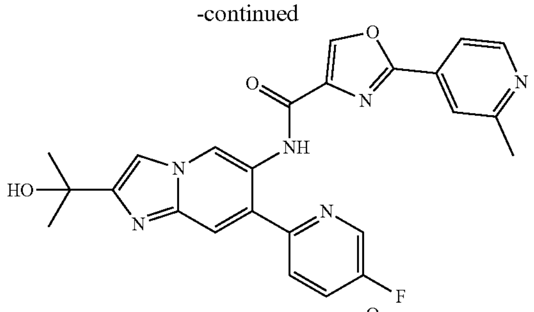

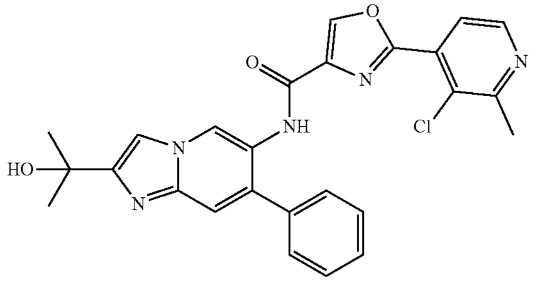

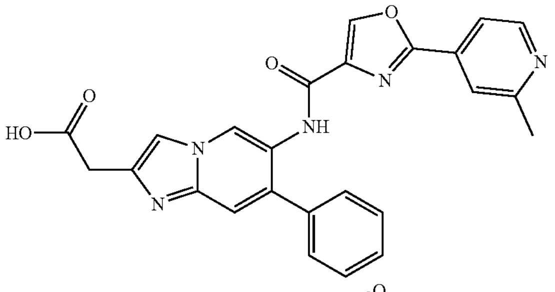

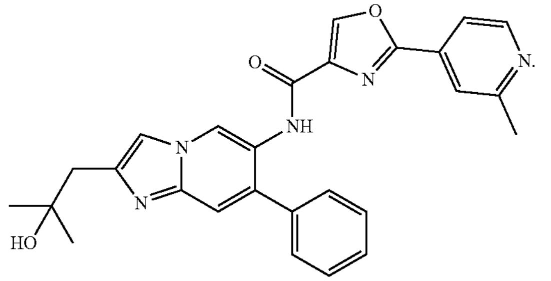

The present disclosure also provides a use of the compound or the pharmaceutically acceptable salt thereof in the manufacture of a medicament for the treatment of hematoma-related.

In some embodiments of the present disclosure, the hematoma is a diffuse large B-cell lymphoma.

Technical Effect

The compound of the present disclosure generally exhibits its good inhibitory activity against IRAK4 and BTK. The compound of the present disclosure generally exhibits a good activity of inhibiting cell TNF-α production in THP-1 cells, and a good activity of inhibiting cell proliferation in OCI-LY10, TMD-8 and OCI-LY3 cells. The compound of the present disclosure can reduce the secretion of TNF-α in animal plasma. The compound of the present disclosure exhibits remarkable tumor inhibitory effect in the in vivo pharmacodynamic study of TMD8 cell subcutaneous xenograft tumor model. The compound of the present disclosure has excellent pharmacokinetic properties.

Definition and Description

Unless otherwise specified, the following terms and phrases when used herein have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

The compound of the present disclosure may contain an unnatural proportion of atomic isotope at one or more than one atom(s) that constitute the compound. For example, the compound can be radiolabeled with a radioactive isotope, such as tritium ($^{3}H$), iodine-125 ($^{125}I$) or C-14 ($^{14}C$). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure.

The term "optional" or "optionally" means that the subsequent event or condition may occur but not requisite, and the term includes the instance in which the event or condition occurs and the instance in which the event or condition does not occur.

The term "substituted" means one or more than one hydrogen atom(s) on a specific atom are substituted with the substituent, including heavy hydrogen and hydrogen variables, as long as the valence of the specific atom is normal and the substituted compound is stable. When the substituent is an oxygen (i. e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the enumerative linking group does not indicate the direction for linking, the direction for linking is arbitrary, for example, the linking group L contained in

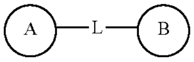

is -M-W—, then -M-W— can link ring A and ring B to form

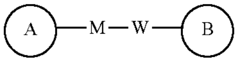

in the direction same as left-to-right reading order, and link ring A and ring B form

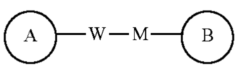

in the direction contrary to left-to-right reading order. A combination of the linking groups, substituents and/or variables thereof is allowed only when such combination can result in a stable compound.

Unless otherwise specified, when a group has one or more linkable sites, any one or more sites of the group can be linked to other groups through chemical bonds. When the linking site of the chemical bond is not positioned, and there is H atom at the linkable site, then the number of H atom at the site will decrease correspondingly with the number of chemical bond linking thereto so as to become the group with the corresponding valence. The chemical bond between the site and other groups can be represented by a straight solid bond (  ), a straight dashed bond (  ) or a wavy line (  ).

For example, the straight solid bond in —$OCH_3$ means that it is linked to other groups through the oxygen atom in the group; the straight dashed bonds in

means that it is linked to other groups through the two ends of nitrogen atom in the group; the wave lines in

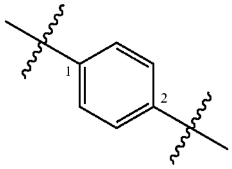 [SMILES: *c1ccc(*)cc1]

means that the phenyl group is linked to other groups through carbon atoms at position 1 and position 2;

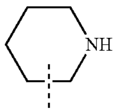

means that it can be linked to other groups through any linkable sites on the piperidinyl by one chemical bond, including at least four linkage ways, including

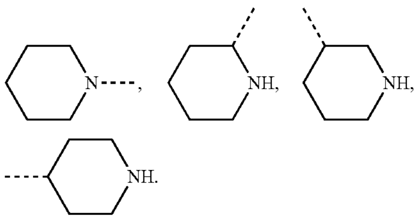

Even though the H atom is drawn on the —N—,

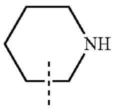

still includes the linkage way of

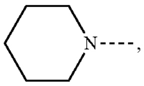

merely when one chemical bond is connected, the H of this site will be reduced and become the corresponding monovalent piperidinyl.

Unless otherwise specified, the term "$C_{1-3}$ alkyl" refers to a linear or branched saturated hydrocarbon group containing 1 to 3 carbon atoms. The $C_{1-3}$ alkyl group includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "$C_{1-3}$ alkoxy" refers to an alkyl group containing 1 to 3 carbon atoms that are connected to the rest of the molecule through an oxygen atom. The $C_{1-3}$ alkoxy includes $C_{1-2}$, $C_{2-3}$, $C_1$, $C_2$ and $C_3$ alkoxy, etc. Examples of $C_{1-3}$ alkoxy include, but are not limited to, methoxy, ethoxy, propoxy (including n-propoxy and isopropoxy), etc.

Unless otherwise specified, the term "halo" or "halogen" by itself or as part of another substituent refers to fluorine, chlorine, bromine or iodine atom.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred embodiments include but are not limited to the embodiments of the present disclosure.

The solvent used in the present disclosure is commercially available. The following abbreviations are used in the present disclosure: DMSO refers to dimethyl sulfoxide; EtOH refers to ethanol; MeOH refers to methanol; M refers to mol/L; N/A refers to untested; $MgCl_2$ refers to magnesium chloride; EGTA refers to ethylenebis(oxyethylenenitrilo) tetraacetic acid; and $Na_3VO_4$ refers to sodium vanadate.

The structure of the compounds of the present disclosure can be confirmed by conventional methods known to those skilled in the art, and if the disclosure involves an absolute configuration of a compound, then the absolute configuration can be confirmed by conventionally technical means in the art. For example, in the case of single crystal X-ray diffraction (SXRD), collecting diffraction intensity data from the cultured single crystal using a Bruker D8 venture diffractometer with CuKα radiation as the light source and scanning mode: φ/ω scan, and after collecting the relevant data, the crystal structure can be further analyzed by direct method (Shelxs97), and the absolute configuration can be confirmed.

The compounds of the present disclosure are named according to the conventional naming principles in the art or by ChemDraw® software, and the commercially available compounds use the supplier catalog names.

DETAILED DESCRIPTION OF THE PREFERRED EMBODIMENT

Figure 1:
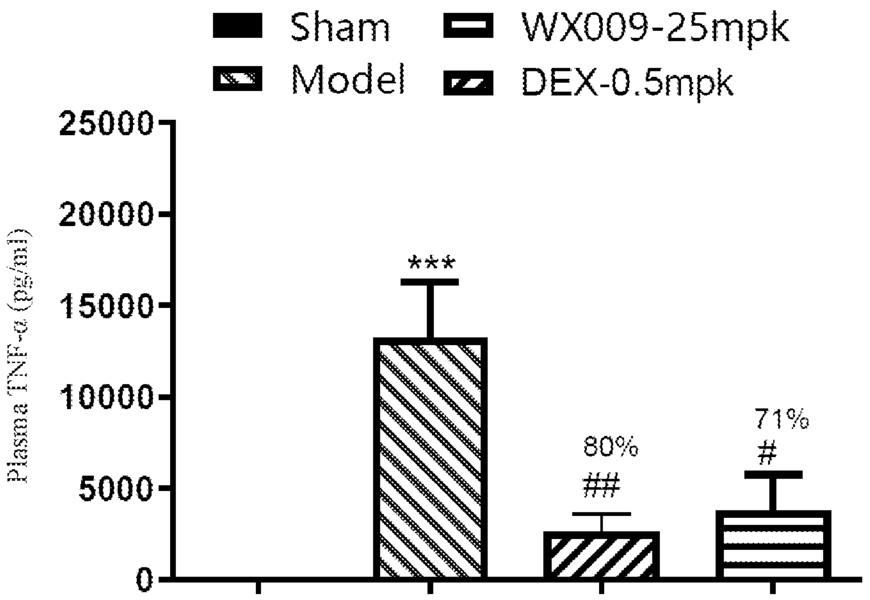
FIG. 1 shows a graph of plasma TNF-α concentration.

The following embodiments further illustrate the present disclosure, but the present disclosure is not limited thereto. The present disclosure has been described in detail herein, and its specific embodiments have also been disclosed, for one skilled in the art, it is obvious to make various modifications and improvements to the embodiments of the present disclosure without departing from the spirit and scope of the present disclosure.

Reference Embodiment 1: Synthesis of Intermediate BB-1

BB-1

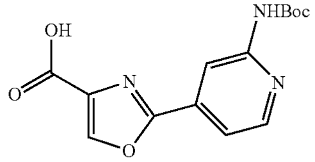

Synthetic Route:

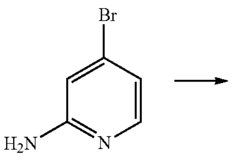

BB-1-1

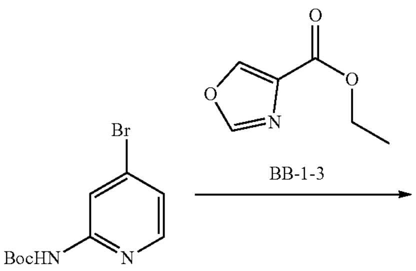

BB-1-2

-continued

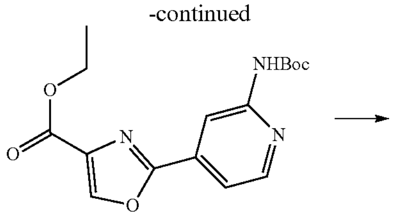

BB-1-4

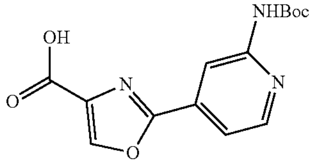

BB-1

Step 1: Synthesis of Compound BB-1-2

Compound BB-1-1 (5 g) was added to dichloromethane (20 mL), and then 4-dimethylaminopyridine (353.07 mg) and di-tert-butyl dicarbonate (15.77 g) were added, and the resulting mixed solution was stirred at 25° C. for 16 hours. After the reaction solution was concentrated under reduced pressure, the crude product was purified by column chromatography (eluent: petroleum ether/ethyl acetate=100:0 to 70:30) to obtain compound BB-1-2.

LCMS (ESI) m/z: 216.9 $[M-55]^+$

Step 2: Synthesis of Compound BB-1-4

N, N-dimethylformamide (10 mL) was added to compound BB-1-2 (1.0 g), and then compound BB-1-3 (620.04 mg), cesium carbonate (2.39 g) and [1,1'-bis (diphenylphosphino) ferrocene] palladium dichloride (267.90 mg) were added, the reaction solution was stirred at 60° C. for 16 hours under nitrogen protection. The reaction solution was concentrated under reduced pressure, the solvent was removed and the crude product was purified by column chromatography (eluent: petroleum ether/ethyl acetate=100:0 to 0:100) to obtain compound BB-1-4.

LCMS (ESI) m/z: 278.1 $[M-55]^+$

Step 3: Synthesis of Compound BB-1

Compound BB-1-4 (0.6 g) was dissolved in methanol (20 mL) and water (20 mL), then sodium hydroxide (144.00 mg) was added and the reaction mixture was stirred at 40° C. for 0.5 hours. The reaction solution was concentrated under reduced pressure to remove methanol, then water (50 mL) was added, and 1 M diluted hydrochloric acid was added dropwise while stirring at 0° C. to adjust the pH to about 2, and solids were precipitated. After filtration, the filter cake was washed with water (10 mL). The filter cake was collected and concentrated under reduced pressure to obtain compound BB-1.

$^1H$ NMR (400 MHz, DMSO-$d_6$) δ=13.34 (s, 1H), 10.14 (s, 1H), 8.96 (s, 1H), 8.59-8.25 (m, 2H), 7.56 (dd, J=1.2 Hz, J=5.2 Hz, 1H), 1.51 (s, 9H).

LCMS (ESI) m/z: 250.0 $[M-55]^+$

Reference Embodiment 2: Synthesis of Intermediate BB-2

BB-2

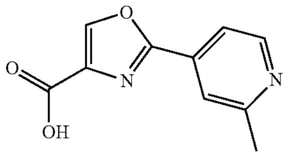

Synthetic Route:

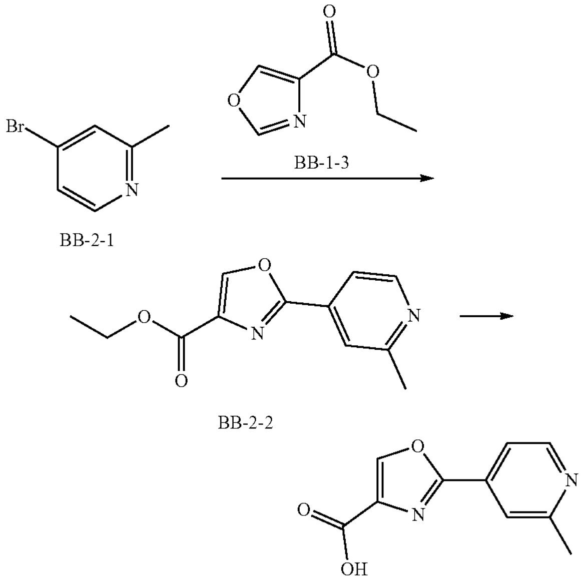

BB-2-1

BB-2-2

BB-2

Step 1: Synthesis of Compound BB-2-2

Compound BB-2-1 (16 g) and compound BB-1-3 (13.13 g) were added into N,N-dimethylformamide (200.0 mL), then palladium acetate (4.18 g), cesium carbonate (60.61 g), tri-o-tolylphosphine (11.32 g) were added, and reaction solution was stirred at 100° C. for 12 hours. The reaction solution was filtered and concentrated under reduced pressure, and the crude product was purified by column chromatography (eluent: petroleum ether/ethyl acetate=100:0 to 87:13) to obtain compound BB-2-2.

$^1H$ NMR (400 MHz, $CD_3OD$) δ=8.73 (s, 1H), 8.62 (s, 1H), 7.97 (s, 1H), 7.87 (s, 1H), 4.45-4.40 (m, 2H), 2.66 (s, 3H), 1.43-1.40 (m, 3H).

LCMS (ESI) m/z=233.2[M+H]+

Step 2: Synthesis of Compound BB-2

Compound BB-2-2 (6 g) was added to anhydrous methanol (30 mL) and water (30 mL), then sodium hydroxide (2.07 g) was added, and the reaction was carried out at 30° C. for 6 hours. After the reaction solution was concentrated under reduced pressure to remove methanol, the pH was adjusted to about 5 with 6 M hydrochloric acid, and after filtration, the filter cake was concentrated under reduced pressure. Toluene (100.0 mL) was added and the system was concentrated under reduced pressure to remove water to obtain compound BB-2.

$^1H$ NMR (400 MHz, $CD_3OD$) δ=8.69 (s, 1H), 8.62 (s, 1H), 7.99 (s, 1H), 7.89 (s, 1H), 2.66 (s, 3H).

LCMS (ESI) m/z=205.2[M+H]+

Reference Embodiment 3: Synthesis of Intermediate BB-3

BB-3

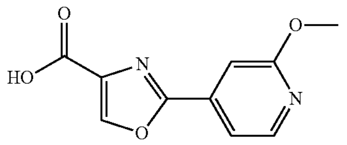

Synthetic Route:

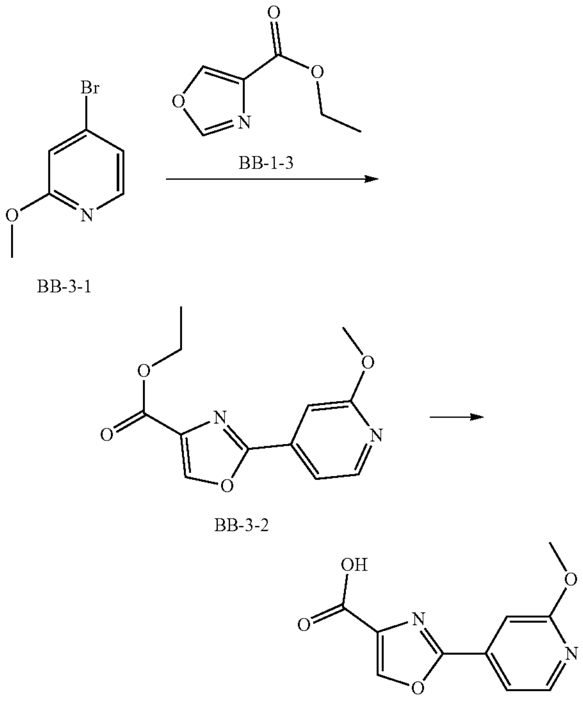

BB-3-1

BB-3-2

BB-3

Step 1: Synthesis of Compound BB-3-2

N,N-dimethylformamide (1 mL) was added to compound BB-3-1 (230 mg), and then compound BB-1-3 (207.16 mg), potassium tert-butoxide (274.52 mg), palladium acetate (27.46 mg) and tri-o-tolylphosphine (37.23 mg) were added, the mixed solution was stirred at 110° C. for 16 hours under nitrogen atmosphere. The reaction solution was concentrated under reduced pressure to remove the solvent and the crude product was purified by column chromatography (eluent: petroleum ether/ethyl acetate=100:0 to 50:50) to obtain compound BB-3-2.

LCMS m/z: 249.1$[M+H]^+$

Step 2: Synthesis of Compound BB-3

Compound BB-3-2 (150 mg) was dissolved in methanol (3 mL) and water (3 mL), then sodium hydroxide (48.34 mg) was added to the reaction system and the mixture was stirred at 40° C. for 2 hours. The reaction solution was concentrated under reduced pressure to remove methanol, then water (20 mL) was added, and 1 M diluted hydrochloric acid was added dropwise with stirring at 0° C. to adjust the pH to about 2, and solids were precipitated. After filtration, the filter cake was washed with water (2 mL), the filter cake was collected, and concentrated under reduced pressure to obtain compound BB-3.

$^{1}$H NMR (400 MHz, DMSO-$d_6$) δ=8.95 (s, 1H), 8.36 (d, J=5.2 Hz, 1H), 7.52 (dd, J=1.2 Hz, J=5.2 Hz, 1H), 7.27 (s, 1H), 3.91 (s, 3H).

LCMS m/z: 221.0[M+H]+

Reference Embodiment 4: Synthesis of Intermediate BB-4

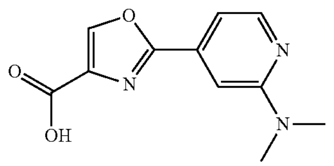

BB-4

Synthetic Route:

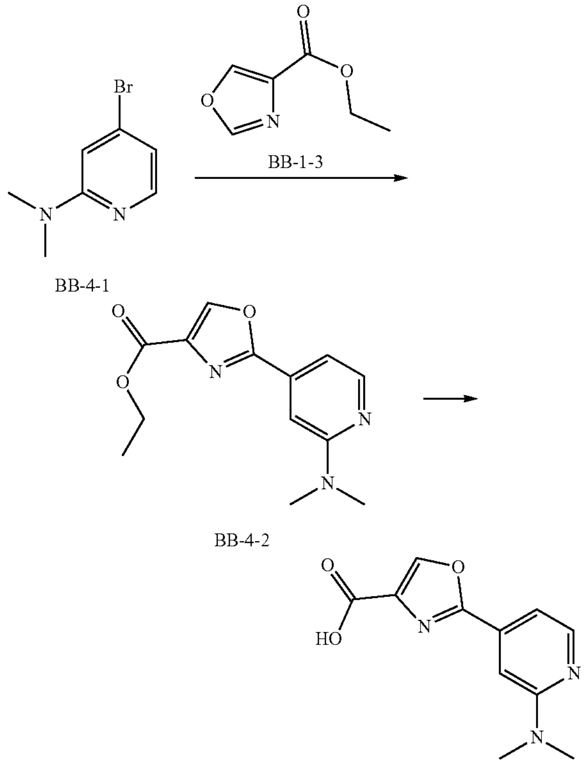

BB-4-1

BB-4-2

BB-4

Step 1: Synthesis of Compound BB-4-2

N, N-dimethylformamide (20 mL) was added to compound BB-4-1 (1 g), and then compound BB-1-3 (842.27 mg), cesium carbonate (3.24 g) and [1,1'-bis (diphenylphosphino) ferrocene] palladium dichloride (363.92 mg) were added, the obtained mixed solution was stirred at 60° C. for 16 hours under nitrogen protection. The reaction solution was concentrated under reduced pressure to remove the solvent and the crude product was purified by column chromatography (eluent: dichloromethane/methanol=100:0 to 80:20) to obtain compound BB-4-2.

LCMS m/z: 261.9[M+H]+

Step 2: Synthesis of Compound BB-4

Methanol (10 mL) and water (10 mL) were added to compound BB-4-2 (250 mg), then aqueous sodium hydroxide solution (3 M, 637.90 μL) was added, and the mixed solution was stirred at 25° C. for 16 hours. The reaction solution was concentrated under reduced pressure to remove methanol, water (50 mL) was added, 1 M diluted hydrochloric acid was added dropwise at 0° C. while stirring, the pH was adjusted to about 2, and solids were precipitated, after filtration, the filter cake was washed with water (10 mL), and collected to obtain compound BB-4.

$^{1}$H NMR (400 MHz, DMSO-$d_6$) δ=13.30 (s, 1H), 8.92 (s, 1H), 8.26 (d, J=5.6 Hz, 1H), 7.09 (s, 2H), 3.10 (s, 6H).

LCMS m/z: 233.9[M+H]+

Reference Embodiment 5: Synthesis of Intermediate BB-5

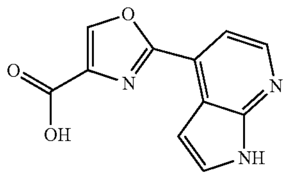

BB-5

Synthetic Route:

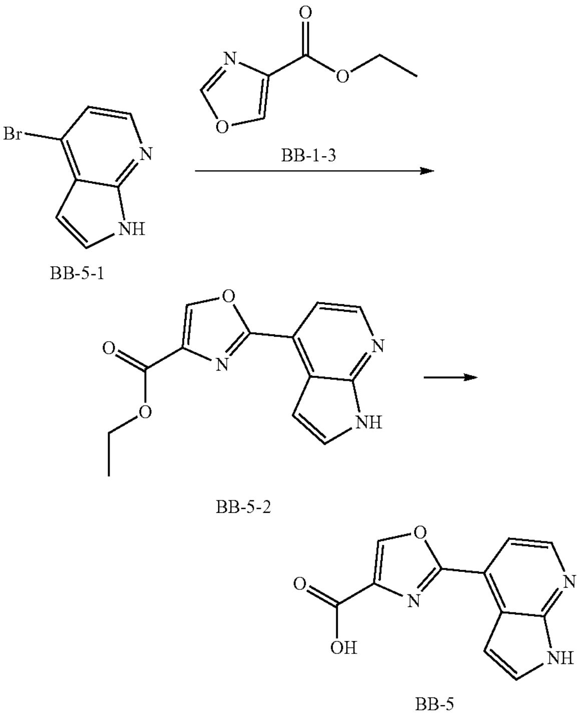

BB-5-1

BB-5-2

BB-5

Step 1: Synthesis of Compound BB-5-2

Compound BB-5-1 (1 g), compound BB-1-3 (716.25 mg), cesium carbonate (4.96 g) and [1,1'-bis (diphenylphosphino)

ferrocene] palladium dichloride (371.36 mg) were added successively into the reaction flask, and then N,N-dimethylformamide (20 mL) was added, the reaction solution was stirred at 90° C. for 3 hours under nitrogen protection. Ethyl acetate (50 mL), saturated brine (50 mL) and water (50 mL) were added to the reaction solution, after filtration, the filtrate was extracted and separated, the aqueous phase was extracted with ethyl acetate (30 mL), the organic phases were combined, dried with anhydrous sodium sulfate, filtered, and concentrated under reduced pressure, and the crude product was purified by column chromatography (eluent: petroleum ether/ethyl acetate=100:0 to 0:100) to obtain compound BB-5-2.

LCMS (ESI) m/z: 258.0[M+H]+

Step 2: Synthesis of Compound BB-5

Compound BB-5-2 (130 mg) was added to the reaction flask, then anhydrous ethanol (2.5 mL) was added, and finally the mixed solution of water (1.5 mL) and sodium hydroxide (60.64 mg) were added, and the reaction solution was stirred at 50° C. for 2 hours. The solvent was concentrated under reduced pressure, water (5 mL) was added for ultrasonic dissolution, then ethyl acetate (5 mL) was added for extraction and liquid separation, the aqueous phase was collected and the pH was adjusted to 4 with 4 M hydrochloric acid, after filtration, and the filter cake was rinsed with water (5 mL). The filter cake was concentrated under reduced pressure to remove the solvent to obtain compound BB-5.

LCMS (ESI) m/z: 230.0[M+H]+

Reference Embodiment 6: Synthesis of Intermediate BB-6

BB-6

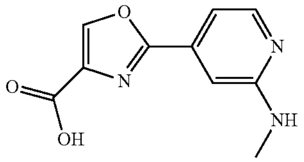

Synthetic Route:

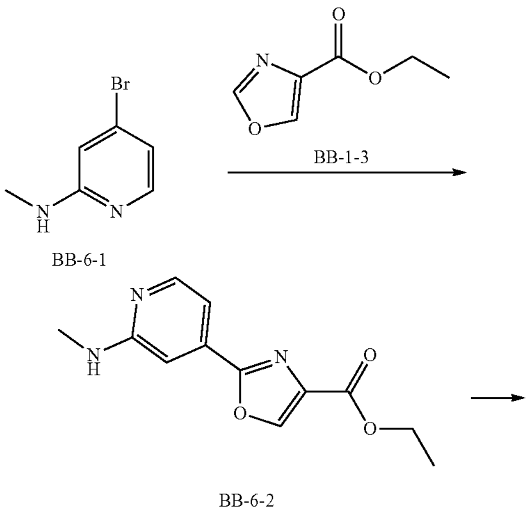

-continued

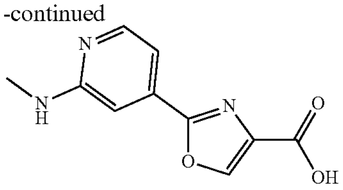

BB-6

Step 1: Synthesis of Compound BB-6-2

N,N-dimethylformamide (5 mL) was added to compound BB-6-1 (0.5 g), and then compound BB-1-3 (452.72 mg), cesium carbonate (1.74 g) and [1,1'-bis (diphenylphosphino) ferrocene] palladium dichloride (7.80 mg) were added, the obtained mixed solution was stirred at 60° C. for 16 hours under nitrogen protection. After concentrated under reduced pressure, the obtained crude product was purified by column chromatography (eluent: dichloromethane/methanol=100:0 to 80:20) to obtain compound BB-6-2.

LCMS (ESI) m/z: 247.9[M+H]+

Step 2: Synthesis of Compound BB-6

Methanol (10 mL) and water (10 mL) were added to compound BB-6-2 (200 mg), then aqueous sodium hydroxide solution (3 M, 539.27 μL) was added, and the mixed solution was stirred at 25° C. for 16 hours. After the system was concentrated under reduced pressure, water (50 mL) was added, 1 M diluted hydrochloric acid was added dropwise at 0° C. while stirring to adjust the pH to about 7, and solids were precipitated, after filtration, the filter cake was washed with water (10 mL), and collected to obtain compound BB-6.

$^1H$ NMR (400 MHz, DMSO-$d_6$) δ=8.88 (s, 1H), 8.16 (d, J=5.2 Hz, 1H), 7.15-6.96 (m, 2H), 6.91 (d, J=4.4 Hz, 1H), 2.83 (d, J=4.4 Hz, 3H).

LCMS (ESI) m/z: 219.9[M+H]+

Each intermediate in Table 1 below was a commercially available reagent.

TABLE 1

| Number | Structure | CAS |
|---|---|---|
| B2-1 | 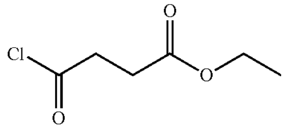 | 14794-31-1 |
| B1 | 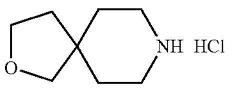 | 479195-19-2 |
| B3 | 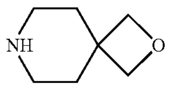 | 241820-91-7 |
| B4 | 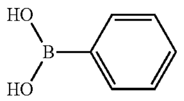 | 98-80-6 |
| B5 | 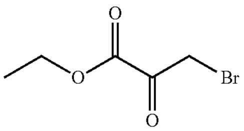 | 70-23-5 |

TABLE 1-continued

| Number | Structure | CAS |
|---|---|---|
| B6 | 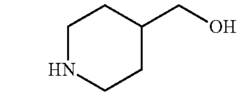 | 6457-49-4 |
| B7 | 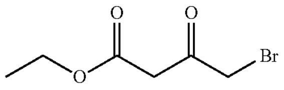 | 13176-46-0 |

Reference Embodiment 7: Synthesis of Intermediate B2

B2

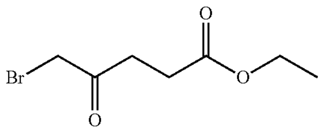

Synthetic Route:

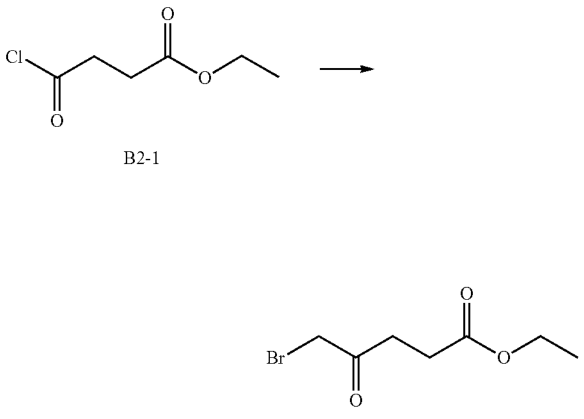

B2-1

B2

Step 1: Synthesis of Compound B2

Compound B2-1 (25 g) was added to acetonitrile (25 g), and then trimethylsilyl diazomethane (2 M, 113.92 mL) was added, and the reaction was carried out at 25° C. for 1 hour. After cooled to 0° C., the solution of hydrobromic acid (46.55 g, purity: 33%) in acetic acid was added slowly, after the adding, the reaction solution was heated to 25° C. and stirred for 1 hour. The solvent was concentrated under reduce pressure to obtain a crude product, and the crude product was purified by column chromatography (eluent: petroleum ether/ethyl acetate=100:0 to 90:10) to obtain compound B2.

$^1$H NMR (400 MHz, $CDCl_3$) δ=4.05-3.98 (m, 3H), 3.84 (s, 1H), 2.84-2.75 (m, 2H), 2.55-2.51 (m, 2H), 1.15-1.12 (m, 3H).

Reference Embodiment 8: Synthesis of Intermediate BB-7

BB-7

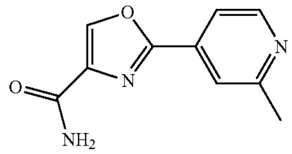

Synthetic Route:

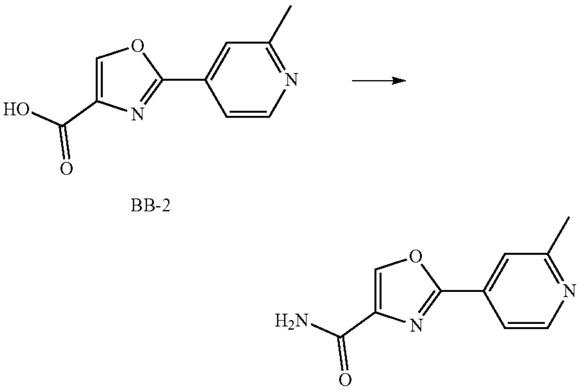

BB-2

BB-7

Step 1: Synthesis of Compound BB-7

Compound BB-2 (1 g) was dissolved in N,N-dimethylformamide (15 mL), and then ammonium chloride (523.96 mg), N-(3-dimethylaminopropyl)-N-ethylcarbodiimide (1.41 g), 1-hydroxybenzotriazole (992.67 mg) and diisopropylethylamine (3.16 g) were added, and the reaction was carried out at 25° C. for 16 hours. Then water (20 mL) was added to the reaction solution, then the mixture was extracted with ethyl acetate (20 mL), the aqueous phase was collected, and concentrated under reduced pressure to obtain the crude compound. The obtained crude product was purified by machine separation (column: Waters Xbridge BEH C18 (250*50 mm*10 μm); eluent: [Water (ammonium bicarbonate)-acetonitrile]; gradient acetonitrile %: 1%-35%, 10 min) to obtain compound BB-7.

LCMS (ESI) m/z: 204.2[M+H]+

$^1$H NMR (400 MHz, DMSO-$d_6$) δ=8.67 (s, 1H), 8.23 (s, 1H), 7.83-7.80 (m, 2H), 7.75-7.73 (m, 1H), 7.60 (s, 1H), 2.59 (3H).

Reference Embodiment 9: Synthesis of Intermediate BB-8

BB-8

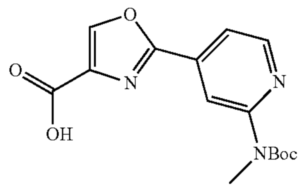

Synthetic Route:

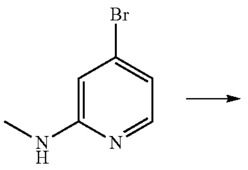

BB-6-1

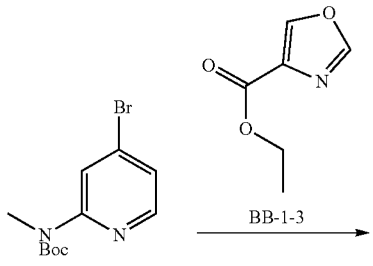

BB-8-1

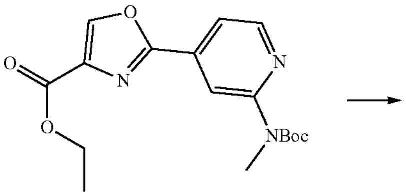

BB-8-2

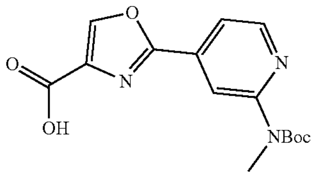

BB-8

Step 1: Synthesis of Compound BB-8-1

Compound BB-6-1 (1 g) was added to anhydrous tetrahydrofuran (20 mL), the temperature was lowered to −5° C., 1M solution of lithium bis (trimethylsilylamine) in hexane (10.69 mL) was added, after stirred for 10 min, di-tert-butyl carbonate (1.17 g) was added, and the temperature was raised to 25° C. and the reaction was carried out for 1 h. The reaction solution was added into saturated ammonium chloride aqueous solution (40 mL), extracted with ethyl acetate (40 mL*3), the organic phases were combined, dried with anhydrous sodium sulfate, filtered, the filtrate was concentrated under reduced pressure, and crude product was purified by column chromatography (eluent: petroleum ether/ethyl acetate=100:0 to 95:5) to obtain compound BB-8-1.

LCMS (ESI) m/z: 287.0[M+H]+

Step 2: Synthesis of Compound BB-8-2

BB-8-1 (0.75 g), compound BB-1-3 (368.60 mg), 1,1-bis (diphenylphosphine) ferrocene palladium chloride (191.11 mg), cesium carbonate (2.55 g) and N,N-dimethylformamide (7.5 mL) were added into a pre-dried reaction flask, and the reaction system was replaced with nitrogen for three times, and reacted at 60° C. for 16 hours. The reaction solution was poured into water (10 mL), extracted with ethyl acetate (10 mL*3), the organic phases were combined, washed with saturated brine (50 mL), dried with anhydrous sodium sulfate, filtered by suction, and spin-dried under reduced pressure, and then the crude product was purified by column chromatography (eluent: petroleum ether/ethyl acetate=100:0 to 0:100) to obtain compound BB-8-2.

LCMS (ESI) m/z: 348.2[M+H]+

Step 3: Synthesis of Compound BB-8

Compound BB-8-2 (0.55 g) was added to methanol (10 mL) and water (2 mL), then sodium hydroxide (126.66 mg) was added, and the reaction was carried out at 25° C. for 2 hours. The reaction solution was concentrated under reduced pressure until methanol was removed, the pH was adjusted to about 4 with 2M hydrochloric acid, after filtration, the filter cake under reduced pressure to obtain compound BB-8.

LCMS (ESI) m/z: 320.0[M+H]+

$^{1}H$ NMR (400 MHz, $CD_3OD$) δ=8.64 (s, 1H), 8.54 (d, J=5.20 Hz, 1H), 8.34 (s, 1H), 7.76-7.75 (m, 1H), 3.42 (s, 3H), 1.56 (s, 9H).

Reference Embodiment 10: Synthesis of Intermediate BB-9

BB-9

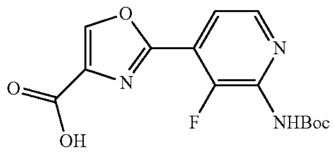

Synthetic Route:

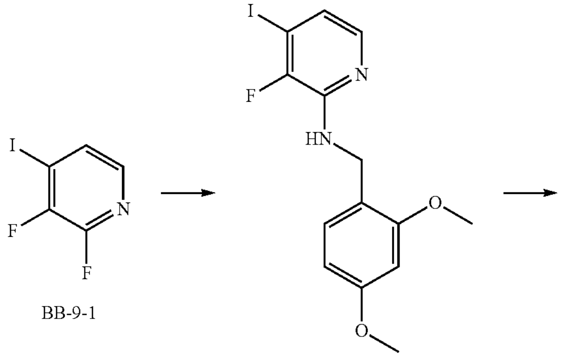

BB-9-1

BB-9-2

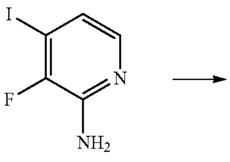

BB-9-3

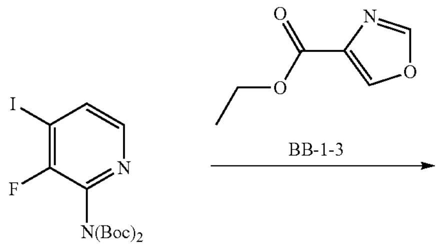

BB-9-4

-continued

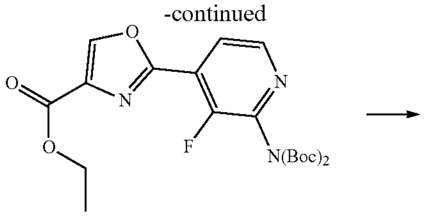

BB-9-5

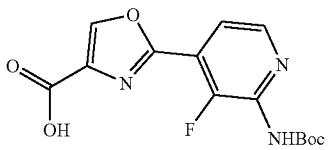

BB-9

Step 1: Synthesis of Compound BB-9-2

Compound BB-9-1 (2 g), 2,4-dimethoxybenzylamine (1.53 g), dimethyl sulfoxide (10 mL) and N,N diisopropylethylamine (3.22 g) were added into the reaction flask, the reaction system was replaced by nitrogen for three times and the reaction was carried out at 120° C. for 2 hours. Then water (10 mL) and methyl tert-butyl ether (30 mL*3) were added to the reaction solution for extraction, the organic phases were combined, and concentrated to obtain compound BB-9-2.

$^1$H NMR (400 MHz, $CDCl_3$) δ=7.56 (d, J=5.20 Hz, 1H), 7.25 (d, J=8.00 Hz, 1H), 6.84 (dd, J=5.20 Hz, J=4.00 Hz, 1H), 6.53-6.40 (m, 2H), 5.08 (s, 1H), 4.58 (d, J=5.60 Hz, 2H), 3.85 (s, 3H), 3.81 (s, 3H).

Step 2: Synthesis of Compound BB-9-3

Compound BB-9-2 (3 g) and trifluoroacetic acid (15 mL) were added into a reaction flask, and the reaction was carried out at 20° C. for 3 h, and ice water (50 mL) was added to the reaction solution, saturated sodium bicarbonate solution was added to adjust the pH to about 8, then dichloromethane (50 mL*2) was added for extraction, the organic phases were combined, washed with saturated brine, and dried with anhydrous sodium sulfate, filtered, and the filtrate was concentrated to obtain compound BB-9-3.

LCMS: m/z (ESI)=238.9[M+H]$^+$ $^1$H NMR (400 MHz, $CDCl_3$) δ=7.50 (d, J=5.20 Hz, 1H), 7.00 (dd, J=5.20 Hz, J=4.00 Hz, 1H), 4.72 (s, 2H).

Step 3: Synthesis of Compound BB-9-4

Compound BB-9-3 (1.6 g), dichloromethane (30 mL), di-tert-butyl carbonate (2.93 g), triethylamine (2.04 g) and 4-dimethylaminopyridine (328.52 mg) were added into a reaction flask, and then the reaction was carried out at 20° C. for 12 hours. The reaction solution was concentrated to obtain a crude product, and the crude product was separated and purified by silica gel column chromatography (eluent: petroleum ether:ethyl acetate=90:10 to 80:20) to obtain compound BB-9-4.

$^1$H NMR (400 MHz, $CDCl_3$) δ=7.96 (d, J=5.20 Hz, 1H), 7.69 (dd, J=4.80 Hz, J=4.20 Hz, 1H), 1.44 (s, 18H).

Step 4: Synthesis of Compound BB-9-5

Compound BB-9-4 (1.6 g), compound BB-1-3 (541.01 mg), N, N-dimethylformamide (3 mL), 1,1-bis (diphenylphosphine) ferrocene palladium chloride (267.15 mg) and cesium fluoride (1.66 g) were added into a reaction flask, and the reaction was carried out at 60° C. for 12 hours. Then saturated brine (30 mL), methyl tert-butyl ether (30 mL*3) were added for extraction, the organic phases were combined, concentrated to obtain a crude product, and the crude product was purified by silica gel column chromatography (eluent: petroleum ether:ethyl acetate=95:5 to 94:6) to obtain compound BB-9-5.

LCMS: m/z (ESI)=452.2[M+H]$^+$

Step 5: Synthesis of Compound BB-9

Compound BB-9-5 (1.1 g), methanol (5 mL), water (5 mL) and sodium hydroxide (194.93 mg) were added into a reaction flask and reacted at 25° C. for 1 h. The reaction solution was concentrated, the pH was adjusted to about 3 with 2M hydrochloric acid, and solids were precipitated. After filtration, the filter cake was concentrated to remove water and the compound BB-9 was obtained.

LCMS: m/z (ESI)=324.1[M+H]$^+$

Reference Embodiment 11: Synthesis of Intermediate BB-10

BB-10

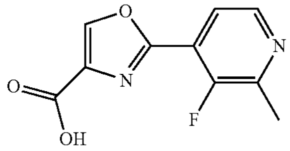

Synthetic Route:

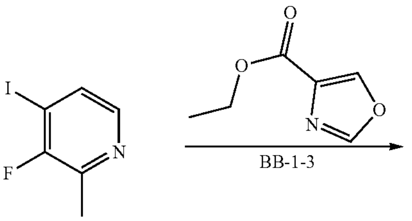

BB-1-3

BB-10-1

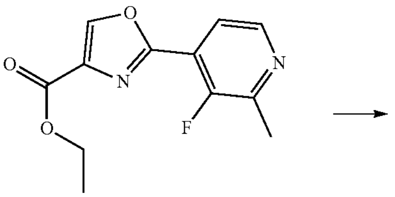

BB-10-2

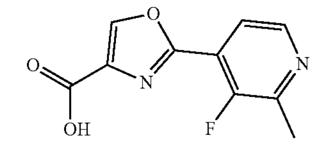

BB-10

Step 1: Synthesis of Compound BB-10-2

Compound BB-10-1 (1 g), compound BB-1-3 (1.16 g), N,N-dimethylformamide (10 mL), cesium carbonate (4.48 g) and 1,1-bis (diphenylphosphine) ferrocene palladium chloride (502.68 mg) were added into a reaction flask, and reacted at 60° C. for 12 h. The reaction solution was concentrated to obtain a crude product, and the crude product was separated and purified by silica gel column chromatography (eluent: petroleum ether:ethyl acetate=100:0 to 90:10) to obtain compound BB-10-2.

$^1H$ NMR (400 MHz, $CDCl_3$) δ=8.44-8.38 (m, 2H), 7.86 (t, J=5.20 Hz, 1H), 4.45 (d, J=7.20 Hz, 2H), 2.63 (d, J=3.20 Hz, 3H), 1.42 (t, J=7.20 Hz, 3H).

Step 2: Synthesis of Compound BB-10

Compound BB-10-2 (1 g), water (5 mL), ethanol (10 mL) and lithium hydroxide monohydrate (191.43 mg) were added into a reaction flask and react at 25° C. for 3 h; the reaction solution was concentrated to remove ethanol, and the pH was adjusted to 4 with 2 M hydrochloric acid, and solids were precipitated and the mixture was filtered, and the filter cake was concentrated to remove water to obtain compound BB-10.

$^1H$ NMR (400 MHz, DMSO-$d_6$) δ=9.02 (s, 1H), 8.46 (d, J=4.80 Hz, 1H), 7.83 (t, J=5.20 Hz, 1H), 2.55 (d, J=3.60 Hz, 3H).

Reference Embodiment 12: Synthesis of Intermediate BB-11

BB-11

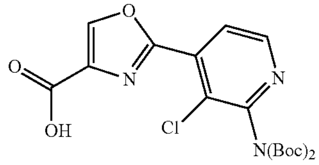

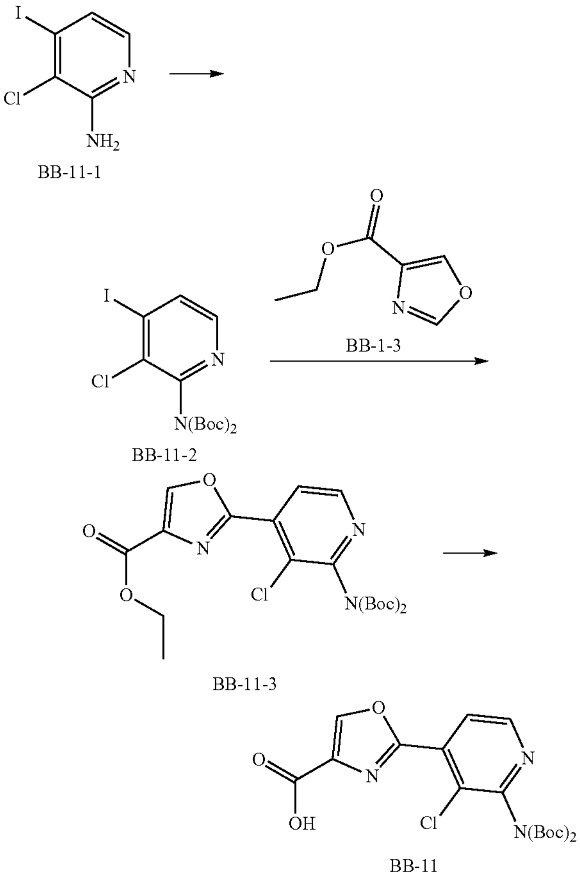

BB-11-1

BB-1-3

BB-11-2

BB-11-3

BB-11

Step 1: Synthesis of Compound BB-11-2

Compound BB-11-1 (1 g), dichloromethane (10 mL), di-tert-butyl carbonate (2.14 g), triethylamine (1.19 g) and 4-dimethylaminopyridine (96.02 mg) were added into a reaction flask, and then reacted at 20° C. for 12 hours. The reaction solution was concentrated to obtain a crude product, and the crude product was separated and purified by silica gel column chromatography (gradient eluent: petroleum ether:ethyl acetate=90:10 to 83:17) to obtain compound BB-11-2.

$^1H$ NMR (400 MHz, $CDCl_3$) δ=8.03 (d, J=5.20 Hz, 1H), 7.77 (d, J=5.20 Hz, 1H), 1.42 (s, 18H).

Step 2: Synthesis of Compound BB-11-3

Compound BB-11-2 (1.6 g), compound BB-1-3 (521.43 mg), N,N-dimethylformamide (16 mL), 1,1-bis (diphenylphosphine) ferrocene palladium chloride (257.48 mg) and cesium carbonate (3.44 g) were added into a reaction flask, and reacted at 60° C. for 12 h. Saturated brine (30 mL), methyl tert-butyl ether (30 mL*3) were added to the reaction solution for extraction, and the organic phases were combined and concentrated to obtain a crude product. The crude products were separated and purified by silica gel column chromatography (gradient eluent: petroleum ether:ethyl acetate=95:5 to 0:100) to obtain compound BB-11-3.

LCMS: m/z (ESI)=312.0[M+H−156]$^+$;

$^1H$ NMR (400 MHz, DMSO-$d_6$) δ=9.18 (s, 1H), 8.65 (d, J=5.20 Hz, 1H), 8.06 (d, J=5.20 Hz, 1H), 4.35 (t, J=7.20 Hz, 2H), 1.37-1.34 (m, 21H).

Step 3: Synthesis of Compound BB-11

Compound BB-11-3 (1 g), ethanol (5 mL), water (2.5 mL) and lithium hydroxide monohydrate (102.37 mg) were added to a reaction flask and reacted at 25° C. for 2.5 hours. The pH of the reaction solution was adjusted to 4 with 2M hydrochloric acid, and solids were precipitated, after filtration, the filter cake was dissolved with dichloromethane: methanol=8:1 (100 mL), then dried with anhydrous sodium sulfate, filtered, and the filtrate was concentrated to obtain compound BB-11.

LCMS: m/z (ESI)=340.1[M+H−100]$^+$ $^1H$ NMR (400 MHz, DMSO-$d_6$) δ=9.01 (s, 1H), 8.64 (d, J=5.20 Hz, 1H), 8.05 (d, J=5.20 Hz, 1H), 1.36 (s, 18H).

Reference Embodiment 13: Synthesis of Intermediate BB-12

BB-12

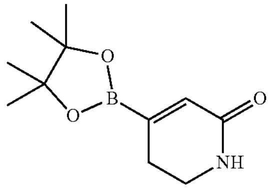

Synthetic Route:

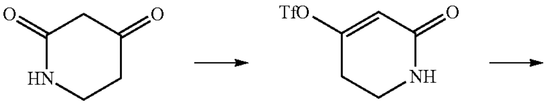

BB-12-1

BB-12-2

-continued

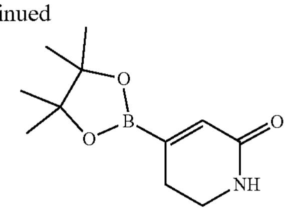

BB-12

Step 1: Synthesis of Compound BB-12-2

Compound BB-12-1 (5.0 g) was dissolved in tetrahydrofuran (50.0 mL), then triethylamine (8.95 g) was added, the temperature was reduced to 0° C., and a tetrahydrofuran (10.0 mL) solution of N-phenylbis (trifluoromethylsulfonyl) imine (18.95 g) was added, and the reaction solution was reacted at 25° C. for 16 hours. Saturated ammonium chloride (50.0 mL) was added to the reaction solution, and the mixture was extracted with ethyl acetate (50.0 mL*3), the organic phases were combined, dried with anhydrous sodium sulfate, filtered by suction and concentrated under reduced pressure, and the crude product was purified by column chromatography (eluent: petroleum ether:ethyl acetate=91:9 to 50:50) to obtain compound BB-12-2.

LCMS (ESI) m/z: 246.1[M+H]+

Step 2: Synthesis of Compound BB-12

Compound BB-12-2 (1 g) and bis(pinacolato)diboron (1.24 g) were added into a reaction flask and dissolved in 1,4-dioxane (30 mL), then 1,1-bis (diphenylphosphorus) ferrocene palladium chloride (596.88 mg) and potassium acetate (800.59 mg) were added, and the reaction was carried out at 70° C. for 1.5 hours. Water (50.0 mL) was added to the reaction solution, the mixture was extracted with ethyl acetate (50.0 mL*3), the organic phases were combined, dried with anhydrous sodium sulfate, filtered by suction and concentrated under reduced pressure to obtain the crude compound BB-12, which can be directly used in the next step.

Reference Embodiment 14: Synthesis of Intermediate BB-13

BB-13

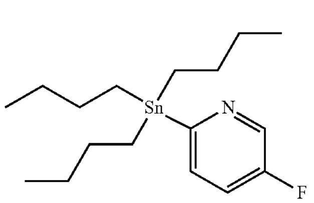

Synthetic Route:

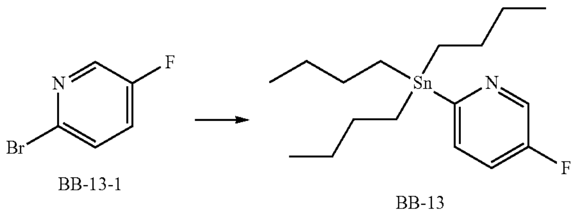 [SMILES: Fc1ccc(Br)nc1 ; CCC[CH2][Sn]([CH2]CCC)([CH2]CCC)[c]1ccc(F)cn1 ; "BB-13"]

BB-13-1 BB-13

Step 1: Synthesis of Compound BB-13

Compound BB-13-1 (5.0 g) and tetrahydrofuran (60 mL) were added into a reaction flask, the reaction system was replaced with nitrogen, and the temperature was lowered to −78° C., a solution of n-butyl lithium (2.5 M, 11.36 mL) in hexane was added while stirring, then tributyltin chloride (10.25 g) was added dropwise at −78° C., and the reaction was continued at −78° C. for 2 hours. Then the reaction solution was slowly poured into saturated ammonium chloride (100 mL), extracted with ethyl acetate (20 mL*3), the organic phases were combined, dried with anhydrous sodium sulfate, filtered by suction, concentrated under reduced pressure, and purified by column chromatography (eluent: petroleum ether:ethyl acetate=100:0 to 90:10) to obtain compound BB-13.

Embodiment 1: Synthesis of Compound WX001

WX001

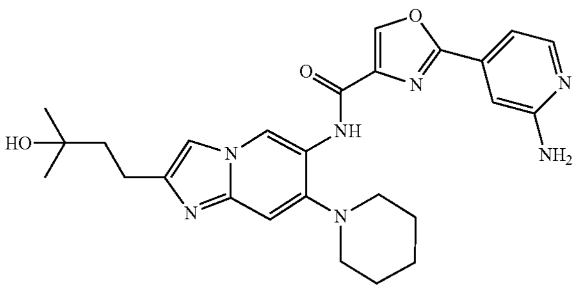

Synthetic Route:

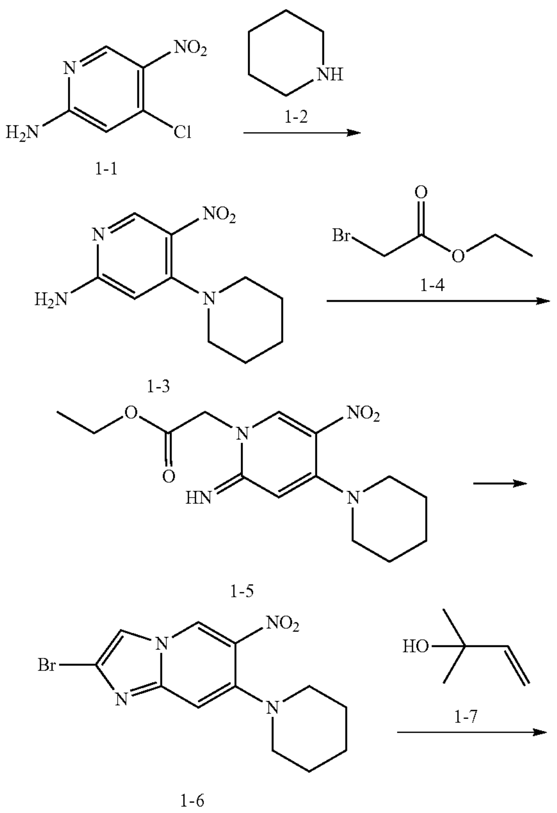

-continued

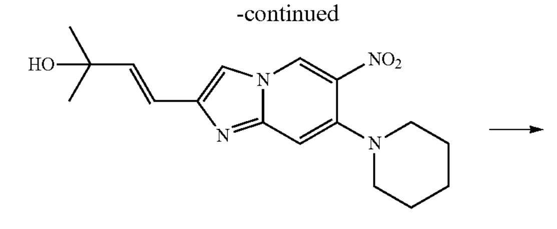

1-8

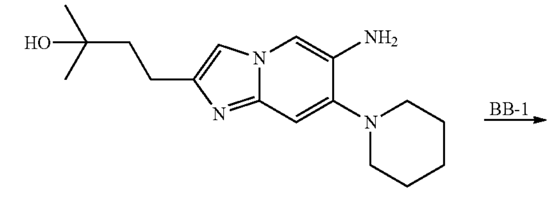

1-9

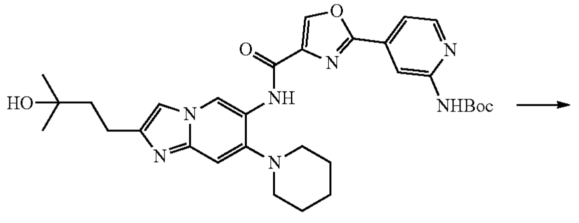

1-10

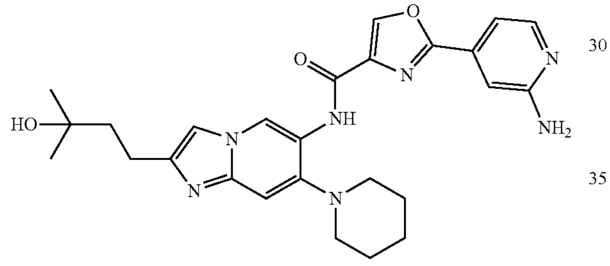

WX001

Step 1: Synthesis of Compound 1-3

Compound 1-1 (50 g) was dissolved in tetrahydrofuran (500 mL), compound 1-2 (122.65 g) was added, and the solution was stirred at 20° C. for 16 hours. The reaction solution was filtered, and the filtrate was concentrated to obtain a solid crude product. A mixed solvent of methyl tert-butyl ether and petroleum ether (1:1, 200 mL) was added to the crude product, then filtered after homogenized for 16 hours, and the solid was collected to obtain compounds 1-3.

$^1$H NMR (400 MHz, DMSO-$d_6$) δ=8.55 (s, 1H), 6.92 (s, 2H), 5.92 (s, 1H), 3.08-2.85 (m, 4H), 1.59 (d, J=4.0 Hz, 6H).

LCMS (ESI) m/z: 223.1[M+H]+

Step 2: Synthesis of Compound 1-5

Compound 1-4 (83.05 g) was added to compound 1-3 (11 g), and the obtained solution was stirred at 40° C. for 16 hours. The solution was filtered and the filter cake was washed twice with ethyl acetate (10 mL). The filter cake was collected and dried to obtain hydrobromide of compound 1-5.

LCMS (ESI) m/z: 309.2[M+H]+

Step 3: Synthesis of Compound 1-6

1,2-dichloromethane (150 mL) was added to the hydrobromide (10.5 g) of compound 1-5, and then phosphorus oxybromide (15.47 g) was added, and the obtained solution was stirred at 100-110° C. for 34 hours. Then phosphorus oxybromoxide (15.5 g) was added, and the solution was stirred at 110° C. for 36 hours. The solution was cooled to room temperature and then slowly poured into water (150 mL). After poured, 2 M sodium hydroxide aqueous solution was added dropwise to the quenched solution, so that the pH of the solution was about 10. Then dichloromethane (200 mL*3) was added for extraction, the organic phases were combined, saturated brine (200 mL) was added for washing, the organic phases were collected, dried with anhydrous sodium sulfate, filtered and concentrated, and the crude product was purified by column chromatography (eluent: petroleum ether:ethyl acetate=100:0 to 20:80) to obtain compound 1-6.

LCMS (ESI) m/z: 327.1[M+H]+

Step 4: Synthesis of Compound 1-8

Dioxane (10 mL) was added to compound 1-6 (0.8 g), then compound 1-7 (2.12 g), potassium carbonate (1.02 g), palladium dichloride (87.26 mg) and tricyclohexylphosphine (137.99 mg) were added, and the solution was stirred at 110° C. for 16 hours under nitrogen protection. The solution was filtered through diatomite, and the filter cake was washed twice with dichloromethane:methanol (1:1, 20 mL). The filtrate was collected and concentrated under reduced pressure to obtain a crude product, which was purified by column chromatography (eluent: dichloromethane/methanol=100:0 to 70:30) to obtain compound 1-8.

$^1$H NMR (400 MHz, $CD_3OD$) δ=9.39-9.30 (m, 1H), 7.92-7.80 (m, 1H), 7.04 (s, 1H), 6.71-6.58 (m, 2H), 3.27 (s, 4H), 2.00 (s, 1H), 1.74 (s, 6H), 1.40 (s, 6H).

LCMS (ESI) m/z: 331.3[M+H]+

Step 5: Synthesis of Compound 1-9

Methanol (100 mL) was added to compound 1-8 (650 mg), and wet palladium/carbon (50 mg, purity: 10%) was added under the micro nitrogen flow, and the solution was reacted at 25° C. for 16 hours under hydrogen (50 psi). The solution was filtered through diatomite, and the filter cake was washed with methanol (20 mL). The filtrate were combined and concentrated under reduced pressure to obtain compounds 1-9.

LCMS (ESI) m/z: 303.3[M+H]+

Step 6: Synthesis of Compound 1-10

Compound 1-9 (100 mg) was added to N,N-dimethylformamide (5 mL), and then compound BB-1 (106.00 mg), O-(7-azabenzotriazole-1-yl)-N,N,N,N-tetramethylurea hexafluorophosphate (188.60 mg) and triethylamine (100.38 mg) were added, and the mixture was stirred at 40° C. for 2 hours. After the solution was filtered, the crude product was separated and purified by preparative HPLC (column: Welch Xtimate C18 (100*40 mm*3 μm); mobile phase: [aqueous solution containing trifluoroacetic acid (0.075%)-acetonitrile]; gradient: acetonitrile %: 41%-71%, 8 min) to obtain trifluoroacetate of compound 1-10.

LCMS (ESI) m/z: 590.4[M+H]+

Step 7: Synthesis of Compound WX001

Dichloromethane (5 mL) was added to trifluoroacetate of compound 1-10 (5 mg), then trifluoroacetic acid (32.26 mg) was added, and the obtained mixture was stirred at 40° C. for 0.5 hours. The solution was concentrated under reduced pressure to remove the solvent, and acetonitrile (10 mL) and water (1 mL) were added for dissolution to obtain the trifluoroacetate of compound WX001.

$^1H$ NMR (400 MHz, $CD_3OD$) δ=9.58 (s, 1H), 8.90 (s, 1H), 8.08 (d, J=6.4 Hz, 1H), 7.86 (s, 1H), 7.59 (s, 1H), 7.45 (d, J=6.4 Hz, 1H), 7.36 (s, 1H), 3.17-3.12 (m, 4H), 2.98-2.91 (m, 2H), 1.99-1.89 (m, 6H), 1.78 (s, 2H), 1.30 (s, 6H).

LCMS (ESI) m/z: 490.4[M+H]+

Embodiment 2: Synthesis of Compound WX002

WX002

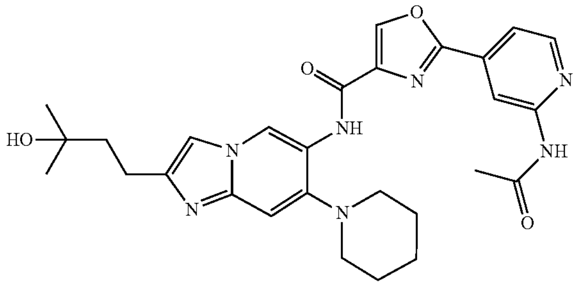

Synthetic Route:

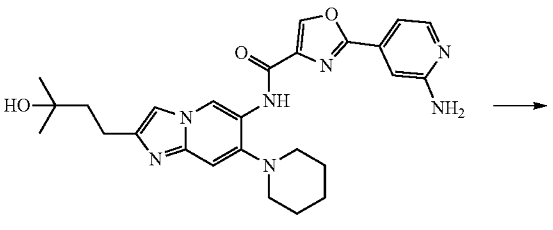

WX001

-continued

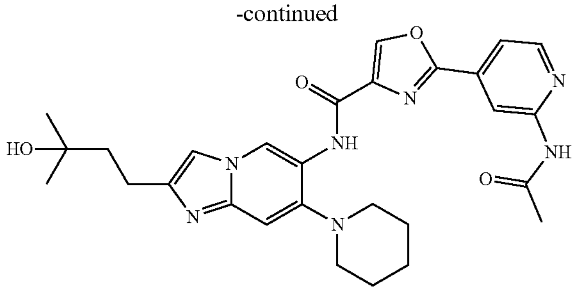

WX002

Step 1: Synthesis of Compound WX002

Dichloromethane (5 mL) was added to compound WX001 (40 mg), then acetic anhydride (43.60 mg) and triethylamine (82.68 mg) were added, and the obtained mixture was stirred at 20° C. for 16 hours, then the mixture was heated to 40° C. and stirred for 16 hours. 3 M aqueous sodium hydroxide solution (5 mL) was added to the reaction solution and stirred at 40° C. for 16 hours. After the reaction solution was concentrated, the crude product was separated and purified by preparative HPLC (column: Welch Xtimate C18 (100*40 mm*3 Wm); mobile phase: [aqueous solution containing trifluoroacetic acid (0.075%)-acetonitrile]; gradient: acetonitrile %: 27%-57%, 8 min) to obtain trifluoroacetate of compound WX002.

LCMS (ESI) m/z: 532.5 [M+H]+

Embodiment 3: Synthesis of Compound WX003

WX003

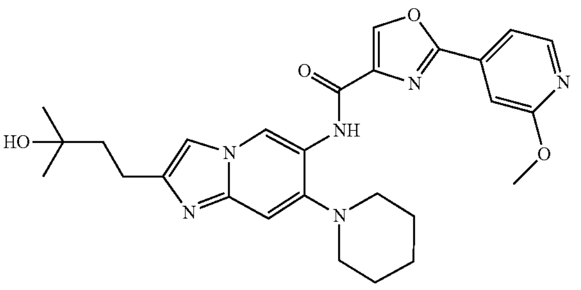

Synthetic Route:

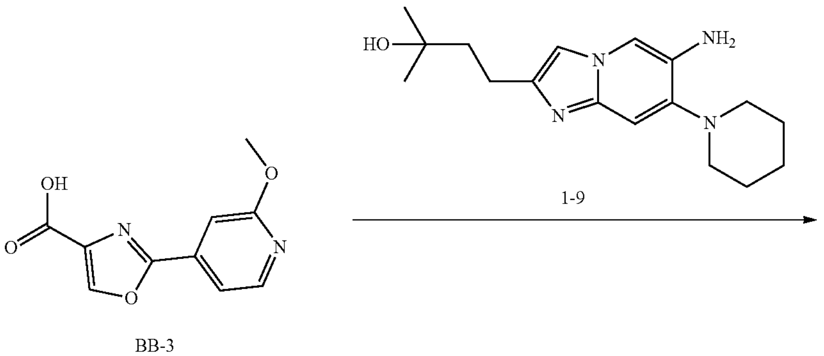

1-9

BB-3

-continued

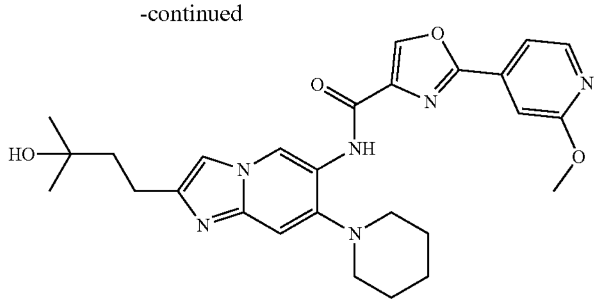

WX003

Step 1: Synthesis of Compound WX003

N,N-dimethylformamide (3 mL) was added to compound 1-9 (30 mg), and then compound BB-3 (32.76 mg), O-(7-azabenzotriazole-1-yl)-N,N,N,N-tetramethylurea hexafluorophosphate (56.58 mg) and N,N-diisopropylethylamine (25.64 mg) were added, and the mixture was stirred at 40° C. for 16 hours. The solution was filtered and directly separated and purified by preparative HPLC (column: Welch Xtimate C18 (100*40 mm*3 μm); mobile phase: [aqueous solution containing trifluoroacetic acid (0.075%)-acetonitrile]; gradient: acetonitrile %: 45%-67%, 8 min) to obtain trifluoroacetate of compound WX003.

$^{1}$H NMR (400 MHz, DMSO-$d_6$) δ=13.83 (s, 1H), 9.69 (s, 1H), 9.57 (s, 1H), 9.16 (s, 1H), 8.45 (d, J=5.2 Hz, 1H), 8.10 (s, 1H), 7.55 (d, J=4.4 Hz, 1H), 7.34 (s, 2H), 3.94 (s, 3H), 3.07 (s, 4H), 2.88-2.78 (m, 2H), 1.87 (s, 4H), 1.81-1.73 (m, 2H), 1.68 (s, 2H), 1.17 (s, 6H).

LCMS m/z: 505.3[M+H]+

Embodiment 4: Synthesis of Compound WX004

WX004

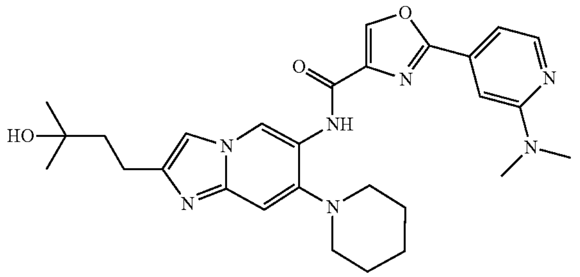

Synthetic Route:

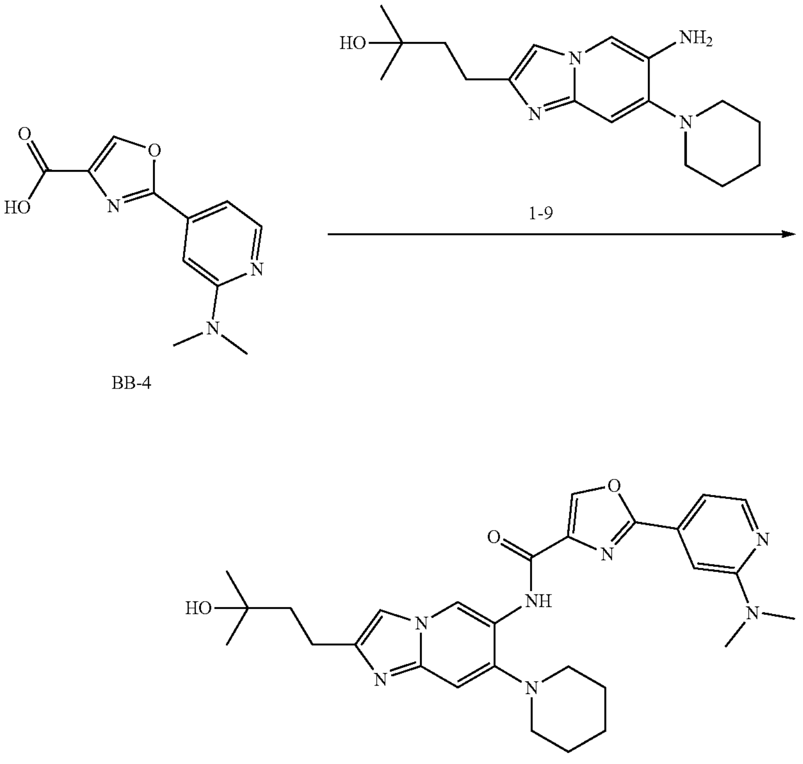

1-9

BB-4

WX004

Step 1: Synthesis of Compound WX004

N,N-dimethylformamide (5 mL) was added to compound 1-9 (30 mg) and then compound BB-4 (24.29 mg), O-(7-azabenzotriazole-1-yl)-N,N,N,N-tetramethylurea hexafluorophosphate (56.58 mg) and triethylamine (30.11 mg) were added, and the mixture was stirred at 40° C. for 16 hours. The reaction solution was directly purified by machine separation (column: Phenomenex Gemini-NX C18 (80*30 mm*3 μm); mobile phase: [aqueous solution containing ammonium bicarbonate (10 mM)-acetonitrile]; gradient B %: 48%-78%, 9 min), the fraction was concentrated and then separated and purified by preparative HPLC again (column: Welch Xtimate C18 (100*40 mm*3 m); mobile phase: [Aqueous solution containing trifluoroacetic acid (0.075%)-acetonitrile]; gradient: acetonitrile %: 41%-71%, 8 min) to obtain trifluoroacetate of compound WX004.

$^1$H NMR (400 MHz, $CD_3OD$) δ=9.64 (s, 1H), 8.85 (s, 1H), 8.20 (d, J=6.0 Hz, 1H), 7.87 (s, 1H), 7.59 (s, 1H), 7.41-7.35 (m, 2H), 3.31 (s, 6H), 3.19-3.09 (m, 4H), 3.01-2.88 (m, 2H), 2.09-1.88 (m, 6H), 1.77 (d, J=5.2 Hz, 2H), 1.30 (s, 6H).

LCMS m/z: 518.4[M+H]+

Embodiment 5: Synthesis of Compound WX005

WX005

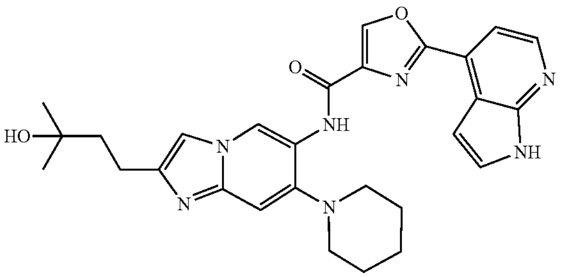

Synthetic Route:

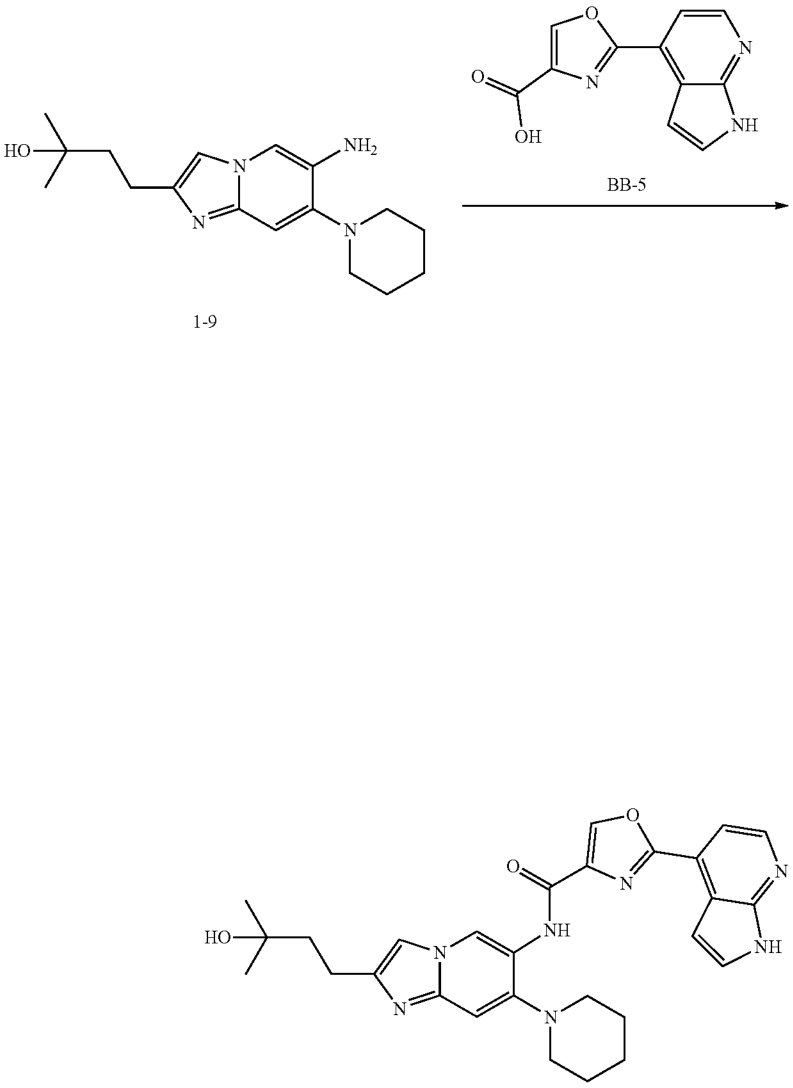

1-9

WX005

Step 1: Synthesis of Compound WX005

N,N-dimethylformamide (5 mL) and N,N-diisopropylethylamine (38.06 mg) were added to compound BB-5 (27 mg), and then O-(7-azabenzotriazole-1-yl)-N,N,N,N-tetramethylurea hexafluorophosphate (67.19 mg) was added. Finally, the mixed solution of compound 1-9 (35.63 mg) and N,N-dimethylformamide (0.5 mL) was added, and the solution was stirred at 30° C. for 1 hour. Ethyl acetate (10 mL) and saturated brine (10 mL) were added to the reaction solution, after separation, the organic phase was dried with anhydrous sodium sulfate and filtered, and after the solvent was concentrated under reduced pressure, the obtained crude product was separated and purified by preparative HPLC (column: Phenomenex Luna C18 (100*30 mm*5 μm); mobile phase: [aqueous solution containing hydrochloric acid (0.04%)-acetonitrile]; gradient: acetonitrile %: 10%-40%, 10 min) to obtain the hydrochloride of compound WX005.

$^1$H NMR (400 MHz, $CD_3OD$) δ=9.62 (s, 1H), 8.91 (s, 1H), 8.49 (d, J=4.8 Hz, 1H), 7.96 (d, J=5.6 Hz, 1H), 7.87 (s, 1H), 7.76 (d, J=3.2 Hz, 1H), 7.46 (d, J=2.8 Hz, 1H), 7.37 (s, 1H), 3.18-3.10 (m, 4H), 2.98-2.88 (m, 2H), 2.03-1.88 (m, 6H), 1.79-1.67 (m, 2H), 1.32-1.27 (s, 6H).

LCMS (ESI) m/z: 514.3[M+H]+

Embodiment 6: Synthesis of Compound WX006

WX006

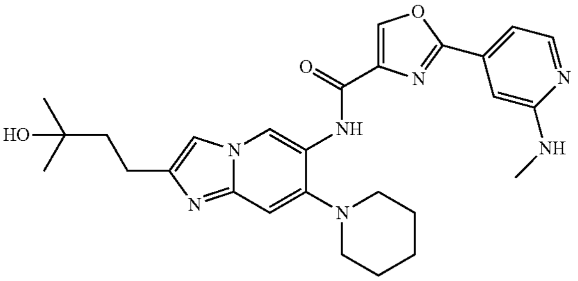

Synthetic Route:

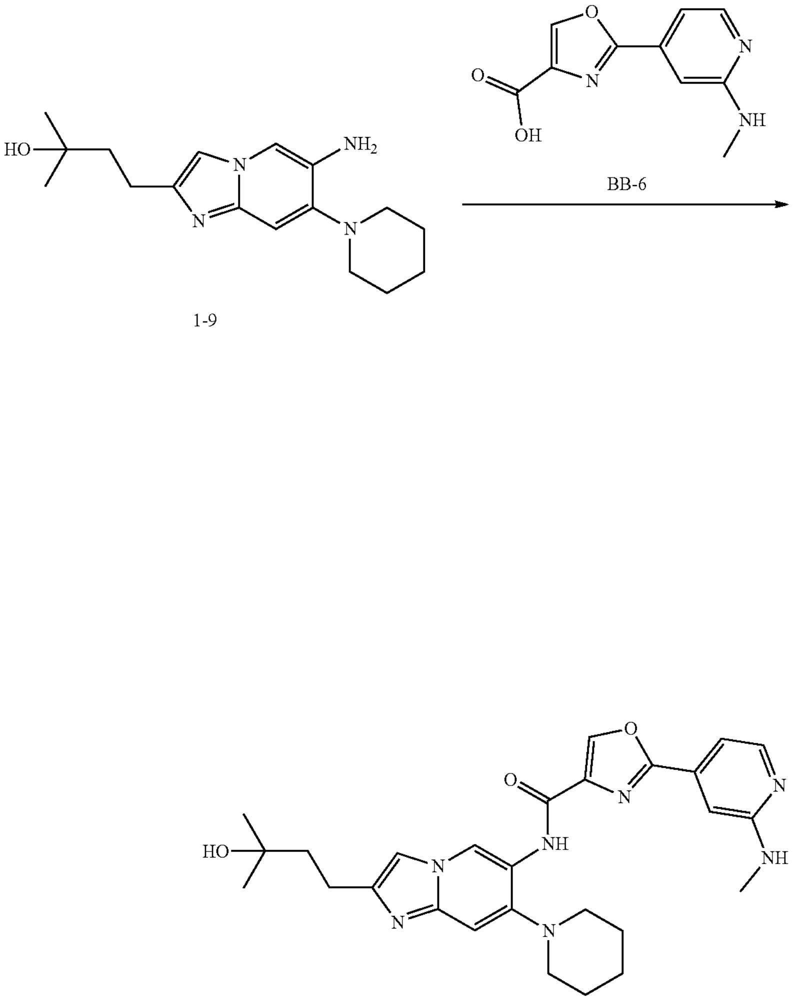

1-9

WX006

Step 1: Synthesis of Compound WX006

N,N-dimethylformamide (5 mL) was added to compound 1-9 (30 mg) and then compound BB-6 (23.92 mg), O-(7-azabenzotriazole-1-yl)-N,N,N,N-tetramethylurea hexafluorophosphate (56.58 mg) and triethylamine (72.70 mg) were added, and the mixture was stirred at 40° C. for 2 hours. After the solution was filtered, the crude product was directly separated and purified by preparative HPLC (column: Welch Xtimate C18 (100*40 mm*3 Wm); mobile phase: [aqueous solution containing trifluoroacetic acid (0.075%)-acetonitrile]; gradient: acetonitrile %: 17%-47%, 8 min) to obtain trifluoroacetate of compound WX006.

$^1$H NMR (400 MHz, DMSO-$d_6$) δ=9.66 (s, 1H), 9.59 (s, 1H), 9.17 (s, 1H), 8.22 (d, J=5.6 Hz, 1H), 8.12 (s, 1H), 7.36 (s, 1H), 7.18 (s, 1H), 7.15-7.09 (m, 1H), 3.09 (d, J=4.4 Hz, 4H), 2.90 (s, 3H), 2.87-2.80 (m, 2H), 2.68 (s, 1H), 2.34 (s, 1H), 1.87 (s, 4H), 1.82-1.74 (m, 2H), 1.69 (s, 2H), 1.19 (s, 6H).

LCMS (ESI) m/z: 504.4[M+H]+

Embodiment 7: Synthesis of Compound WX007

WX007

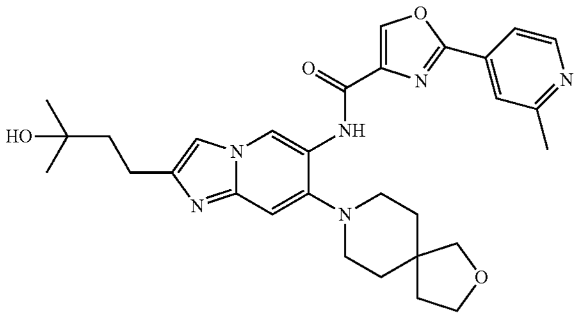

Synthetic Route:

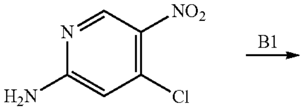

1-1

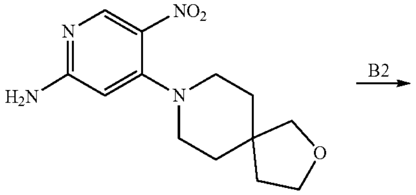

7-1

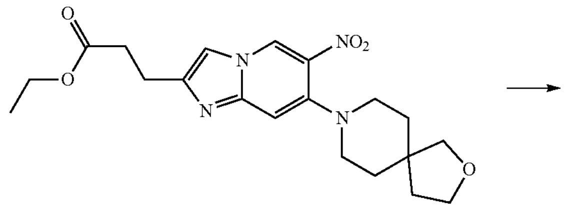

7-2

-continued

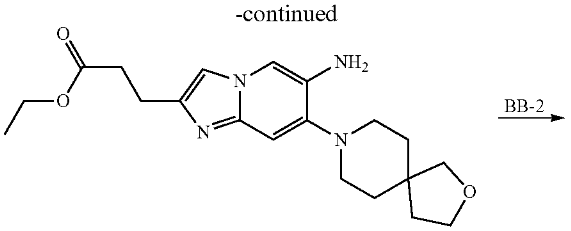

7-3

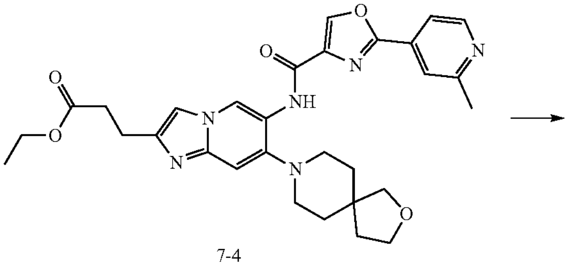

7-4

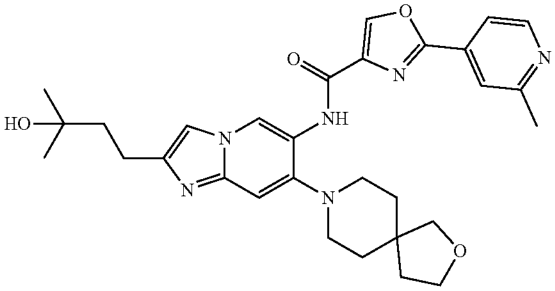

WX007

Step 1: Synthesis of Compound 7-1

Compound 1-1 (1.0 g) and compound B1 (1.1 g) were added to anhydrous ethanol (12.0 mL), then N,N-diisopropylethylamine (2.23 g) was added, and the solution was stirred at 90° C. for 16 hours. Ethyl acetate (80 mL) was added to the reaction solution for dilution, the organic phase was washed three times with saturated ammonium chloride aqueous solution (30 mL), and the organic phase was dried with anhydrous sodium sulfate, filtered and concentrated under reduced pressure to obtain compound 7-1.

$^1$H NMR (400 MHz, DMSO-$d_6$) δ=8.55 (s, 1H), 6.94 (s, 2H), 5.92 (s, 1H), 3.77-3.73 (m, 2H), 3.48 (s, 2H), 3.02-2.97 (m, 4H), 1.76-1.73 (s, 2H), 1.66-1.58 (m, 4H).

LCMS (ESI) m/z: 279.2[M+H]+

Step 2: Synthesis of Compound 7-2

Compound 7-1 (1.5 g) and sodium bicarbonate (1.1 g) were added to 1,4-dioxane (33.0 mL), and compound B2 (2.1 g) was added while stirring, and the reaction solution was stirred at 75° C. for 12 hours under nitrogen atmosphere. The solution was poured into saturated aqueous ammonium chloride solution (50.0 mL), extracted with ethyl acetate (30.0 mL*4), and the organic phases were combined and dried with anhydrous sodium sulfate, filtered and concentrated under reduced pressure, and the obtained crude product was purified by a silica gel plate (eluent: dichloromethane/methanol=20:1) to obtain compound 7-2.

LCMS (ESI) m/z: 403.3[M+H]+

Step 3: Synthesis of Compound 7-3

Wet Pd/C (0.3 g) was added into a dry hydrogenation bottle under argon protection, then ethanol (15.0 mL) was added and compound 7-2 (0.45 g) was added, and the reaction solution was reacted at 30° C. for 3 hours under the condition of hydrogen (50 psi). The solution was filtered through diatomite to remove the catalyst, and the filtrate was concentrated to dryness under reduced pressure to obtain compound 7-3.

LCMS (ESI) m/z: 373.3[M+H]+

Step 4: Synthesis of Compound 7-4

Compound 7-3 (200.0 mg), Compound BB-2 (131.5 mg), O-(7-azabenzotriazole-1-yl)-N,N,N,N-tetramethylurea hexafluorophosphate (408.3 mg) and N,N-diisopropylethylamine (173.5 mg) were added to N,N-dimethylformamide (3.0 mL) and the mixture was stirred at 25° C. for 12 hours. The solution was poured into saturated aqueous ammonium chloride solution (50.0 mL), extracted with dichloromethane (50.0 mL*3), and the organic phases were combined and dried with anhydrous sodium sulfate, filtered to remove desiccant, the filtrate was concentrated under reduced pressure to obtain crude product, and purified by preparative silica gel plate (eluent: dichloromethane/methanol=20:1) to obtain compound 7-4.

LCMS (ESI) m/z: 559.4[M+H]+

Step 5: Synthesis of Compound WX007

A solution of methyl magnesium chloride (3 M, 3.76 mL) in tetrahydrofuran was slowly added to anhydrous tetrahydrofuran (8.0 mL) at 0° C., and then a solution (2.0 mL) of compound 7-4 (90.0 mg) in anhydrous tetrahydrofuran was slowly added dropwise, and the solution was heated to 25° C. and stirred for 0.5 hour. The solution was poured into saturated aqueous ammonium chloride solution (50.0 mL), extracted with ethyl acetate (50.0 mL*3), and the organic phases were combined and dried with anhydrous sodium sulfate, filtered to remove desiccant, the filtrate was concentrated to obtain crude product, which was directly separated and purified by preparative HPLC (column: Waters Xbridge BEH C18 (100*25 mm*5 mu); mobile phase: [aqueous solution containing ammonium bicarbonate (10 mM)-acetonitrile]; gradient: acetonitrile %: 20%-60%, 10 min) to obtain compound WX007.

$^1H$ NMR (400 MHz, DMSO-$d_6$) δ=9.82 (s, 1H), 9.33 (s, 1H), 9.08 (s, 1H), 8.69 (s, 1H), 7.80 (s, 1H), 7.73 (s, 2H), 7.23 (s, 1H), 4.32 (s, 1H), 3.81-3.78 (m, 2H), 3.60 (s, 2H), 2.93-2.91 (m, 4H), 2.68-2.64 (m, 2H), 2.59 (s, 3H), 1.86-1.83 (m, 6H), 1.75-7.71 (m, 2H), 1.13 (s, 6H).

LCMS (ESI) m/z: 545.4[M+H]+.

Embodiment 8: Synthesis of Compound WX008

WX008

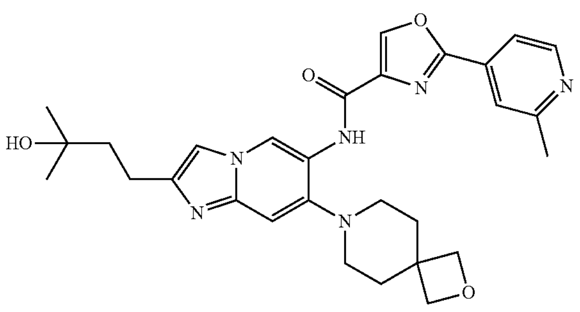

Synthetic Route:

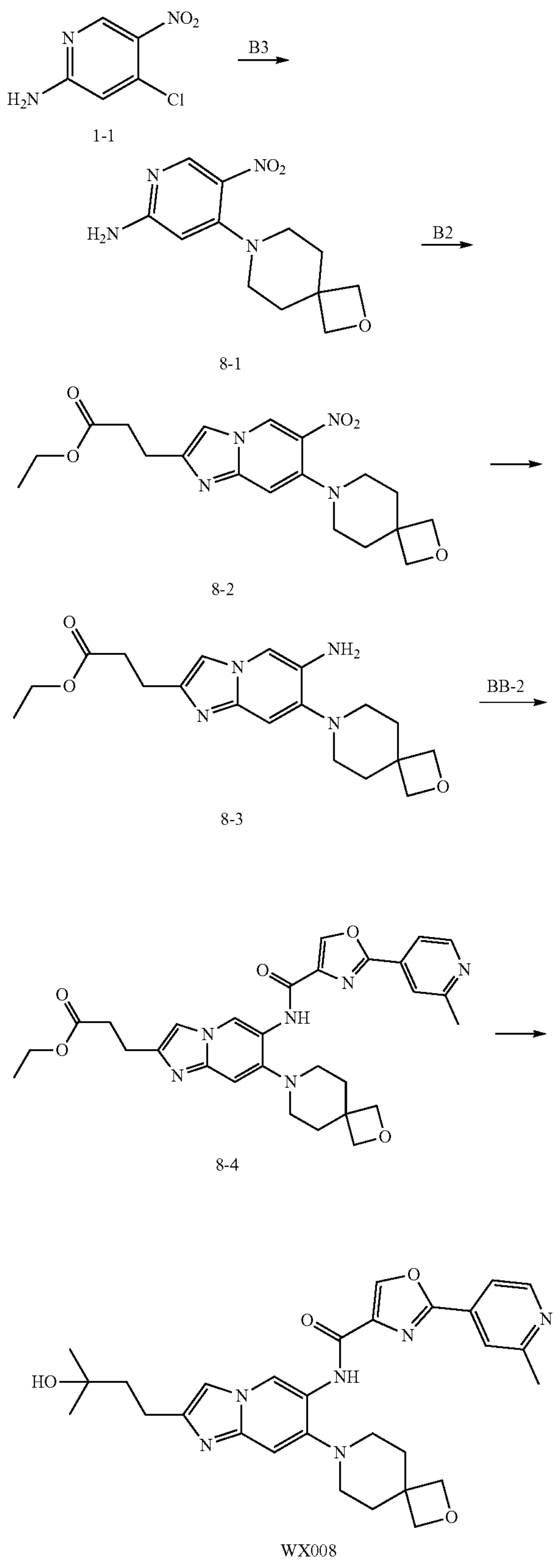

Step 1: Synthesis of Compound 8-1

Compound 1-1 (0.65 g) and compound B3 (500.14 mg) were added to anhydrous ethanol (7.5 mL), then N,N-diisopropylethylamine (1.45 g) was added, and the solution was stirred at 90° C. for 12 hours. After the reaction solution was concentrated under reduced pressure, the crude product was purified by column chromatography (eluent: petroleum ether/ethyl acetate=100:0 to 50:50) to obtain compound 8-1.

$^1$H NMR (400 MHz, DMSO-$d_6$) δ=8.57 (s, 1H), 6.96 (s, 2H), 5.92 (s, 1H), 4.35 (s, 4H), 2.93-2.90 (s, 4H), 1.92-1.9 (m, 4H).

LCMS (ESI) m/z: 265.2[M+H]+,

Step 2: Synthesis of Compound 8-2

Compound 8-1 (0.38 g) and sodium bicarbonate (289.91 mg) were added to 1,4-dioxane (8.0 mL), and compound B2 (577.33 mg) was added while stirring, and the solution was stirred at 75° C. for 12 hours after replacement of nitrogen. The solution was concentrated under reduced pressure, and the obtained crude product was purified by a silica gel plate (eluent: dichloromethane/methanol=20:1) to obtain compound 8-2.

LCMS (ESI) m/z: 389.2[M+H]+

Step 3: Synthesis of Compound 8-3

Raney nickel (13.23 mg) was added into a dry hydrogenation bottle under argon protection, then anhydrous ethanol (10.0 mL) and compound 8-2 (0.06 g) were added, and the solution was reacted at 30° C. for 3 hours under the condition of hydrogen (50 psi). The catalyst was removed by filtration, and the filtrate was concentrated to dryness under reduced pressure to obtain compound 8-3.

LCMS (ESI) m/z: 359.3[M+H]+

Step 4: Synthesis of Compound 8-4

Compound 8-3 (30 mg), Compound BB-2 (20.51 mg), O-(7-azabenzotriazole-1-yl)-N,N,N',N'-tetramethylurea hexafluorophosphate (47.74 mg) and N,N-diisopropylethylamine (21.63 mg) were added to N,N-dimethylformamide (2.0 mL) and the mixture was stirred at 25° C. for 12 hours. The solution was poured into saturated aqueous ammonium chloride solution (15.0 mL), extracted with ethyl acetate (20.0 mL*3), and the organic phases were combined and dried with anhydrous sodium sulfate, filtered to remove desiccant, and the filtrate was concentrated under reduced pressure to obtain crude product, which was purified by preparative silica gel plate (eluent: dichloromethane/methanol=20:1) to obtain compound 8-4.

LCMS (ESI) m/z: 545.3[M+H]+

Step 5: Synthesis of Compound WX008

A solution of methyl magnesium chloride (3 M, 244.83 μL) in tetrahydrofuran was slowly added to anhydrous tetrahydrofuran (2.0 mL) at 0° C., and then a solution (0.5 mL) of compound 8-4 (5 mg) in anhydrous tetrahydrofuran was slowly added dropwise, and the solution was heated to 10° C. and stirred for 0.5 hour. Then the solution was poured into saturated ammonium chloride aqueous solution (10.0 mL), extracted with ethyl acetate (20.0 mL*3), the organic phases were combined, dried with anhydrous sodium sulfate, filtered to remove the desiccant, the filtrate was concentrated under reduced pressure, and the obtained crude product was purified by preparative silica gel plate (eluent:

dichloromethane/methanol=20:1) to obtain compound WX008.

LCMS (ESI) m/z: 531.4[M+H]+

Embodiment 9: Synthesis of Compound WX009

WX009

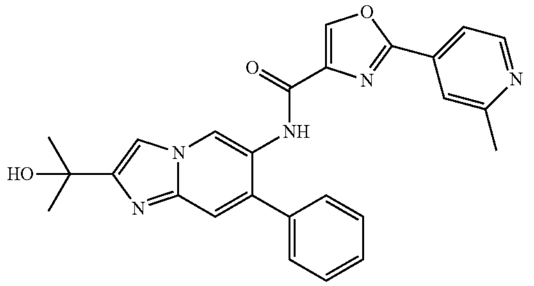

Synthetic Route:

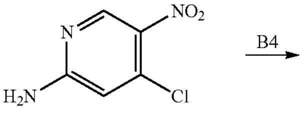

1-1

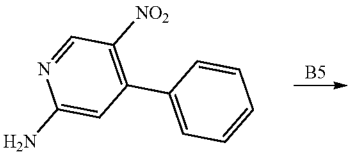

9-1

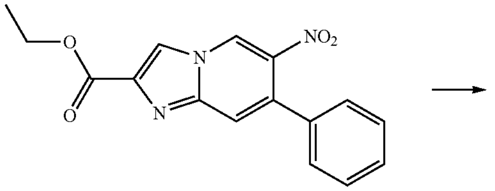

9-2

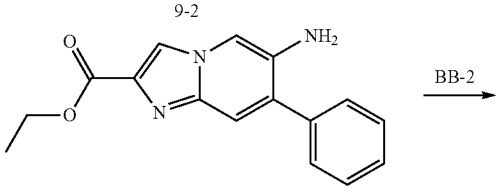

9-3

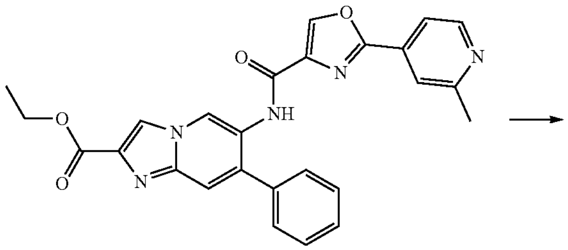

9-4

-continued

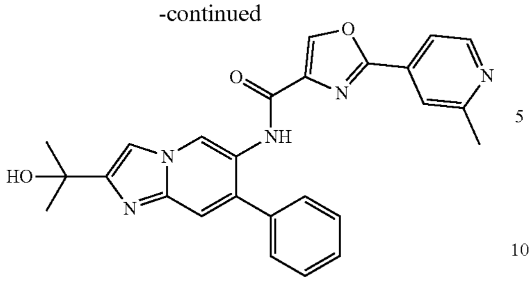

WX009

Step 1: Synthesis of Compound 9-1

Compound 1-1 (2.0 g), compound B4 (1.69 g) were dissolved in toluene (24.0 mL) and ethanol (6.0 mL), then tetrakis(triphenylphosphine)palladium (665.8 mg) and 1 M aqueous sodium carbonate (34.5 mL) were added. After the solution was stirred at 100° C. for 12 hours, ethyl acetate (100 mL) was added for dilution, after liquid separation, the obtained organic phase was washed twice with saturated ammonium chloride aqueous solution (50 mL). The organic phase was dried with anhydrous sodium sulfate and filtered, and the filtrate was concentrated under reduced pressure to obtain the crude product, which was purified by column chromatography (eluent: petroleum ether/ethyl acetate=80: 20 to 0:100) to obtain compound 9-1.

$^1$H NMR (400 MHz, DMSO-$d_6$) δ=8.81-8.74 (m, 1H), 7.43-7.29 (m, 7H), 6.40-6.31 (m, 1H).

Step 2: Synthesis of Compound 9-2

Compound 9-1 (2.0 g) and compound B5 (18.1 g) were added into a reaction flask, and the reaction solution was stirred at 90° C. for 12 hours under nitrogen atmosphere. The mixture of methyl tert-butyl ether/ethyl acetate (15:1, 15 mL) was poured into the reaction solution, stirred to precipitate the solid and filtered, and the filter cake was concentrated to dryness under reduced pressure to obtain compound 9-2.

$^1$H NMR (400 MHz, DMSO-$d_6$) δ=9.76 (s, 1H), 8.76 (s, 1H), 7.77 (s, 1H), 7.51-7.43 (m, 5H), 4.40-4.35 (m, 2H), 1.37-1.32 (m, 3H).

Step 3: Synthesis of Compound 9-3

Raney nickel (247.69 mg) was added into a dry hydrogenation bottle under argon protection, then anhydrous ethanol (10.0 mL) was added and compound 9-2 (0.9 g) was added, and the solution was reacted at 25° C. for 2 hours under the condition of hydrogen (50 psi). The solution was filtered through diatomite to remove the catalyst, and the filtrate was concentrated to dryness under reduced pressure to obtain compound 9-3.

LCMS (ESI) m/z: 282.1[M+H]+

Step 4: Synthesis of Compound 9-4

Compound 9-3 (0.5 g), Compound BB-2 (544.37 mg), O-(7-azabenzotriazole-1-yl)-N,N,N,N-tetramethylurea hexafluorophosphate (1.35 g) and N,N-diisopropylethylamine (574.29 mg) were added to N,N-dimethylformamide (10.0 mL) and the mixture was stirred at 25° C. for 12 hours. The solution was poured into saturated ammonium chloride aqueous solution (100 mL), extracted with dichloromethane (100 mL*3), the organic phases were combined and dried with anhydrous sodium sulfate, filtered to remove the desiccant, the filtrate was concentrated, and the obtained crude product was purified by preparative silica gel plate (eluent: dichloromethane/methanol=20:1) to obtain compound 9-4.

LCMS (ESI) m/z: 468.2[M+H]$^+$

Step 5: Synthesis of Compound WX009

A solution of methyl magnesium chloride in tetrahydrofuran (3 M, 5.13 mL) was slowly added to anhydrous tetrahydrofuran (5.0 mL) at 0° C., and then anhydrous tetrahydrofuran solution (5.0 mL) of compound 9-4 (90 mg) was slowly added dropwise, and the solution was heated to 25° C. and stirred for 0.5 hour. The reaction solution was poured into saturated ammonium chloride aqueous solution (50.0 mL), extracted with ethyl acetate (50.0 mL*3), the organic phases were combined and dried with anhydrous sodium sulfate, filtered to remove the desiccant, the filtrate was concentrated, and the crude product was purified by preparative silica gel plate (eluent: dichloromethane/methanol=15:1) to obtain compound WX009.

$^1$H NMR (400 MHz, DMSO-$d_6$) δ=9.72 (s, 1H), 9.00 (s, 1H), 8.92 (s, 1H), 8.68 (s, 1H), 7.86 (s, 1H), 7.72 (s, 1H), 7.66 (s, 1H), 7.56-7.48 (m, 6H), 5.08 (s, 1H), 2.59 (s, 3H), 1.51 (s, 6H).

LCMS (ESI) m/z: 454.2[M+H]$^+$

Embodiment 10: Synthesis of Compound WX010

WX010

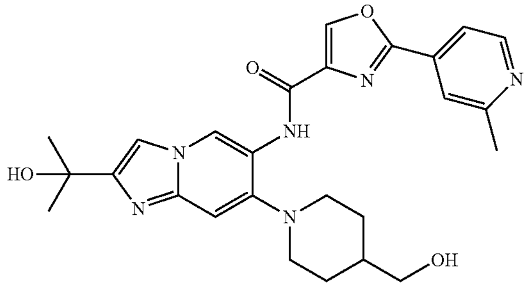

Synthetic Route:

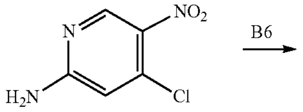

1-1

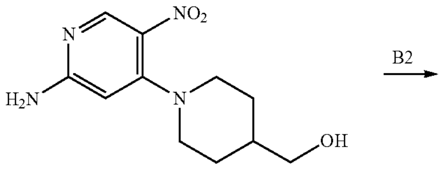

10-1

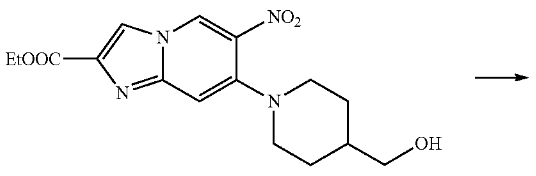

10-2

-continued

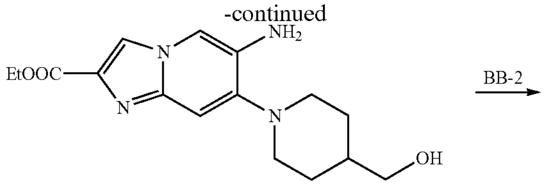

10-3

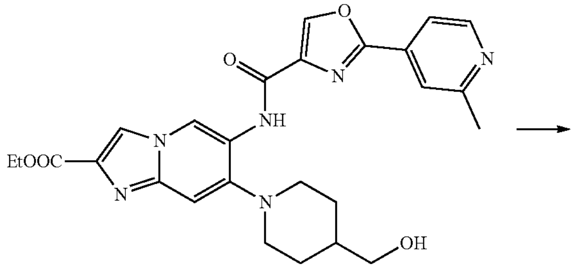

10-4

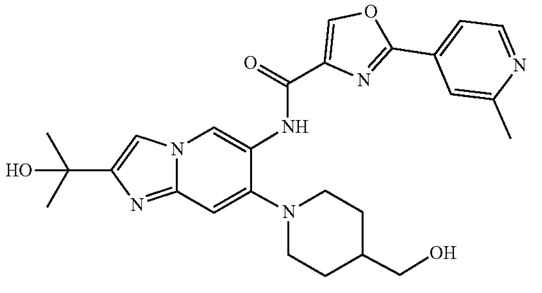

WX010

Step 1: Synthesis of Compound 10-1

Compound 1-1 (2.2 g) and compound B6 (1.53 g) were added to anhydrous ethanol (25.0 mL), then N,N-diisopropylethylamine (4.91 g) was added, and the reaction was carried out at 90° C. for 12 hours. After the reaction solution was concentrated under reduced pressure, the crude product was purified by column chromatography (eluent: petroleum ether/ethyl acetate=100:0 to 40:60) to obtain compound 10-1.

$^1$H NMR (400 MHz, DMSO-$d_6$) δ=8.60 (s, 1H), 6.97 (s, 2H), 5.98 (s, 1H), 4.59-4.57 (m, 1H), 3.37-3.34 (m, 2H), 3.29-3.23 (m, 2H), 2.86-2.80 (m, 2H), 1.78-1.75 (m, 2H), 1.37-1.31 (m, 2H).

Step 2: Synthesis of Compound 10-2

10-1 (1 g) and compound B2 (1.3 g) were dissolved in 1,4-dioxane (20.0 mL), sodium bicarbonate (333.00 mg) was added and the reaction system was replaced with nitrogen, and the reaction solution was reacted at 75° C. for 12 hours under nitrogen atmosphere. The solution was directly concentrated under reduced pressure, and the obtained crude product was purified by column chromatography (eluent: dichloromethane/methanol=100:0-99:1) to obtain compound 10-2.

$^1$H NMR (400 MHz, $CDCl_3$) δ=8.83 (s, 1H), 8.11 (s, 1H), 7.15 (s, 1H), 4.49-4.44 (m, 2H), 3.60-3.59 (m, 2H), 3.35-3.32 (m, 2H), 2.86-2.80 (m, 2H), 1.89-1.86 (m, 2H), 1.72 (s, 1H), 1.52-1.51 (m, 2H), 1.49-1.43 (m, 3H).

LCMS (ESI) m/z: 349.2[M+H]+

Step 3: Synthesis of Compound 10-3

Raney nickel (0.1 g) was added into a dry hydrogenation bottle under argon protection, then anhydrous ethanol (10.0 mL) and compound 10-2 (0.2 g) were added, and the solution was reacted at 35° C. for 3 hours under the condition of hydrogen (50 psi). The catalyst was removed by filtration, and the filtrate was concentrated to dryness under reduced pressure to obtain compound 10-3.

LCMS (ESI) m/z: 319.2[M+H]+

Step 4: Synthesis of Compound 10-4

Compound 10-3 (0.2 g), Compound BB-2 (128.27 mg), O-(7-azabenzotriazole-1-yl)-N,N,N',N'-tetramethylurea hexafluorophosphate (358.29 mg) and N,N-diisopropylethylamine (202.98 mg) were added to N,N-dimethylformamide (2.0 mL) and stirred at 35° C. for 12 hours. The reaction solution was poured into semi-saturated brine (20.0 mL), extracted with ethyl acetate (20 mL*3), and the organic phases were combined and dried with anhydrous sodium sulfate, filtered to remove desiccant, the filtrate was concentrated under reduced pressure to obtain crude product, which was purified by preparative silica gel plate (eluent: dichloromethane/methanol=20:1) to obtain compound 10-4.

$^1$H NMR (400 MHz, DMSO-$d_6$) δ=9.71 (s, 2H), 9.67 (s, 1H), 9.32 (s, 1H), 8.86 (s, 1H), 8.14-8.10 (m, 2H), 7.27 (s, 1H), 4.47-4.41 (m, 2H), 3.49-3.41 (m, 4H), 2.93-2.88 (m, 2H), 2.74 (s, 3H) 1.92-1.89 (m, 2H), 1.74-1.72 (m, 3H), 1.41-1.36 (m, 3H)

LCMS (ESI) m/z: 505.3[M+H]+

Step 5: Synthesis of Compound WX010

A solution of methyl magnesium chloride in tetrahydrofuran (3 M, 3.17 mL) was slowly added to anhydrous tetrahydrofuran (5.0 mL) at 0° C., and then a solution (2.0 mL) of compound 10-4 (0.04 g) in anhydrous tetrahydrofuran was slowly added dropwise, and the solution was stirred at 10° C. for 0.5 hour. The reaction solution was poured into saturated aqueous ammonium chloride solution (30.0 mL), then extracted with ethyl acetate (30.0 mL*3), and the organic phases were combined and dried with anhydrous sodium sulfate, filtered to remove desiccant, and the filtrate was concentrated under reduced pressure to obtain crude product, which was purified by preparative silica gel plate (eluent: dichloromethane/methanol=10:1) to obtain compound WX010.

LCMS (ESI) m/z: 491.4[M+H]+.

Embodiment 11: Synthesis of Compound WX011

WX011

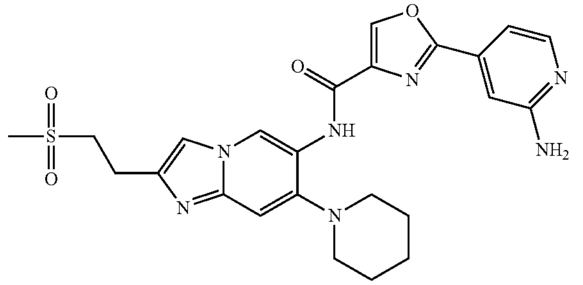

Synthetic Route:

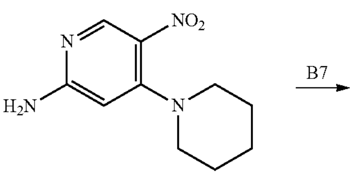

1-3

-continued

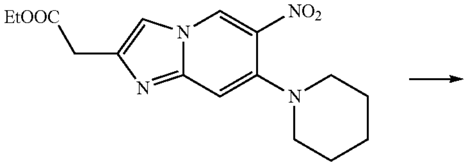

11-1

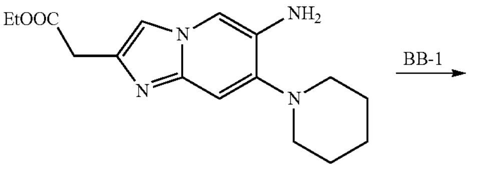

11-2

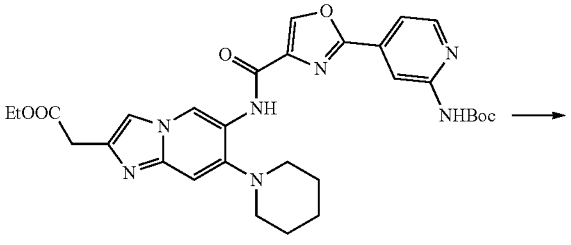

11-3

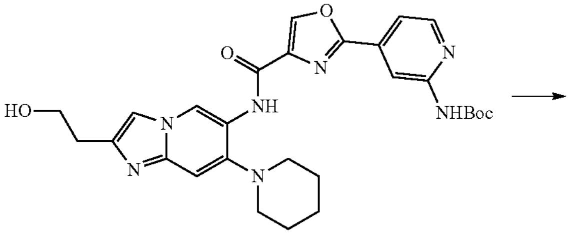

11-4

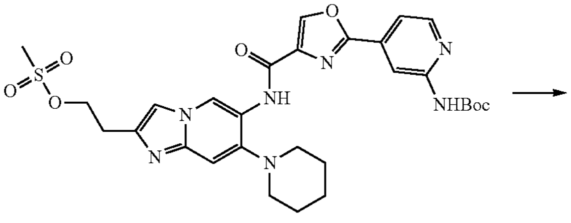

11-5

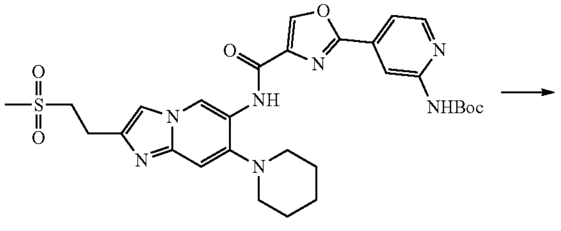

11-6

-continued

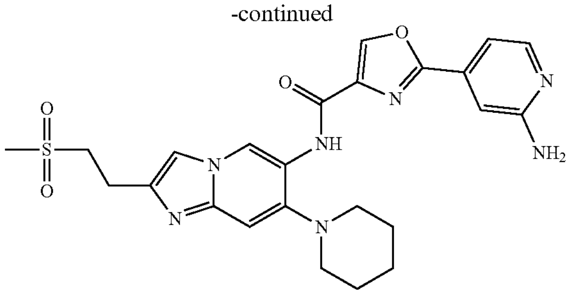

WX011

Step 1: Synthesis of Compound 11-1

Compound B7 (18.81 g) was added to compound 1-3 (10 g), and the obtained mixture was stirred at 90° C. for 2 hours. A mixture of dichloromethane and methanol (1:1, 100 mL) was added to the solution, and purified by column chromatography (eluent: dichloromethane/methanol=100:0 to 70:30) to obtain compound 11-1.

LCMS (ESI) m/z: 333.2[M+H]+

Step 2: Synthesis of Compound 11-2

Compound 11-1 (6.5 g) was dissolved in ethanol (300 mL), raney nickel (150 mg) was added, and the reaction solution was reacted at 50° C. under the condition of hydrogen (50 psi) for 16 hours. The solution was filtered through diatomite, the filtrate was collected, concentrated under reduced pressure, and purified (column: Welch Xtimate C18 (100*40 mm*3 Wm); mobile phase: [aqueous solution containing trifluoroacetic acid (0.075%)-acetonitrile]; gradient B %: acetonitrile %: 15%-45%, 8 min) to obtain trifluoroacetate of compound 11-2.

LCMS (ESI) m/z: 303.3[M+H]+

Step 3: Synthesis of Compound 11-3

N,N-dimethylformamide (20 mL) was added to trifluoroacetate (1.6 g) of compound 11-2, and then BB-1 (997.11 mg), O-(7-azabenzotriazole-1-yl)-N,N,N,N-tetramethylurea hexafluorophosphate (2.92 g) and potassium carbonate (1.59 g) were added. The mixture was stirred at 40° C. for 2 hours. Dichloromethane (50 mL) was added to the reaction solution, the mixture was washed with water (50 mL) for three times, and the organic phase was collected and dried with anhydrous sodium sulfate. The desiccant was removed by filtration, and the crude product obtained by filtration and concentration under reduced pressure was homogenized with methanol (5 mL) for 16 hours, and solids were precipitated. After filtration, the filter cake was collected and dried to obtain compound 11-3.

LCMS (ESI) m/z: 590.0[M+H]+

Step 4: Synthesis of Compound 11-4

Tetrahydrofuran (20 mL) was added to the compound 11-3 (550 mg), cooled to −20° C., and then a mixed solution of tetrahydroaluminum lithium (88.50 mg) in tetrahydrofuran (2 mL) was added dropwise, and the temperature of the obtained mixed solution was raised from −20° C. to 10° C., and the reaction was stirred at this temperature for 16 hours. Saturated potassium sodium tartrate solution (0.2 mL) was added dropwise to the reaction solution for quenching. After filtration with diatomite, the filter cake was washed with tetrahydrofuran (5 mL), and the filtrate was collected and dried with anhydrous sodium sulfate, filtered to remove desiccant, the obtain crude product through filtration and concentration under reduced pressure was purified by preparative silica gel plate (eluent: dichloromethane:methanol=10:1) to obtain compound 11-4.

$^{1}H$ NMR (400 MHz, $CDCl_3$) δ=9.87 (s, 1H), 9.39 (s, 1H), 8.71 (s, 1H), 8.45-8.36 (m, 2H), 7.57 (dd, J=1.6, Hz J=5.2 Hz, 1H), 7.52 (s, 1H), 7.35 (s, 1H), 7.21 (s, 1H), 4.00 (t, J=5.6 Hz, 2H), 3.71 (t, J=5.6 Hz, 1H), 3.03-2.89 (m, 6H), 2.18 (s, 2H), 2.04-1.94 (m, 4H), 1.57 (s, 9H).

LCMS (ESI) m/z: 548.0[M+H]+

Step 5: Synthesis of Compound 11-5

Chloroform (10 mL) and triethylamine (102.56 mg) were added to compound 11-4 (185 mg), the mixture of methane sulfonyl chloride (0.88 g) in chloroform (5 mL) was added dropwise at 0° C., and the obtained mixed solution was heated from 0° C. to 20° C. and stirred for 1 hour. The reaction solution was slowly added into stirred ice water (10 mL), dichloromethane (10 mL) was added and the reaction solution was extracted twice, then the organic phases were combined, dried with anhydrous sodium sulfate and filtered, and the filtrate was concentrated under reduced pressure to obtain crude product, which was purified by column chromatography (eluent: dichloromethane/methanol=100:0 to 80:20) to obtain compound 11-5.

LCMS (ESI) m/z: 626.3[M+H]+

Step 6: Synthesis of Compound 11-6

Compound 11-5 (35 mg) and sodium methyl sulfinate (11.42 mg) were dissolved in N,N-dimethylformamide (1 mL), and then potassium iodide (18.57 mg) was added. The reaction was carried out at 80° C. in a microwave apparatus for 1 hour. The solution was directly concentrated under reduced pressure to remove the solvent to obtain compound 11-6.

LCMS (ESI) m/z: 610.0[M+H]+

Step 7: Synthesis of Compound WX011

Dichloromethane (5 mL) was added to compound 11-6 (35 mg), and trifluoroacetic acid (65.45 mg) was added, and the obtained mixture was stirred at 40° C. for 2 hours. The solution was concentrated under reduced pressure to remove the solvent, and the obtained crude product was separated and purified by preparative HPLC (column: Welch Xtimate C18 (100*40 mm*3 m); mobile phase: [aqueous solution containing trifluoroacetic acid (0.075%)-acetonitrile]; gradient: acetonitrile %: 11%-41%, 8 min) to obtain trifluoroacetate of compound WX011.

LCMS (ESI) m/z: 510.2[M+H]+

Embodiment 12: Synthesis of Compound WX012

WX012

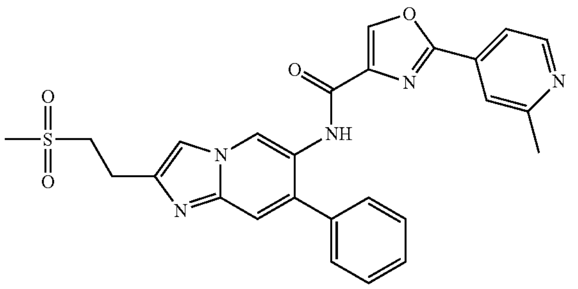

Synthetic Route:

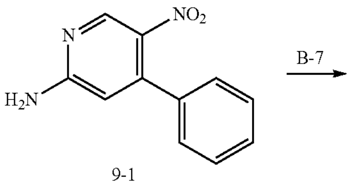

9-1

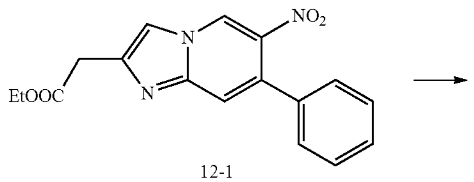

12-1

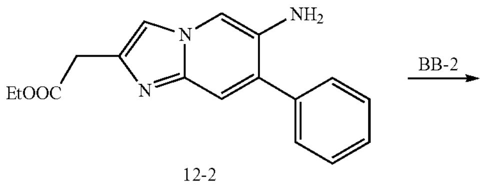

12-2

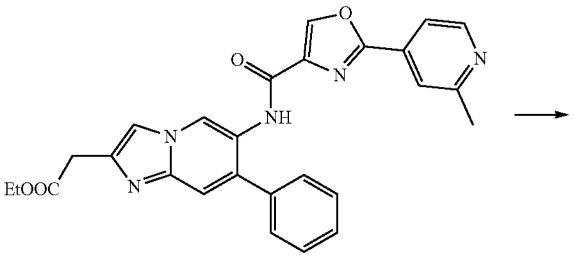

12-3

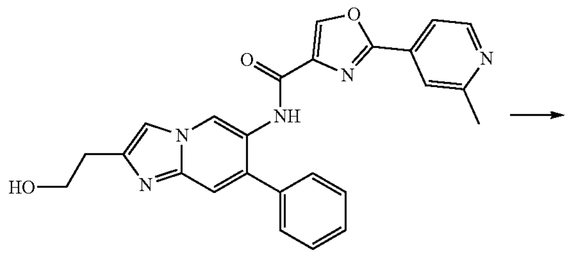

12-4

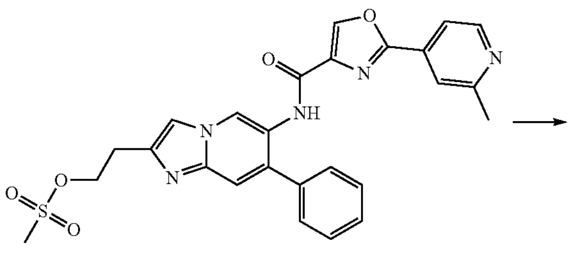

12-5

-continued

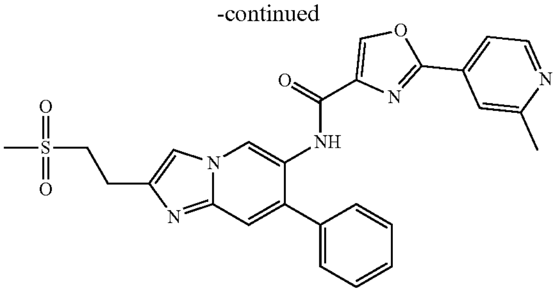

WX012

Step 1: Synthesis of Compound 12-1

Compound 9-1 (3.5 g) and compound B-7 (10.20 g) were added into a reaction flask, and the solution was reacted at 90° C. for 12 hours. Ethyl acetate (50 mL) was added to the reaction solution for dilution, and then it was poured into sodium bicarbonate aqueous solution (50 mL) for liquid separation. The aqueous phase was extracted with ethyl acetate (50 mL*3), and then the organic phases were combined, dried with anhydrous sodium sulfate, and filtered, the filtrate was concentrated under reduced pressure, and the crude product was purified by column chromatography (eluent: dichloromethane/methanol=100:0 to 99.5:0.5) to obtain compound 12-1.

LCMS (ESI) m/z: 326.2[M+H]$^+$.

Step 2: Synthesis of Compound 12-2

Palladium carbon (500 mg, purity: 10%) was added into a dry hydrogenation bottle under argon protection, then anhydrous ethanol (10.0 mL) and compound 12-1 (0.8 g) were added, and the reaction solution was reacted at 35° C. under hydrogen (50 psi) atmosphere for 3 hours. The catalyst was removed by filtration, and the filtrate was concentrated to dryness under reduced pressure to obtain compound 12-2.

LCMS (ESI) m/z: 296.2[M+H]$^+$.

Step 3: Synthesis of Compound 12-3

Compound 12-2 (0.7 g) and compound BB-2 (580.74 mg) were added to N,N-dimethylformamide (15.0 mL), then O-(7-azabenzotriazole-1-yl)-N,N,N',N'-tetramethylurea hexafluorophosphate (1.35 g) and N,N-diisopropylethylamine (612.66 mg) were added, and the mixture was stirred at 25° C. for 12 hours. The solution was poured into semi-saturated brine (50.0 mL) and extracted with ethyl acetate (30 mL*3). The combined organic phases were dried with anhydrous sodium sulfate, filtered, concentrated under reduced pressure to obtain crude product, and purified by column chromatography (eluent: dichloromethane/methanol=100:0 to 99:1) to obtain compound 12-3.

LCMS (ESI) m/z: 482.3[M+H]$^+$.

Step 4: Synthesis of Compound 12-4

Compound 12-3 (200 mg) was dissolved in tetrahydrofuran (10 mL), then the temperature was lowered to −10° C., and then lithium aluminum tetrahydro (15.76 mg) was added, and the reaction was carried out for 1 hour. Saturated potassium sodium tartrate solution (0.3 mL) was added dropwise into the reaction solution, stirred for 5 minutes, then dried with anhydrous sodium sulfate, and filtered, the filtrate was concentrated under reduced pressure to obtain crude product, which was purified by column chromatography (eluent: dichloromethane/methanol=100:0 to 97.5:2.5) to obtain compound 12-4.

LCMS (ESI) m/z: 440.3[M+H]$^+$.

Step 5: Synthesis of Compound 12-5

Compound 12-4 (40 mg) was added to chloroform (2.0 mL), then triethylamine (27.63 mg) was added. After cooled to 10° C., a solution of methanesulfonyl chloride (15.64 mg) in chloroform (0.5 mL) was added, and then the temperature was raised to 25° C. and the reaction was carried out for 20 minutes. The reaction solution was poured into water (10.0 mL) and then separated. The aqueous phase was extracted with dichloromethane (10 mL*3), the organic phases were combined, dried and filtered with anhydrous sodium sulfate, and the filtrate was concentrated under reduced pressure to obtain compound 12-5.

LCMS (ESI) m/z: 518.3[M+H]$^+$.

Step 6: Synthesis of Compound WX012

Compound 12-5 (30 mg) and sodium methyl sulfite salt (10.65 mg) were added into N,N-dimethylformamide (2.0 mL), then potassium iodide (28.87 mg) was added, and the reaction was carried out under microwave at 80° C. for 1 hour. The reaction solution was diluted with ethyl acetate (10.0 mL), then poured into semi-saturated brine solution (30.0 mL). After liquid separation, the aqueous phase was extracted with ethyl acetate (30 ml*4), then the organic phases were combined, dried with anhydrous sodium sulfate, filtered and concentrated under reduced pressure, and the crude product was directly separated and purified by preparative HPLC (column: Phenomenex Gemini-NX C18 (75*30 mm*3 μm); mobile phase: [aqueous solution containing ammonium bicarbonate (10 mM)-acetonitrile]; gradient: acetonitrile %: 25%-45%, 8 min) to obtain compound WX012.

$^1$H NMR (400 MHz, DMSO-$d_6$) δ=9.06 (s, 1H), 8.94 (s, 1H), 8.67 (s, 1H), 7.95 (s, 1H), 7.72 (s, 1H), 7.66-7.64 (m, 1H), 7.58-7.49 (m, 6H), 3.56-3.53 (m, 2H), 3.19-3.16 (m, 2H), 3.04 (m, 3H), 2.60 (s, 3H).

Embodiment 13: Synthesis of Compound WX013

WX013

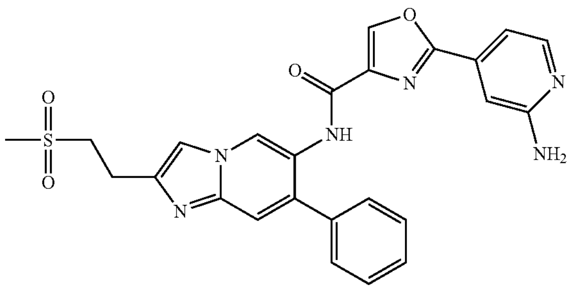

Synthetic Route:

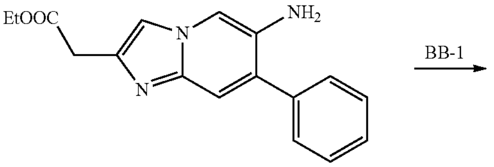

12-2

-continued

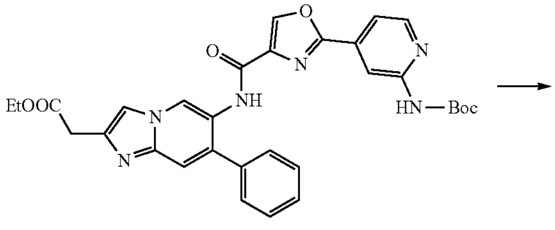

13-1

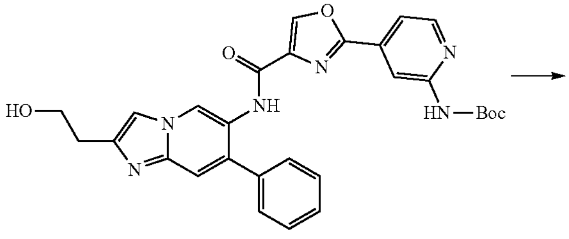

13-2

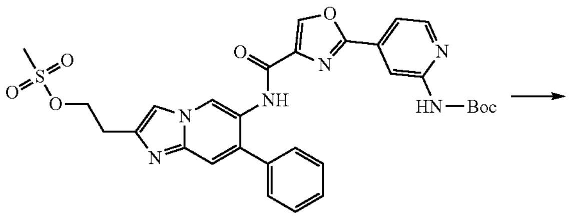

13-3

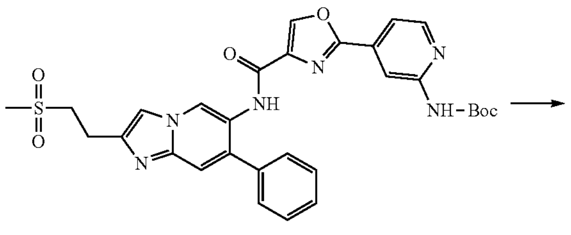

13-4

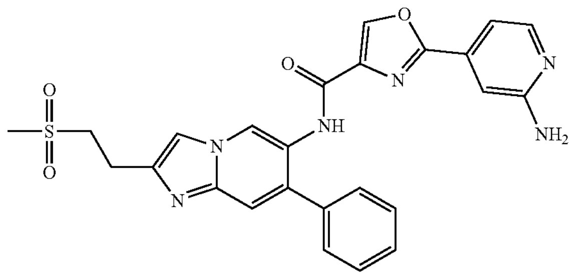

WX013

Step 1: Synthesis of Compound 13-1

Compound BB-1 (659.50 mg) and N, N-dimethylformamide (10 mL) were added in a pre-dried single-mouth bottle, then diisopropylethylamine (558.40 mg) was added, and then O-(7-azabenzotriazole-1-yl)-N, N, N, N-tetramethylurea hexafluorophosphine salt was added, and the reaction was carried out at 20° C. for 0.5 hour. Compound 12-2 (638 mg) was added and the reaction was stirred at 20° C. for 15.5 hours. Ethyl acetate (10 mL) and saturated brine (10 mL) were added to the reaction solution, and then separated. The organic phase was dried with anhydrous sodium sulfate, filtered, concentrated under reduced pressure, and the crude product was purified by column chromatography (eluent: dichloromethane/methanol=100:0 to 50:50), methanol (1 mL) and ethyl acetate (5 mL) were added to the product obtained after concentrating the fraction, then the mixture was ultrasonated for 5 minutes and filtered, and the filter cake was collected to obtain compound 13-1.

$^1$H NMR (400 MHz, DMSO-$d_6$) δ=10.14 (s, 1H), 9.75 (s, 1H), 9.05 (s, 1H), 8.91 (s, 1H), 8.45 (d, J=5.2 Hz, 1H), 8.41 (s, 1H), 7.96 (s, 1H), 7.60-7.40 (m, 7H), 3.82 (s, 2H), 3.32-3.16 (m, 2H), 1.50 (s, 9H), 1.07-1.04 (m, 3H).

LCMS (ESI) m/z: 583.4 $[M+H]^+$

Step 2: Synthesis of Compound 13-2

Compound 13-1 (460 mg) and anhydrous tetrahydrofuran (10 mL) were added to a pre-dried single-mouth bottle, and lithium aluminum tetrahydro (37.46 mg) was added under ice bath at 0° C., and the reaction solution was stirred at 0° C. for 0.5 hour. Water (2.0 mL) was slowly added into the reaction solution to quench the reaction, then ethyl acetate (5.0 mL) was added after quenching, and the filter cake after filtration was rinsed with mixed solvent of dichloromethane/methanol (1:1, 10.0 mL); the filtrate was washed with saturated brine (5.0 mL) and separated, and the obtained organic phase was mixed with the previous mixed solvent, dried with anhydrous sodium sulfate and filtered, and the filtrate was concentrated under reduced pressure to obtain a crude product, which was purified by column chromatography (eluent: dichloromethane/methanol=100:0 to 95:5) to obtain compound 13-2.

$^1$H NMR (400 MHz, DMSO-$d_6$) δ=10.16 (s, 1H), 9.74 (s, 1H), 8.99 (s, 1H), 8.91 (s, 1H), 8.47-8.43 (m, 1H), 8.41 (s, 1H), 7.84 (s, 1H), 7.59-7.39 (m, 7H), 4.73-4.67 (m, 1H), 3.79-3.70 (m, 2H), 2.83-2.90 (m, 2H), 1.51 (s, 9H)

LCMS (ESI) m/z: 541.4 $[M+H]^+$

Step 3: Synthesis of Compound 13-3

Compound 13-2 (50 mg) was added to chloroform (2.0 mL), triethylamine (46.26 mg) was added, the temperature was lowered to 0° C. and then the mixture was stirred for 10 minutes, then a solution (1.0 mL) of methanesulfonyl chloride (63.58 mg) in chloroform was slowly added, and the temperature was raised to 20° C. and the reaction was carried out for 13 hours and 50 minutes. Saturated aqueous ammonium chloride solution (5.0 mL) was added to the reaction solution, and the mixture was extracted and separated, the organic phase was washed with 5 M citric acid aqueous solution (5.0 mL), separated, washed with water (5.0 mL), separated, the organic phase was collected, dried with anhydrous sodium sulfate, and filtered, and the filtrate was concentrated under reduced pressure to dryness to obtain compound 13-3.

$^1$H NMR (400 MHz, $CDCl_3$) δ=9.85 (s, 1H), 9.29 (s, 1H), 8.44 (s, 1H), 8.40-8.35 (m, 2H), 7.83-7.69 (m, 3H), 7.65 (s, 1H), 7.57-7.52 (m, 2H), 7.36-7.30 (m, 2H), 4.88-4.73 (m, 2H), 3.53-3.44 (m, 2H), 3.14 (s, 3H), 1.62 (S, 9H).

LCMS (ESI) m/z: 619.4 $[M+H]^+$

Step 4: Synthesis of Compound 13-4

Compound 13-3 (35 mg), potassium iodide (28.17 mg) and sodium methyl sulfinate (16.18 mg) were added into a pre-dried reaction flask, then N,N-dimethylformamide (2.0 mL) was added and the mixture was stirred at 80° C. for 16 hours under oil bath. Ethyl acetate (10 mL) and saturated brine (10 mL) were added to the reaction solution, after liquid separation, the aqueous phase was extracted with a mixed solution (5.0 mL*3) of dichloromethane/methanol (10:1), after liquid separation, the organic phases were combined, dried with anhydrous sodium sulfate, filtrated, and the solvent was concentrated under reduced pressure to dryness. The residue was purified by column chromatography (eluent: dichloromethane/methanol=100:0 to 95:5) to obtain compound 13-4.

$^1$H NMR (400 MHz, DMSO-$d_6$) δ=10.15 (s, 1H), 9.74 (s, 1H), 9.05 (s, 1H), 8.91 (s, 1H), 8.45 (d, J=4.8 Hz, 1H), 8.41 (s, 1H), 7.93 (s, 1H), 7.60-7.40 (m, 7H), 3.54 (m, 2H), 3.21-3.13 (m, 2H), 3.03 (s, 3H), 1.52 (s, 9H)

LCMS (ESI) m/z: 603.4 $[M+H]^+$

Step 5: Synthesis of Compound WX013

Compound 13-4 (20 mg) was added into a pre-dried single-mouth bottle, hydrochloric acid/methanol (4 M, 16.67 mL) was added, and the solvent was distilled under reduced pressure at 40° C. to dryness, and the above operations were repeated to obtain the hydrochloride of compound WX013.

$^1$H NMR (400 MHz, DMSO-$d_6$) δ=9.96 (s, 1H), 9.37-9.28 (m, 1H), 9.02 (s, 1H), 8.24-8.18 (m, 1H), 8.13 (d, J=6.4 Hz, 2H), 7.90-7.81 (m, 1H), 7.65-7.50 (m, 6H), 7.34-7.24 (m, 1H), 7.14-7.06 (m, 1H), 3.65-3.56 (m, 2H), 3.35-3.28 (m, 2H), 3.08 (s, 3H).

LCMS (ESI) m/z: 503.3 $[M+H]^+$

Embodiment 14: Synthesis of Compound WX014

WX014

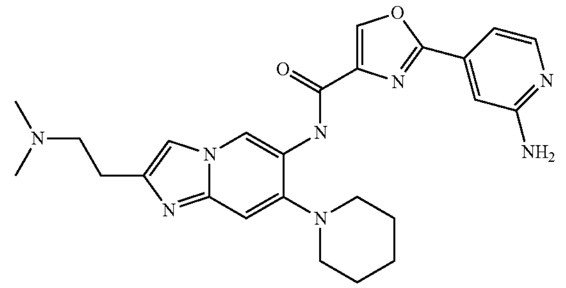

Synthetic Route:

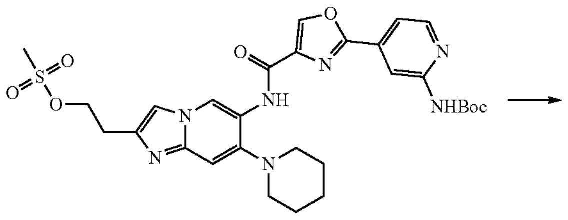

11-5

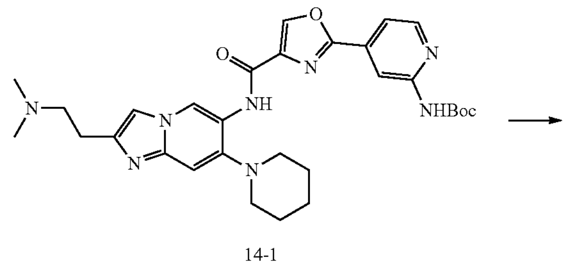

14-1

-continued

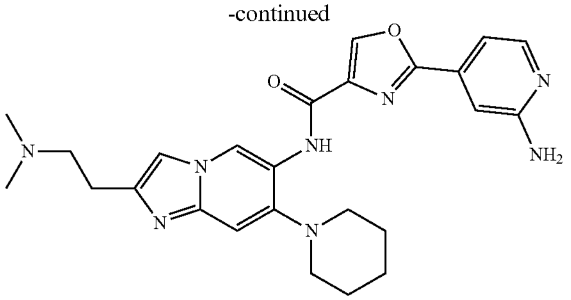

WX014

Step 1: Synthesis of Compound 14-1

Compound 11-5 (40 mg), dimethylamine aqueous solution (14.41 mg, purity: 40%) were added to 1,4-dioxane (5 mL), then potassium iodide (21.22 mg) and triethylamine (19.41 mg) were added, and the reaction solution was stirred at 80° C. for 5 hours. After the reaction solution was filtered, the filtrate was collected and concentrated directly under reduced pressure to obtain compound 14-1.

LCMS (ESI) m/z: 575.1[M+H]+

Step 2: Synthesis of Compound WX014

Dichloromethane (10 mL) and trifluoroacetic acid (79.36 mg) were added to compound 14-1 (40 mg), and the obtained mixture was stirred at 40° C. for 1 hour. After concentrated under reduce pressure, the crude product was separated and purified by preparative HPLC (column: Welch Xtimate C18 (100*40 mm*3 Wm); mobile phase: [aqueous solution containing trifluoroacetic acid (0.075%))-acetonitrile]; gradient: acetonitrile %: 5%-36%, 8 min) to obtain trifluoroacetate of compound WX014.

LCMS (ESI) m/z: 475.4[M+H]+

Embodiment 15: Synthesis of Compound WX015

WX015

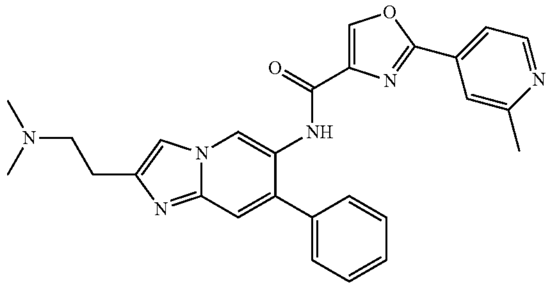

Synthetic Route:

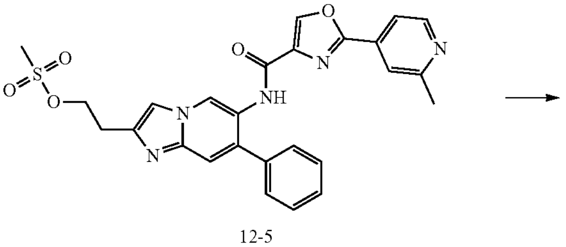

12-5

-continued

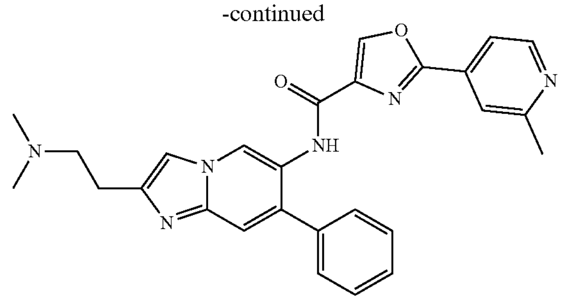

WX015

Step 1: Synthesis of Compound WX015

Compound 12-5 (25 mg), dimethylamine aqueous solution (27.22 mg, purity: 40%) were added to dioxane (2.0 mL), then potassium iodide (24.06 mg) was added, and the reaction was carried out at 90° C. for 12 hours. Then the reaction solution was poured into water (10 mL), extracted with ethyl acetate (20 mL*3), the organic phases were combined, dried with anhydrous sodium sulfate, filtered, concentrated under reduced pressure, and the obtained crude product was directly separated and purified by preparative HPLC (column: Waters Xbridge BEH C18 (100*30 mm*10 μm); mobile phase: [aqueous solution containing ammonium bicarbonate (10 mM)-acetonitrile]; gradient: acetonitrile %: 10%-40%, 10 min) to obtain compound WX015.

$^1$H NMR (400 MHz, DMSO-$d_6$) δ=9.71 (s, 1H), 8.99 (s, 1H), 8.91 (s, 1H), 8.67 (s, 1H), 7.86 (s, 1H), 7.72 (s, 1H), 7.65 (s, 1H), 7.56-7.46 (m, 5H), 2.91-2.87 (m, 3H), 2.75-2.74 (m, 3H), 2.67 (s, 1H), 2.59 (s, 4H), 2.30 (s, 3H).

LCMS (ESI) m/z: 467.3 $[M+H]^+$

Embodiment 16: Synthesis of Compound WX016

WX016

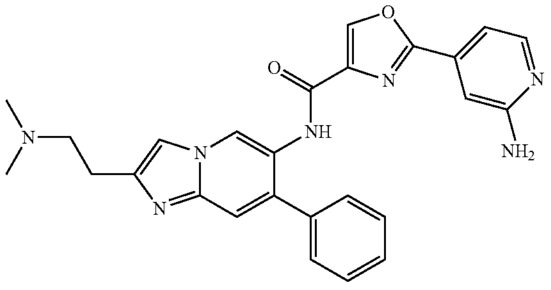

Synthetic Route:

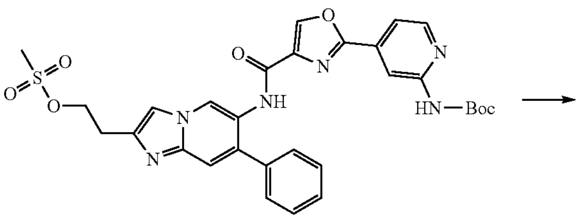

13-3

-continued

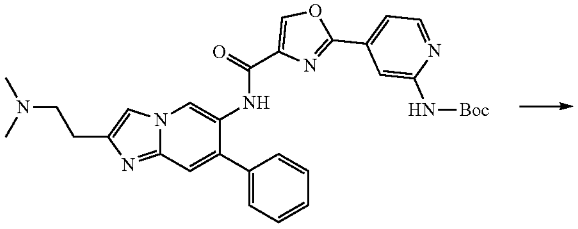

16-1

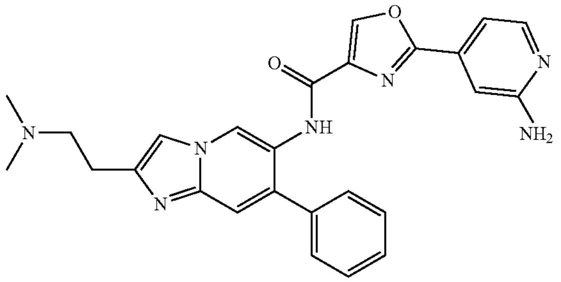

WX016

Step 1: Synthesis of Compound 16-1

Compound 13-3 (50 mg) and 1,4-dioxane (10 mL) were added into a pre-dried microwave tube, and then potassium iodide (33.54 mg), triethylamine (18.18 mg) and dimethylamine aqueous solution (178.00 mg, purity: 40%) were added, then heated to 80° C. and stirred for 2 hours, then aqueous solution of dimethylamine (267.00 mg, purity: 40%) was added, and the reaction was stirred at 80° C. for 2 hours. Ethyl acetate (10 mL), saturated brine (10 mL) and water (10 mL) were added to the reaction solution, and the solution was separated. The mixed solution of dichloromethane/methanol (10:1, 10 mL) was added to the aqueous phase for extraction and separation, and the organic phases were combined, dried with anhydrous sodium sulfate, filtered and concentrated under reduced pressure to obtain compound 16-1.

LCMS (ESI) m/z: 568.4[M+H]+

Step 2: Synthesis of Compound WX016

Compound 16-1 (60.00 mg) was added to a single-mouth bottle, then hydrochloric acid/methanol (4 M, 83.3 mL) was added to the bottle, and the solvent was distilled under reduced pressure at 45° C. to dryness, and the operation was repeated several times to obtain a crude product, which was separated and purified by preparative HPLC (column: Phenomenex Luna C18 (100*30 mm*5 μm); mobile phase: [aqueous solution containing hydrochloric acid (0.04%)-acetonitrile]; gradient: acetonitrile %: 10%-40%, 10 min) to obtain the hydrochloride of compound WX016.

LCMS (ESI) m/z: 468.3[M+H]+

$^1$H NMR (400 MHz, $D_2O$) δ=9.01 (s, 1H), 8.51 (s, 1H), 8.05 (s, 1H), 7.94-7.85 (m, 2H), 7.57-7.44 (m, 6H), 7.34-7.29 (m, 1H), 3.90 (s, 1H), 3.65-3.57 (m, 2H), 3.46-3.37 (m, 2H), 2.97 (s, 6H).

Embodiment 17: Synthesis of Compound WX017
WX017
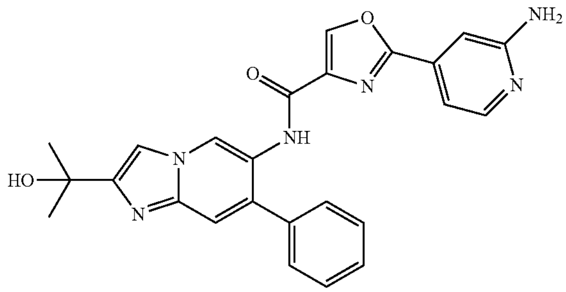
Synthetic Route:
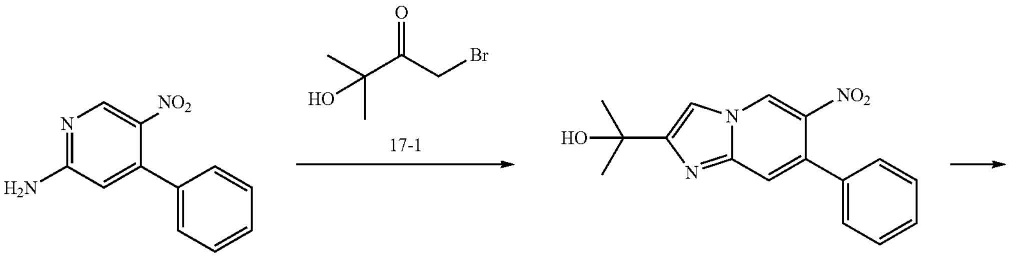
9-1
17-1
17-2
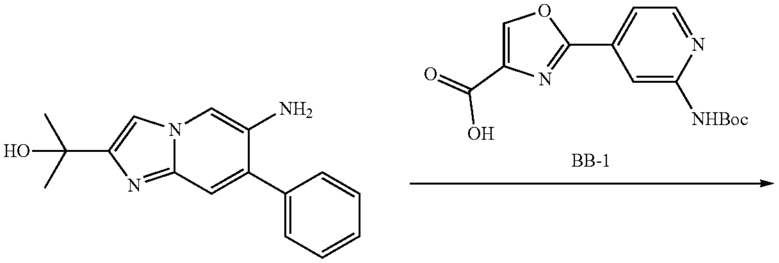
17-3
BB-1
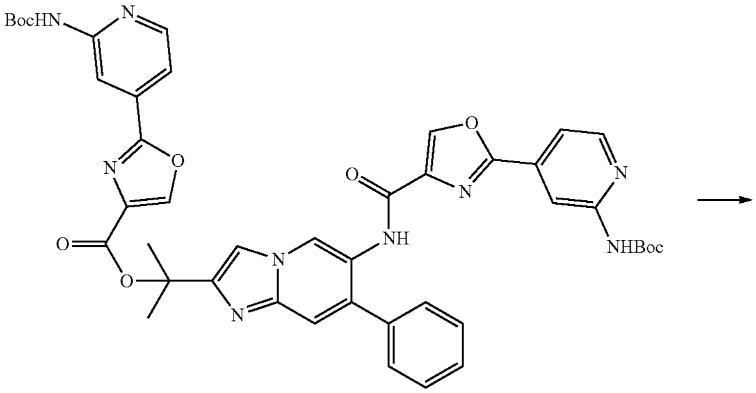
17-4

-continued

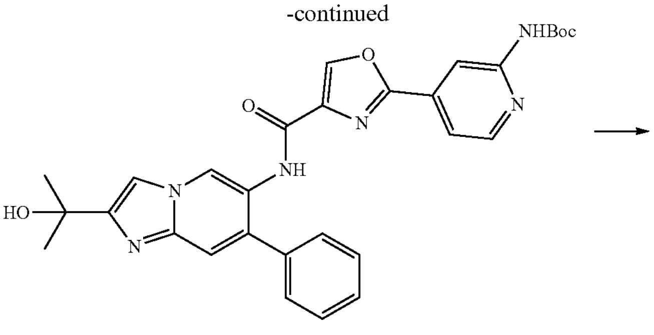

17-5

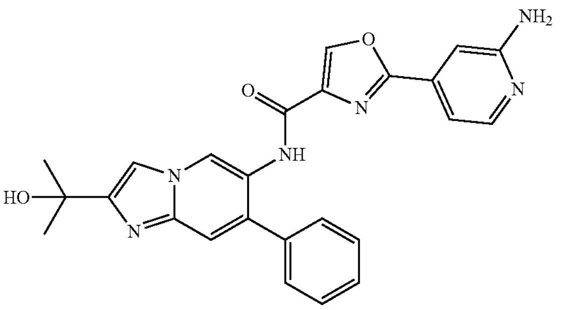

WX017

Step 1: Synthesis of Compound 17-2

Compound 9-1 (0.5 g) was dissolved in 1,4-dioxane (10 mL), then compound 17-1 (630.88 mg) and sodium bicarbonate (585.55 mg) were added, and the reaction was carried out at 70° C. for 16 hours. The reaction solution was concentrated under reduced pressure, then poured into water (50 mL) and ethyl acetate (50 mL), after liquid separation, the organic phase was dried with anhydrous sodium sulfate, and filtered and concentrated to obtain the crude compound. The residue was purified by column chromatography (eluent: petroleum ether/ethyl acetate=10:1 to 1:1) to obtain compound 17-2.

Step 2: Synthesis of Compound 17-3

Compound 17-2 (0.13 g) was dissolved in ethanol (3 mL) and acetic acid (1 mL), then iron powder (146.51 mg) was added, and the reaction was carried out at 40° C. for 2 hours. The reaction solution was concentrated under reduced pressure, then poured into water (20 mL) and ethyl acetate (20 mL), filtered and separated, and the organic phase was dried with anhydrous sodium sulfate, filtered and concentrated to obtain compound 17-3.

LCMS (ESI) m/z: 268.3[M+H]+

Step 3: Synthesis of Compound 17-4

Compound 17-3 (0.12 g) was dissolved in N,N-dimethylformamide (1 mL), and then O-(7-azabenzotriazole-1-YL)-N,N,N,N-tetramethylurea hexafluorophosphine salt (256.02 mg) and compound BB-1 (274.08 mg), diisopropylethylamine (174.04 mg) were added, and the reaction was carried out at 25° C. for 16 hours. Ethyl acetate (20 mL) and water (20 mL) were added to the reaction solution, after filtration, the filter cake was concentrated under reduced pressure to obtain crude compound 17-4.

LCMS (ESI) m/z: 842.4[M+H]+

Step 4: Synthesis of Compound 17-5

Compound 17-4 (0.08 g) was dissolved in tetrahydrofuran (1 mL), water (0.5 mL) and methanol (1 mL), then lithium hydroxide monohydrate (7.98 mg) was added, and the reaction was carried out at 25° C. for 48 hours. The pH value of the reaction solution was adjusted to 7 with 1 M hydrochloric acid, and then the reaction solution was concentrated under reduced pressure to dryness to obtain compound 17-5.

LCMS (ESI) m/z: 555.3[M+H]+

Step 5: Synthesis of Compound WX017

Compound 17-5 (0.03 g) was dissolved in dichloromethane (1 mL) and trifluoroacetic acid (0.5 mL), and the reaction was carried out at 25° C. for 1 hour. The reaction solution was concentrated under reduced pressure to obtain the crude compound. The obtained crude product was separated and purified by preparative HPLC (column: Waters Xbridge BEH C18 (100*30 mm*10 μm); mobile phase: [water (ammonium bicarbonate)-acetonitrile]; gradient: acetonitrile %: 15%-45%, 8 min) to obtain compound WX017.

LCMS (ESI) m/z: 455.3[M+H]+

$^1$H NMR (400 MHz, $D_2O$) δ=8.88 (s, 1H), 8.34 (s, 1H), 7.82 (s, 1H), 7.71-7.68 (m, 2H), 7.36-7.31 (m, 6H), 7.11-7.10 (m, 1H), 1.53 (s, 6H).

Embodiment 18: Synthesis of Compound WX018

WX018

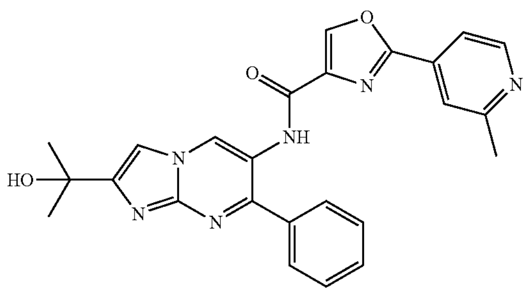

Synthetic Route:

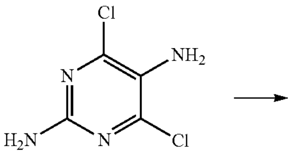

18-1

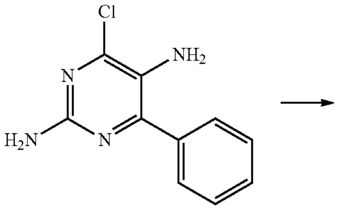

18-2

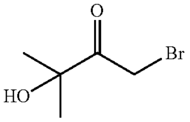

17-1

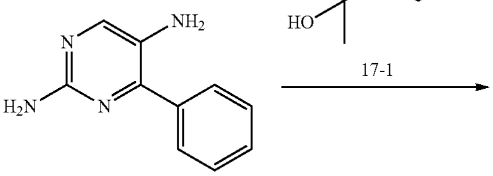

18-3

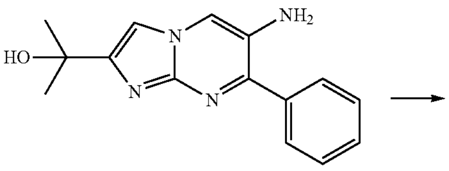

18-4

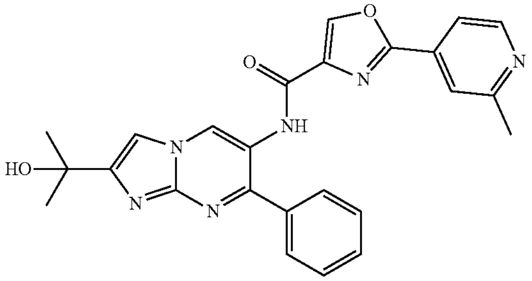

WX018

Step 1: Synthesis of Compound 18-2

Compound 18-1 (2 g) and phenylboronic acid (1.36 g) were dissolved in 1,4-dioxane (20 mL) and water (10 mL), then sodium carbonate (5.92 g) and triphenylphosphine palladium (645.54 mg) were added, and the reaction was carried out at 100° C. for 16 hours. The reaction solution was poured into water (50 mL), then extracted with ethyl acetate (50 mL*3), the organic phase was dried with anhydrous sodium sulfate, filtered and concentrated to obtain the crude compound. The residue was purified by column chromatography (eluent: petroleum ether/ethyl acetate=10:1 to 3:1) to obtain compound 18-2.

LCMS (ESI) m/z: 221.2[M+H]+

Step 2: Synthesis of Compound 18-3

Under the protection of nitrogen, wet palladium carbon (0.5 g, 10% purity) was dissolved in methanol (10 mL), then compound 18-2 (1.1 g) and sodium hydroxide aqueous solution (996.95 mg, 20% purity) were added, and the reaction solution was reacted at 25° C. under the condition of hydrogen (15 psi) for 1 hour. The reaction solution was filtered, and the filtrate was concentrated under reduced pressure to obtain a crude compound. The residue was purified by column chromatography (eluent: petroleum ether/ethyl acetate=10:1 to 3:1) to obtain compound 18-3.

Step 3: Synthesis of Compound 18-4

Compound 18-3 (0.3 g) and compound 17-1 (437.47 mg), sodium bicarbonate (406.02 mg) were dissolved in 1,4-dioxane (5 mL), and the reaction was carried out at 80° C. for 16 hours. The reaction solution was concentrated under reduced pressure, then water (20 mL) was added and the mixture was extracted with ethyl acetate (20 mL), the organic phase was dried with anhydrous sodium sulfate, filtered, and concentrated to obtain the crude compound. The residue was purified by column chromatography (eluent: petroleum ether/ethyl acetate=10:1 to 1:1) to obtain compound 18-4.

LCMS (ESI) m/z: 269.2[M+H]+

$^1$H NMR (400 MHz, DMSO-$d_6$) δ=8.25 (s, 1H), 7.81-7.79 (m, 2H), 7.59 (s, 1H), 7.52-7.48 (m, 3H), 4.98 (s, 1H), 4.67 (s, 2H), 1.48 (s, 6H).

Step 4: Synthesis of Compound WX018

Compound 18-4 (0.24 g) was dissolved in N,N-dimethylformamide (3 mL), and then O-(7-azabenzotriazole-1-YL)-N,N,N,N-tetramethylurea hexafluorophosphine salt (510.16 mg), compound BB-2 (182.64 mg) and diisopropylethylamine (346.81 mg) were added, the reaction was carried out at 25° C. for 16 hours. Ethyl acetate (5 mL) and water (5 mL) were added to the reaction solution, after filtration, the filter cake was concentrated under reduced pressure to obtain compound WX018.

LCMS (ESI) m/z: 455.3[M+H]+

$^1$H NMR (400 MHz, DMSO-$d_6$) δ=10.24 (s, 1H), 9.28 (s, 1H), 8.96 (s, 1H), 8.69-8.68 (m, 1H), 7.82-7.79 (m, 4H), 7.73-7.71 (m, 1H), 7.50-7.49 (m, 3H), 5.21 (s, 1H), 2.74 (s, 3H), 1.53 (s, 6H).

Embodiment 19: Synthesis of Compound WX019

WX019

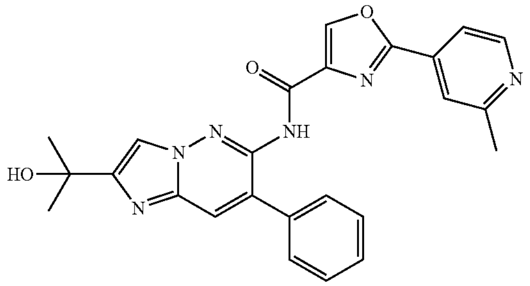

Synthetic Route:

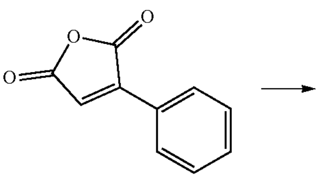

19-1

-continued

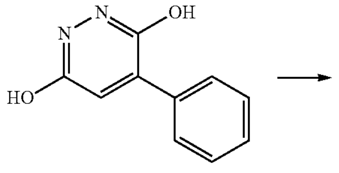

19-2

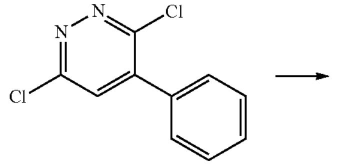

19-3

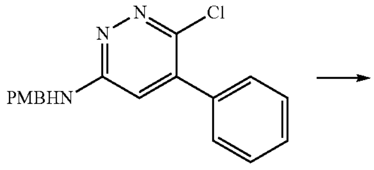

19-4

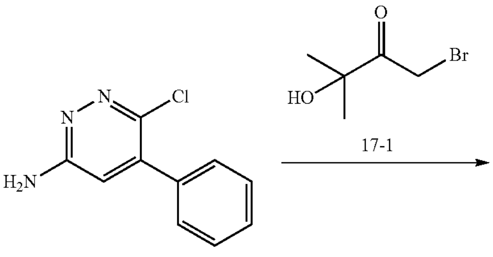

19-5

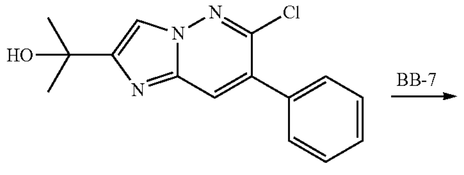

19-6

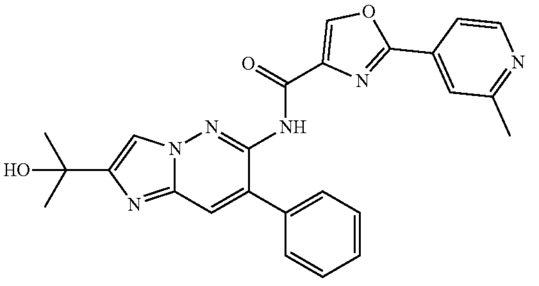

WX019

Step 1: Synthesis of Compound 19-2

Compound 19-1 (10 g) was dissolved in water (200 mL), then hydrazine sulfate (7.47 g) was added and the reaction was carried out at 100° C. for 16 hours. The reaction solution was directly filtered, the filter cake was rinsed with water (200 mL), and the filter cake was concentrated under reduced pressure to obtain compound 19-2.

$^1$H NMR (400 MHz, $CD_3OD$) δ=8.62 (s, 2H), 8.25-8.23 (m, 5H), 7.99 (s, 1H).

Step 2: Synthesis of Compound 19-3

Compound 19-2 (3 g) was dissolved in phosphorus oxychloride (24.44 g) and the reaction was carried out at 80° C. for 16 hours. The reaction solution was poured into water (300 mL), stirred for 1 hour and then filtered, and the filter cake was stirred with water (100 mL) for 1 hour and then filtered to obtain compound 19-3.

$^1$H NMR (400 MHz, DMSO-$d_6$) δ=8.20 (s, 1H), 7.64-7.62 (m, 2H), 7.57-7.55 (m, 3H).

Step 3: Synthesis of Compound 19-4

Compound 19-3 (2 g) was dissolved in dimethyl sulfoxide (1 mL), then p-methoxybenzylamine (6.09 g) was added, and the reaction was carried out at 120° C. for 16 hours. The reaction solution was poured into saturated ammonium chloride (50 mL), then extracted with ethyl acetate (50 mL*3), the organic phase was washed with saturated brine (50 mL*3), dried with anhydrous sodium sulfate, filtered and concentrated to obtain the crude compound. The residue was purified by column chromatography (eluent: petroleum ether/ethyl acetate=10:1 to 3:1) to obtain compound 19-4.

LCMS (ESI) m/z: 326.2[M+H]+

Step 4: Synthesis of Compound 19-5

Compound 19-4 (2 g) was dissolved in trifluoroacetic acid (25 mL) and the reaction was carried out at 70° C. for 2 hours. The reaction solution was concentrated under reduced pressure, then poured into sodium bicarbonate solution (50 mL), then extracted with ethyl acetate (50 mL*3), and the organic phase was dried with anhydrous sodium sulfate, filtered and concentrated to obtain the crude compound. The residue was purified by column chromatography (eluent: petroleum ether/ethyl acetate=3:1 to 1:1) to obtain compound 19-5.

LCMS (ESI) m/z: 206.1[M+H]+

Step 5: Synthesis of Compound 19-6

Compound 19-5 (0.1 g), compound 17-1 (132.04 mg) and sodium bicarbonate (122.55 mg) were dissolved in 1,4-dioxane (2 mL), and the reaction was carried out at 70° C. for 16 hours. The reaction solution was poured into water (50 mL), then extracted with ethyl acetate (50 mL*3), the organic phase was dried with anhydrous sodium sulfate, filtered and concentrated to obtain the crude compound. The residue was purified by column chromatography (eluent: petroleum ether/ethyl acetate=10:1 to 1:1) to obtain compound 19-6.

Step 6: Synthesis of Compound WX019

Compound 19-6 (0.1 g) and compound BB-7 (70.62 mg) were dissolved in 1,4-dioxane (0.5 mL), and then cesium carbonate (339.70 mg), 4,5-bis (diphenyl phosphino)-9,9-dimethyl xanthene (20.11 mg) and tris(dibenzylideneacetone)dipalladium were added. The reaction was carried out at 120° C. for 1 hour under microwave 0 psi. The reaction solution was concentrated under reduced pressure to obtain a crude compound. The obtained crude product was separated and purified by preparative HPLC (column: phenomenex C18 (80*40 mm*3 m); mobile phase: [water (ammonium bicarbonate)-acetonitrile]; gradient: acetonitrile %: 35%-65%, 8 min) to obtain compound WX019.

LCMS (ESI) m/z: 455.3[M+H]+

$^1$H NMR (400 MHz, $D_2O$) δ=8.30-8.32 (m, 2H), 7.91 (s, 1H), 7.81-7.76 (m, 3H), 7.25-7.14 (m, 5H), 2.41 (s, 3H), 1.29 (6H).

Embodiment 20: Synthesis of Compound WX020

WX020

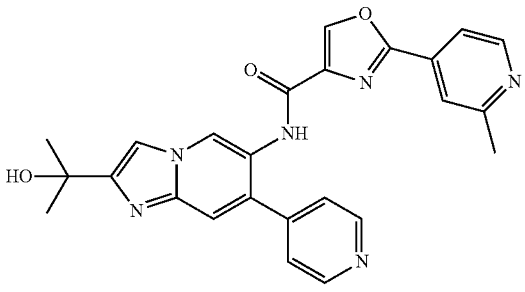

Synthetic Route:

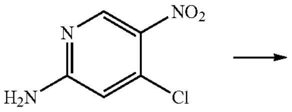

1-1

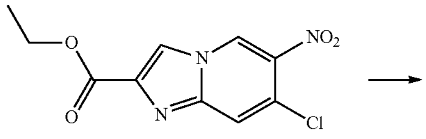

20-1

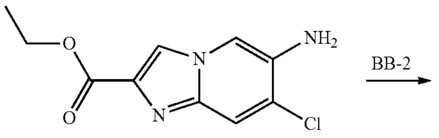

20-2

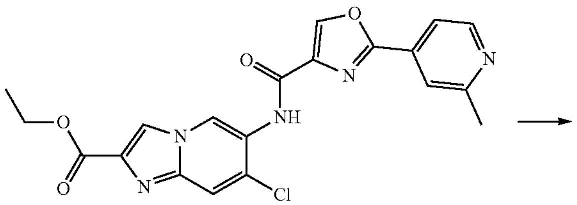

20-3

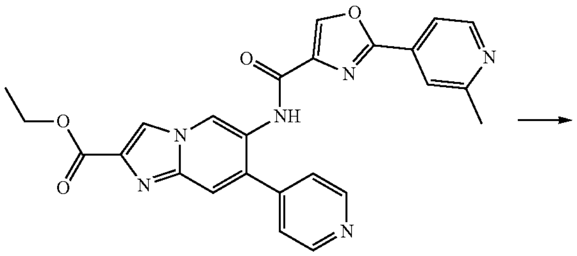

20-4

-continued

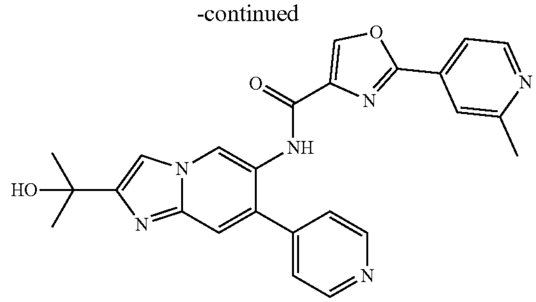

WX020

Step 1: Synthesis of Compound 20-1

Compound 1-1 (5.0 g) was dissolved in 1,4-dioxane (100.0 mL), then ethyl bromopyruvate (8.43 g) and sodium bicarbonate (4.84 g) were added, and the reaction solution was stirred at 70° C. for 16 hours. The reaction solution was directly spin-dried under reduced pressure, and the crude product was homogenized by adding water (150.0 mL), and after filtration, the compound 20-1 was obtained.

LCMS (ESI) m/z: 270.1[M+H]+

Step 2: Synthesis of Compound 20-2

20-1 (5.0 g) was added to the reaction flask and dissolved in ethyl acetate (75.0 mL), and then tin chloride dihydrate (25.11 g) was added, the reaction solution was carried out at 50° C. for 16 hours. 25% Ammonia water was added to the reaction solution to adjust the pH to 7, after filtration, the filtrate was concentrated under reduced pressure and purified it by column chromatography (eluent: petroleum ether:ethyl acetate=100:0 to 91:9) to obtain compound 20-2.

LCMS (ESI) m/z: 240.2[M+H]+

Step 3: Synthesis of Compound 20-3

20-2 (0.5 g), compound BB-2 (511.18 mg), N,N-diisopropylethylamine (674.09 mg), O-(7-azabenzotriazole-1-yl)-N,N,N,N-tetramethylurea hexafluorophosphine salt (1.19 g) and N, N-dimethylformamide (12 mL) were added into the reaction flask, the reaction was carried out at 25° C. for 16 hours after the reaction system was replaced with nitrogen. Water (3 mL) and ethyl acetate (3 mL) were added to the reaction solution, stirred for 10 minutes, filtered and the filter cake was collected. The filter cake was homogenized with 0.1 M sodium hydroxide solution (10 mL) for 1 hour, filtered, and the filter cake was collected to obtain compound 20-3.

LCMS (ESI) m/z: 426.2[M+H]+

Step 4: Synthesis of Compound 20-4

Compound 20-3 (0.3 g), 4-pyridylboronic acid (129.90 mg), sodium carbonate (2 M, 880.64 μL), bis (triphenylphosphine) palladium dichloride (24.72 mg) and N,N-dimethylformamide (10 mL) were added into a microwave tube, and after the reaction system was replaced with nitrogen, the reaction was carried out at 110° C. and 1 bar under microwave. The reaction solution was filtered and the filter cake was collected to obtain compound 20-4.

LCMS (ESI) m/z: 469.2[M+H]+

Step 5: Synthesis of Compound WX020

3 M tetrahydrofuran solution of methyl magnesium chloride (2.42 mL) was added to anhydrous tetrahydrofuran (5 mL) at 0° C., then the anhydrous tetrahydrofuran solution (2 mL) of compound 20-4 (170.00 mg) was slowly added dropwise, and the temperature was raised to 25° C., and the reaction was carried out for 0.5 hour. The reaction solution was added into water (20 mL), then ethyl acetate (20 mL*3) was added for extraction and separation, the organic phases were combined, dried with anhydrous sodium sulfate, filtered, and the filtrate was concentrated under reduced pressure. The obtained crude product was separated and purified by preparative HPLC (column: Waters Xbridge BEH C18 (100*30 mm*10 μm); mobile phase: [water (ammonium bicarbonate)-acetonitrile]; gradient: acetonitrile %: 20%-40%, 8 min) to obtain compound WX020.

LCMS (ESI) m/z: 455.3 [M+H]+

$^{1}$H NMR (400 MHz, DMSO-$d_6$) δ=10.08 (s, 1H), 8.89 (s, 1H), 8.45 (m, 1H), 8.69-8.68 (m, 1H), 8.63-8.68 (m, 2H), 7.88 (s, 1H), 7.81 (s, 1H), 7.73-7.72 (m, 1H), 7.64 (s, 1H), 7.56-7.55 (m, 2H), 5.13 (s, 1H), 2.60 (s, 3H), 1.52 (s, 6H).

Embodiment 21: Synthesis of Compound WX021

WX021

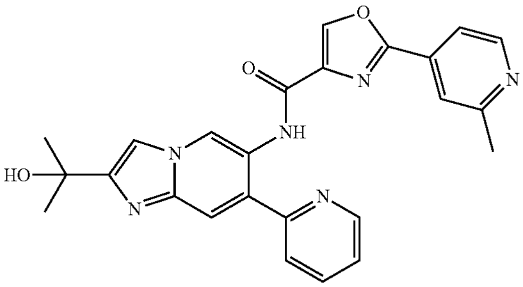

Synthetic Route:

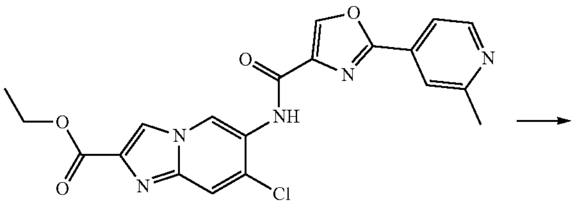

20-3

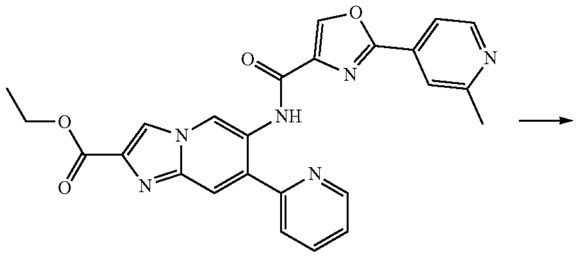

21-1

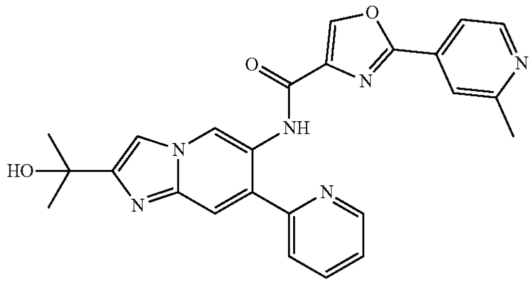

WX021

Step 1: Synthesis of Compound 21-1

Compound 20-3 (0.1 g), 2-(tributylstannyl) pyridine (129.68 mg), chlorine (2-dicyclohexylphosphino-2,4,6-triisopropyl-1,1-biphenyl)[2-(2-amino-1,1-biphenyl)]palladium were dissolved in 1,4-dioxane, and the reaction solution was stirred at 100° C. for 16 hours. The reaction solution was directly filtered, the filter cake was washed with water (10 mL), and the filter cake was collected to obtain compound 21-1.

LCMS (ESI) m/z: 469.2[M+H]$^+$

Step 2: Synthesis of Trifluoroacetate of Compound WX021.

Tetrahydrofuran (10 mL) was added to the reaction flask, and the reaction system was replaced with nitrogen for three times, the temperature was lowered to 0° C., 3 M tetrahydrofuran solution of methylmagnesium chloride (7.47 mL) was added, and then the mixture of compound 21-1 (0.35 g) and tetrahydrofuran (5 mL) was added, and the temperature was raised to 25° C., and the reaction was carried out for 1 hour. The reaction solution was slowly poured into water (10 mL), extracted and separated with ethyl acetate (10 mL*3), and the organic phases were spin-dried under reduced pressure, then separated and purified by preparative HPLC (column: phenomenex Luna (80*30 mm*3 m); mobile phase: [water (trifluoroacetic acid)-acetonitrile]; gradient: acetonitrile %: 15%-37%, 8 min) to obtain trifluoroacetate of compound WX021.

LCMS (ESI) m/z: 455.3[M+H]$^+$ $^{1}$H NMR (400 MHz, DMSO-$d_6$) δ=10.00 (s, 1H), 9.12 (s, 1H), 9.08-9.03 (m, 1H), 8.79-8.75 (m, 1H), 8.43 (s, 1H), 8.25 (s, 1H) 8.24-8.21 (m, 2H), 7.89 (s, 1H), 7.86-7.83 (m, 1H), 7.79-7.75 (m, 1H), 2.66 (s, 3H), 1.61 (s, 6H).

Embodiment 22: Synthesis of Compound WX022

WX022

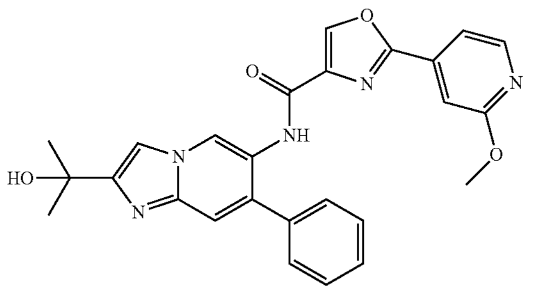

Synthetic Route:

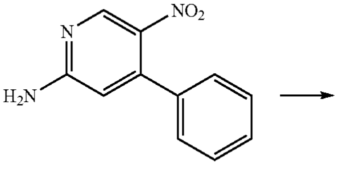

9-1

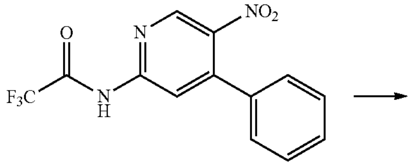

22-1

-continued

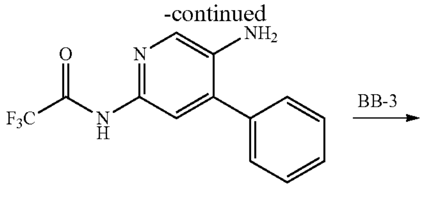

22-2

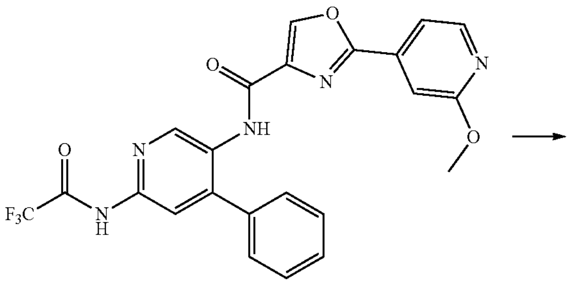

22-3

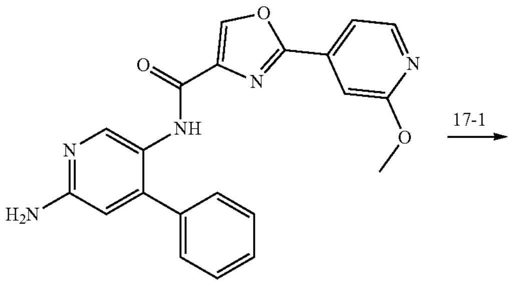

22-4

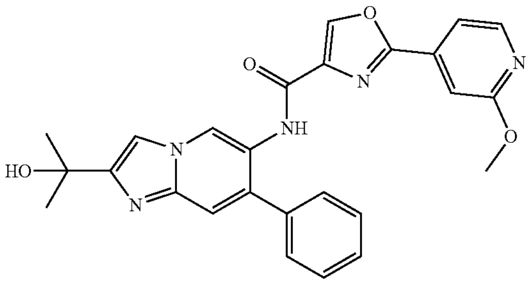

WX022

Step 1: Synthesis of Compound 22-1

Compound 9-1 (5 g) was added to anhydrous dichloromethane (100 mL), and after cooled to 0° C., triethylamine (3.53 g) and trifluoroacetic anhydride (6.93 g) were slowly added and the reaction mixture was stirred at 0° C. for 1 hour. The reaction solution was added into saturated ammonium chloride aqueous solution (100 mL), extracted and separated with dichloromethane (50 mL*2), the organic phases were combined, dried with anhydrous sodium sulfate, and filtered, and the filtrate was concentrated under reduced pressure to obtain compound 22-1.

LCMS (ESI) m/z: 312.0[M+H]$^+$

Step 2: Synthesis of Compound 22-2

Wet palladium carbon (2 g, 10% purity) was added into a dry hydrogenation bottle under argon protection, anhydrous methanol (100 mL), compound 22-1 (7 g) were added and reacted at 30° C. for 2 h under hydrogen (50 psi). After the reaction, the reaction solution was filtered with diatomite, and the filtrate was concentrated under reduced pressure and purified by column chromatography (eluent: petroleum ether:ethyl acetate=100:0 to 75:25) to obtain compound 22-2.

LCMS (ESI) m/z: 282.0[M+H]$^+$ $^1$H NMR (400 MHz, $CD_3OD$) δ=7.91 (s, 1H), 7.63 (s, 1H), 7.48-7.41 (m, 4H), 7.40 (s, 1H).

Step 3: Synthesis of Compound 22-3

Compound 22-2 (0.6 g) and compound BB-3 (563.70 mg) were added to N,N-dimethylformamide (3 mL), then O-(7-azabenzotriazole-1-yl)-N,N,N,N-tetramethylurea hexafluorophosphate (1.22 g) and N,N-diisopropylethylamine (827.19 mg) were added, and the mixture was stirred at 25° C. for 12 hours. Water (10 mL) was added to the reaction solution, and the mixture was stirred for 2 hours and filtered, and the filter cake was concentrated under reduced pressure to obtain compound 22-3.

LCMS (ESI) m/z: 484.0[M+H]$^+$ $^1$H NMR (400 MHz, DMSO-$d_6$) δ=12.25-12.15 (m, 1H), 9.93 (s, 1H), 8.80 (s, 1H), 8.40 (s, 1H), 8.39 (s, 1H), 8.00 (s, 1H), 7.56-7.47 (m, 6H), 7.26 (s, 1H), 3.93 (s, 3H).

Step 4: Synthesis of Compound 22-4

Compound 22-3 (0.32 g) was added to anhydrous methanol (5 mL), and anhydrous potassium carbonate (228.73 mg) was added and the reaction was carried out at 60° C. for 2 hours. Water (4 mL) was added to the reaction solution, and the mixture was stirred for 0.5 hours and filtered, and the filter cake was concentrated under reduced pressure to obtain compound 22-4.

Step 5: Synthesis of Compound WX022

Compound 22-4 (0.22 g) and compound 17-1 (185.05 mg) were added to anhydrous dioxane (4 mL), and sodium bicarbonate (119.27 mg) was added and the reaction was carried out at 75° C. for 12 hours. The reaction solution was slowly poured into water (30 mL), extracted and separated with ethyl acetate (30 mL*3), the organic phases were combined, dried with anhydrous sodium sulfate and filtered, and the organic phases were spin-dried under reduced pressure and separated and purified by preparative HPLC (column: phenomenex C18 (80*40 mm*3 m); mobile phase: [water (ammonium bicarbonate)-acetonitrile]; gradient: acetonitrile %: 25%-45%, 8 min) to obtain compound WX022.

LCMS (ESI) m/z: 470.2[M+H]$^+$ $^1$H NMR (400 MHz, $CD_3OD$) δ=9.23 (s, 1H), 8.56 (s, 1H), 8.28-8.27 (m, 1H), 7.80 (s, 1H), 7.57-7.55 (m, 5H), 7.45 (s, 1H), 7.40-7.38 (m, 1H), 7.23 (s, 1H), 3.96 (s, 3H), 1.62 (s, 6H).

Embodiment 23: Synthesis of Compound WX023

WX023

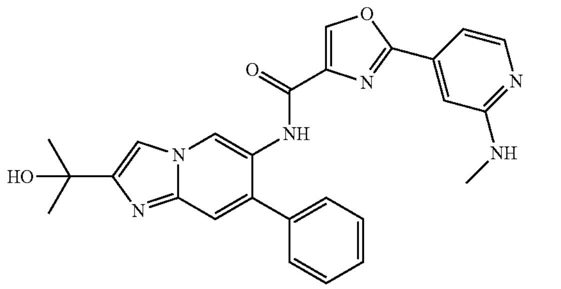

Synthetic Route:

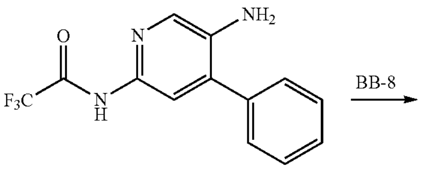

22-2

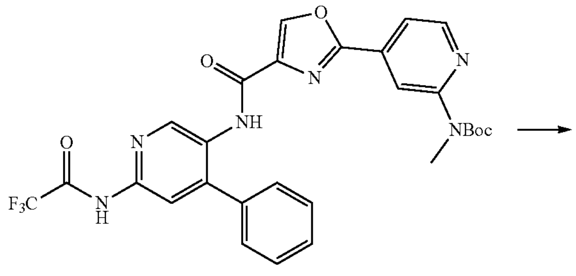

23-1

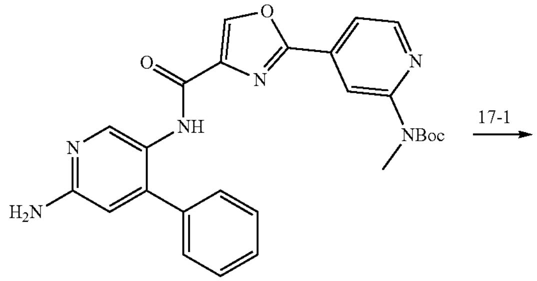

23-2

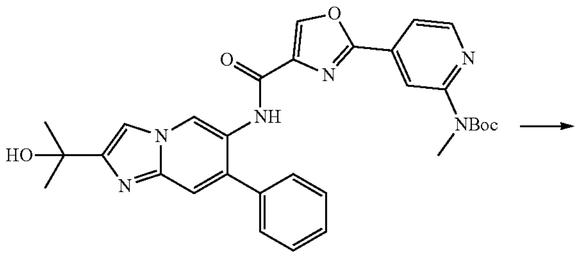

23-3

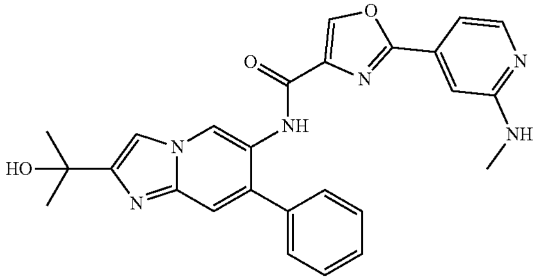

WX023

Step 1: Synthesis of Compound 23-1

Compound 22-2 (0.3 g) and compound BB-8 (408.74 mg) were added to N,N-dimethylformamide (6 mL), then O-(7-azabenzotriazole-1-yl)-N,N,N,N-tetramethylurea hexafluorophosphate (608.41 mg) and N,N-diisopropylethylamine (344.67 mg) were added, and the mixture was stirred at 40° C. for 16 hours. Water (10 mL) was added to the reaction solution, and the mixture was stirred for 1 hour, then filtered, the filter cake was concentrated under reduced pressure, the crude product was poured into 0.1M aqueous solution of sodium hydroxide (10 mL), stirred for 2 hours, and filtered, the filter cake was concentrated under reduced pressure to obtain compound 23-1.

LCMS (ESI) m/z: 583.2[M+H]$^+$

Step 2: Synthesis of Compound 23-2

Compound 23-1 (0.46 g) was added to anhydrous methanol (10 mL), and then potassium carbonate (272.84 mg) was added and the reaction was carried out at 60° C. for 16 hours. Water (10 mL) was added to the reaction solution, and the mixture was stirred for 1 hour and filtered, and the filter cake was concentrated under reduced pressure to obtain compound 23-2.

LCMS (ESI) m/z: 487.3[M+H]$^+$

Step 3: Synthesis of Compound 23-3

Compound 23-2 (0.32 g) and compound 17-1 (214.32 mg) were added to anhydrous dioxane (6 mL), and sodium bicarbonate (138.13 mg) was added, the reaction solution was reacted at 75° C. for 5 hours. Water (6 mL) was added to the reaction solution, stirred for 1 hour and the mixture was filtered, and the filter cake was concentrated under reduced pressure to remove water to obtain compound 23-3.

LCMS (ESI) m/z: 569.3[M+H]$^+$

Step 4: Synthesis of Compound WX023

Compound 23-3 (0.3 g) were added to the mixture of anhydrous dichloromethane (36 mL) and trifluoroacetic acid (12 mL), and the reaction solution was reacted at 25° C. for 2 hours. After the reaction solution was concentrated under reduced pressure, the obtained crude product was separated and purified by preparative HPLC (column: Waters Xbridge BEH C18 (100*30 mm*10 μm); mobile phase: [Water (ammonium bicarbonate)-acetonitrile]; gradient: acetonitrile %: 20%-50%, 10 min) to obtain compound WX023.

LCMS (ESI) m/z: 469.3[M+H]$^+$ $^1$H NMR (400 MHz, DMSO-$d_6$) δ=9.69 (s, 1H), 9.05 (s, 1H), 8.85 (s, 1H), 8.17 (s, 1H), 7.90 (s, 1H), 7.57-7.45 (m, 6H), 6.94-6.93 (m, 3H), 5.18 (s, 1H), 2.83 (s, 3H), 1.52 (s, 6H).

Embodiment 24: Synthesis of Compound WX024

WX024

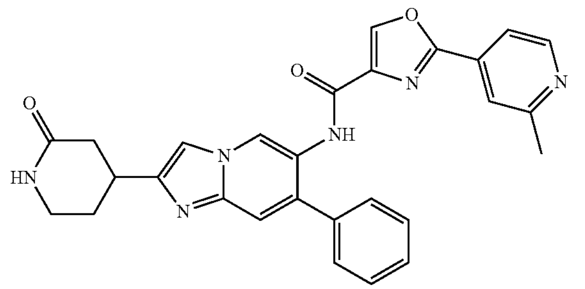

Synthetic Route:

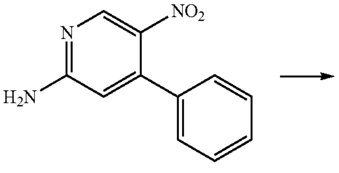

9-1

-continued

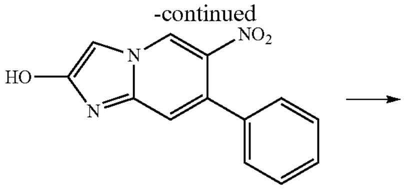

24-1

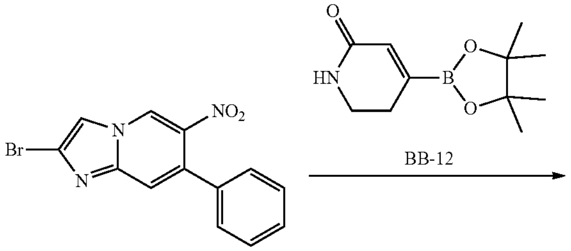

24-2 BB-12

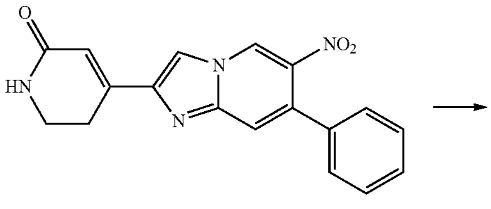

24-3

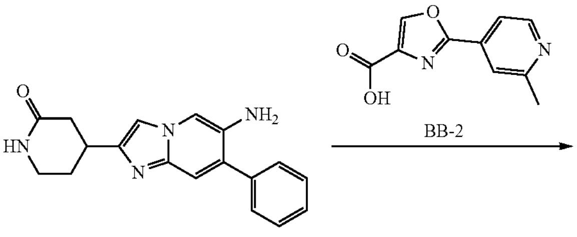

24-4 BB-2

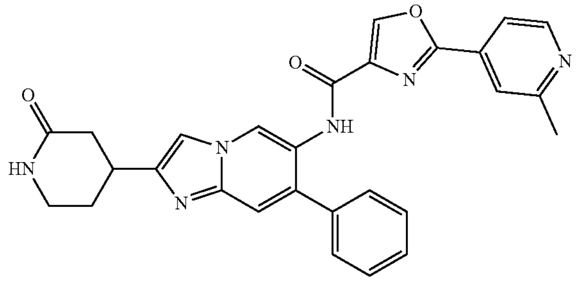

WX024

Step 1: Synthesis of Hydrobromate of Compound 24-1

Compound 9-1 (15 g) and methyl bromoacetate (106.62 g) were placed in a vial, and the reaction was stirred at 40° C. for 16 hours. Methyl tert-butyl ether (200.0 mL) was added to the reaction solution, then filtered, and the filter cake was concentrated under reduced pressure to obtain hydrobromate of compound 24-1.

$^1$H NMR (400 MHz, DMSO-$d_6$) δ=9.36 (s, 1H), 7.60-7.40 (m, 5H), 7.16 (s, 1H), 5.35 (s, 2H).

Step 2: Synthesis of Compound 24-2

Hydrobromate of compound 24-1 (21 g) was dissolved in acetonitrile (20 mL), and then a solution of phosphorus oxybromide (35.82 g) in acetonitrile (20 mL) was added and the reaction was carried out at 80° C. for 144 hours. The reaction solution was poured into saturated sodium bicarbonate solution (200.0 mL), then extracted with ethyl acetate (50.0 mL*3), the organic phases were combined, dried with anhydrous sodium sulfate, filtered by suction and spin-dried under reduced pressure, and then purified by column chromatography (eluent: petroleum ether:ethyl acetate=91:9 to 0:100) to obtain compound 24-2.

Step 3: Synthesis of Compound 24-3

Compound 24-2 (0.6 g) and compound BB-12 (1.51 g) dissolved in 1,4-dioxane (20 mL) were added to the reaction flask, and then [1,1-bis (di-tert-butylphosphine) ferrocene] palladium (II) dichloride (61.64 mg) and potassium carbonate (2M, 1.89 mL) were added, and the reaction was carried out at 100° C. for 2.5 hours. Water (50.0 mL) was added to the reaction solution, and the mixture was extracted with dichloromethane (50.0 mL), the organic phases were combined, concentrated to obtain a crude product, and the crude product was purified by silica gel column chromatography (eluent: dichloromethane:methanol=99:1 to 91:9) to obtain compound 24-3.

LCMS (ESI) m/z: 335.2 $[M+H]^+$

Step 4: Synthesis of Compound 24-4

Under the protection of nitrogen, compound wet palladium carbon (0.1 g, 10% purity) was put in a hydrogenation bottle, then methanol (10 mL) was added, and then compound 24-3 (0.06 g) was added, and the reaction was carried out at 30° C. for 16 hours under hydrogen with the pressure of 50 psi. The reaction solution was filtered with diatomite, and the filtrate was concentrated under reduced pressure to obtain compound 24-4.

LCMS (ESI) m/z: 307.2 $[M+H]^+$

Step 5: Synthesis of Compound WX024

Compound 24-4 (0.1 g) was dissolved in N,N-dimethylformamide (2 mL), then O-(7-azabenzotriazole-1-yl)-N,N,N,N-tetramethylurea hexafluorophosphate (186.17 mg) and N,N-diisopropylethylamine (126.56 mg), compound BB-2 (79.98 mg) were added, and the mixture was stirred at 40° C. for 16 hours. Water (50.0 mL) was added to the reaction solution and the mixture was filtered, and the filter cake was concentrated under reduced pressure to obtain crude compound. The obtained crude product was purified by machine separation (column: Waters Xbridge Prep OBD C18 (150*40 mm*10 μm); flow phase: [water (ammonium bicarbonate)-acetonitrile]; gradient: acetonitrile %: 25%-45%, 8 min) to obtain compound WX024.

LCMS (ESI) m/z: 493.2 $[M+H]^+$ $^1$H NMR (400 MHz, $D_2O$-$d_2$) δ=8.82 (s, 1H), 8.34-8.32 (m, 1H), 8.25 (s, 1H), 7.90-7.85 (m, 2H), 7.64-7.62 (m, 1H), 7.48 (s, 1H), 7.20 (s, 5H), 3.10-3.09 (m, 1H), 3.08-3.07 (m, 2H), 2.58-2.52 (m, 1H), 2.45 (s, 3H), 2.32-2.25 (m, 1H), 1.97-1.95 (m, 1H), 1.69-1.67 (m, 1H).

Embodiment 25: Synthesis of Compound WX025 and WX037

WX025

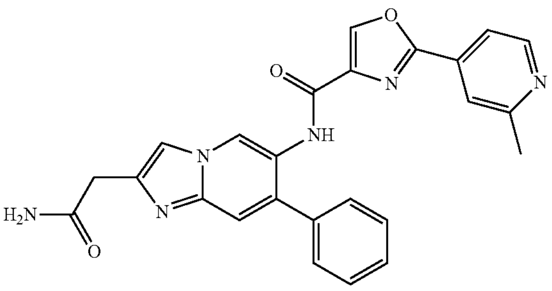

-continued

WX037

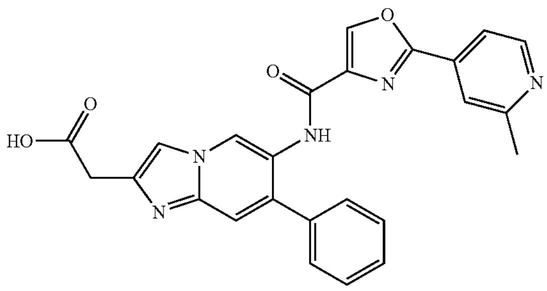

Synthetic Route:

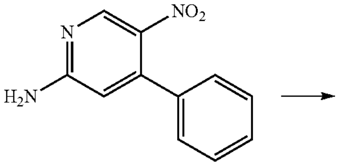

9-1

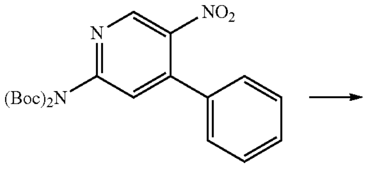

25-1

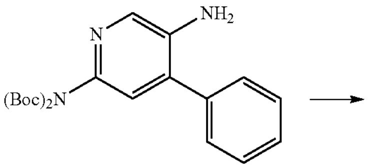

25-2

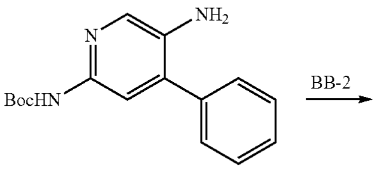

25-3

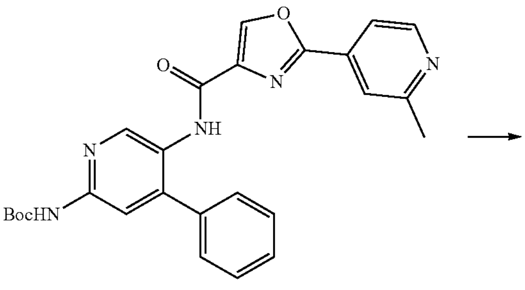

25-4

-continued

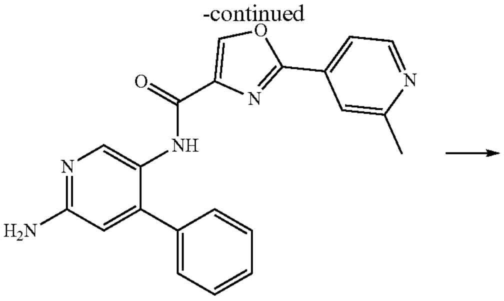

25-5

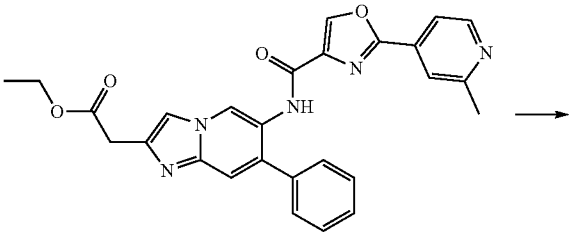

25-6

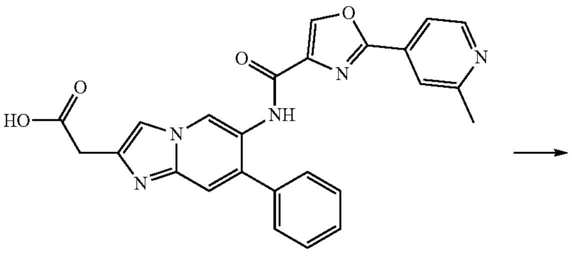

WX037

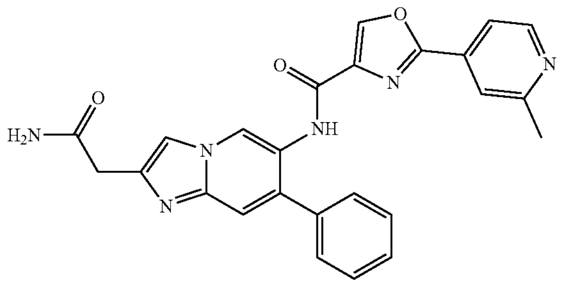

WX025

Step 1: Synthesis of Compound 25-1

Compound 9-1 (78 g), dichloromethane (390 mL), 4-dimethylaminopyridine (6.64 g), Boc anhydride (237.30 g) were added into a reaction flask, and then the mixture was reacted at 20° C. for 12 hours. The reaction solution was added into saturated ammonium chloride (50 mL), separated, the organic phase was washed once with saturated ammonium chloride aqueous solution (50 mL), and the organic phase was concentrated to obtain the crude product. The crude product was heated to 80° C. with methanol (1200 mL) and dissolved. The reaction solution was moved to room temperature 20° C., and water (600 mL) was added, and the mixture was stirred for 30 min, filtered and the filter cake was concentrated to obtain the product.

$^1$H NMR (400 MHz, $CDCl_3$) δ=1.55 (s, 18H), 7.35 (dd, J=6.40 Hz, J=3.20 Hz, 2H), 7.50-7.44 (m, 3H), 7.66 (s, 1H), 8.93 (s, 1H).

Step 2: Synthesis of Compound 25-2

Wet palladium carbon (7.4 g, 10% purity) was added into a hydrogenation bottle, wetted with methanol (10 mL), then a methanol (730 mL) solution of compound 25-1 (74 g) was added, and then the reaction was carried out at 30° C. for 12 hours under hydrogen with pressure of 50 psi. The solution was filtered through diatomite, and the filter cake was rinsed with dichloromethane:methanol=10:1 (3000 mL). The filtrate was concentrated to obtain compound 25-2.

$^1$H NMR (400 MHz, $CD_3OD$) δ=1.43 (s, 18H), 6.96 (s, 1H), 7.55-7.43 (m, 5H), 7.94 (s, 1H).

Step 3: Synthesis of Compound 25-3

Compound 25-2 (128 g), methanol (1280 mL), water (300 mL) and sodium hydroxide (53.13 g) were added to the reaction flask and reacted at 40° C. for 12 hours. Water (65 mL) was added to the reaction solution, and ethyl acetate (45 mL*2) was added for extraction, the organic phases were combined, and concentrated to obtain compound 25-3.

$^1$H NMR (400 MHz, $CDCl_3$) δ=1.52 (s, 9H), 3.61 (s, 2H), 7.51-7.40 (m, 6H), 7.76 (s, 1H), 7.84 (s, 1H).

Step 4: Synthesis of Compound 25-4

Compound BB-2 (40.00 g), compound 25-3 (46.58 g), N,N-dimethylformamide (120 mL), N,N-diisopropylethylamine (63.29 g) and O-(7-azabenzotriazole-1-yl)-N,N,N,N-tetramethylurea hexafluorophosphate (93.11 g) were added to the reaction flask and reacted at 40° C. for 12 hours. The reaction solution was filtered, and the filter cake was homogenized with 1M sodium hydroxide solution (200 mL) for 30 min, filtered and the filter cake was dried for 24 h at 45° C. to obtain compound 25-4.

LCMS (ESI) m/z: 472.3[M+H]$^+$ $^1$H NMR (400 MHz, DMSO-$d_6$) δ=9.95 (s, 1H), 9.83 (s, 1H), 8.89 (s, 1H), 8.66-8.65 (m, 1H), 8.50 (s, 1H), 7.84 (s, 1H), 7.75 (s, 1H), 7.67-7.66 (m, 1H), 7.51-7.46 (m, 5H), 2.57 (s, 3H), 1.46 (s, 9H).

Step 5: Synthesis of Compound 25-5

Compound 25-4 (66.5 g), trifluoroacetic acid (220 mL) and dichloromethane (660 mL) were added into a reaction flask, and then the mixture was reacted at 20° C. for 12 hours and concentrated to obtain a crude product, and the pH value of the crude product was adjusted to 7 by adding 1M sodium hydroxide aqueous solution (400 mL), and dichloromethane:methanol=3:1 (500 mL*5) was added for extraction, and the organic phases were combined and concentrated to obtain the crude product. The crude product was homogenized with 0.5 M aqueous solution of lithium hydroxide (130 mL) for 10 minutes, filtered, the filter cake was slurried with acetonitrile (100 mL), filtered, and the filter cake was concentrated to remove the dissolved residue to obtain compound 25-5.

LCMS (ESI) m/z: 372.2[M+H]$^+$ $^1$H NMR (400 MHz, DMSO-$d_6$) δ=9.58 (s, 1H), 8.82 (s, 1H), 8.66-8.65 (m, 1H), 8.04 (s, 1H), 7.77 (s, 1H), 7.69-7.68 (m, 1H), 7.47.39 (m, 5H), 6.47 (s, 1H), 6.06 (s, 2H), 2.57 (s, 3H).

Step 6: Synthesis of Compound 25-6

Compound 25-5 (1 g) 1,4-dioxane (10 mL), compound B7 (1.41 g) and sodium bicarbonate (678.58 mg) were added into a reaction flask and reacted at 75° C. for 12 hours. Water (10 mL) was added to the reaction solution, solids were precipitated, filtered, and the filter cake was concentrated to obtain a crude product. The crude product was separated and purified by silica gel column chromatography (gradient eluent: dichloromethane:methanol=95:5 to 90:10) to obtain compound 25-6.

LCMS: m/z (ESI)=482.2[M+H]$^+$

Step 7: Synthesis of Compound WX037

Compound 25-6 (0.44 g) and ethanol (6 mL) were added to the reaction flask, and then a aqueous solution (2 mL) of lithium hydroxide monohydrate (43.77 mg) was added, and the reaction was carried out at 25° C. for 3 hours. 1M hydrochloric acid was added to the reaction solution to adjust the pH value to 4, and dichloromethane:methanol=8:1 (50 mL*3) was added for extraction, organic phases were combined, and concentrated to obtain the crude compound WX037.

A part of crude WX037 (0.18 g, 396.96 mol, 1 eq) was separated and purified by preparative HPLC (column: Phenomenex Luna C18 (75*30 mm*3 μm); mobile phase: [water (formic acid)-acetonitrile]; gradient: acetonitrile %: 20%-50%, 8 min) to obtain the compound WX037.

LCMS: m/z (ESI)=453.2[M+H]$^+$ $^1$H NMR (400 MHz, DMSO-$d_6$) δ=9.88 (s, 1H), 9.43 (s, 1H), 9.00 (s, 1H), 8.69 (d, J=4.80 Hz, 1H), 8.28 (s, 1H), 7.86 (s, 1H), 7.72 (s, 1H), 7.66-7.57 (m, 6H), 3.99 (s, 2H), 2.60 (s, 3H).

Step 8: Synthesis of Compound WX025

Compound WX037 (0.2 g), ammonium chloride (117.96 mg), N,N dimethylformamide (2 mL), 1-(3-dimethylaminopropyl)-3-ethylcarbodiimide hydrochloride (126.83 mg), diisopropylethylamine (570.03 mg), 1-hydroxybenzotriazole (89.39 mg) were added to the reaction flask and reacted at 25° C. for 12 hours. Then the reaction solution was added into saturated ammonium chloride aqueous solution (20 mL), then ethyl acetate (20 mL*3) was added for extraction and liquid separation, the organic phases were combined, concentrated to obtain a crude product, which was separated and purified by preparative HPLC (column: Waters Xbridge Prep OBD C18 (150*40 mm*10 μm); mobile phase: [water (ammonium bicarbonate)-acetonitrile]; gradient: acetonitrile %: 15%-50%, 8 min) to obtain compound WX025.

LCMS: m/z (ESI)=453.2[M+H]$^+$ $^1$H NMR (400 MHz, DMSO-$d_6$) δ=9.73 (s, 1H), 9.02 (s, 1H), 8.92 (s, 1H), 8.67 (d, J=5.20 Hz, 1H), 7.91 (s, 1H), 7.73 (s, 1H), 7.65 (d, J=5.20 Hz, 1H), 7.58-7.44 (m, 7H), 6.98 (s, 1H), 3.56 (s, 2H), 2.59 (s, 3H).

Embodiment 26: Synthesis of Compound WX026

WX026

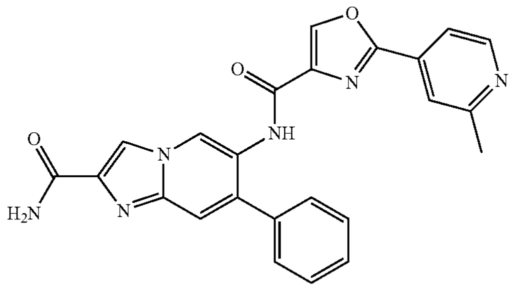

Synthetic Route:

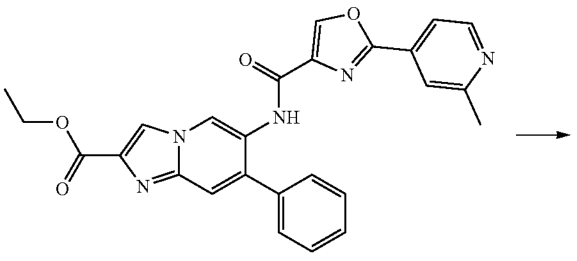

9-4

-continued

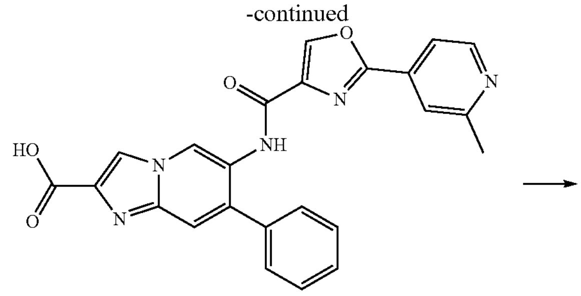

26-1

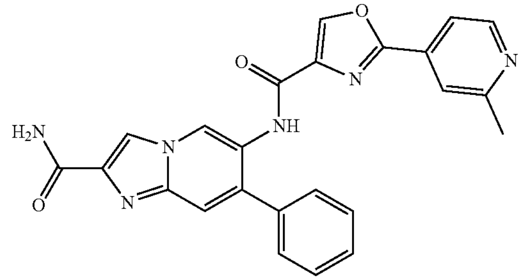

WX026

Step 1: Synthesis of Compound 26-1

Compound 9-4 (0.2 g) was dissolved in ethanol (4 mL) and water (4 mL), then lithium hydroxide monohydrate (53.86 mg) was added, and the reaction solution was stirred at 25° C. for 3 hours. The reaction solution was spin-dried under reduced pressure, the ethanol phase was removed, and the remaining aqueous phase was adjusted to pH 4-5 with 1 M aqueous hydrochloric acid, stirred for 10 min and filtered directly, then the filter cake was washed with water (10 mL), collected and homogenized with acetonitrile (10 mL) for 1 h and filtered, and the filter cake was collected to obtain compound 26-1.

Step 2: Synthesis of Compound WX026

26-1 (0.14 g), ammonium chloride (34.08 mg), 1-ethyl-(3-dimethylaminopropyl) carbonyldiimide hydrochloride (91.61 mg), 1-hydroxybenzotriazole (64.58 mg), N,N-diisopropylethylamine (205.88 mg) and N, N-dimethylformamide (5 mL) were added to the reaction flask, the reaction system was replaced with nitrogen three times, and the reaction solution was stirred at 40° C. for 16 h. The reaction solution was slowly added into water (20 mL), extracted and separated with ethyl acetate (20 mL*3), and the organic phase was spin-dried under reduced pressure, then separated and purified by preparative HPLC (column: Waters Xbridge Prep OBD C18 (150*40 mm*10 μm); mobile phase: [water (ammonium bicarbonate)-acetonitrile]; gradient: acetonitrile %: 20%-50%, 8 min) to obtain compound WX026.

LCMS (ESI) m/z: 439.1[M+H]$^+$ $^1$H NMR (400 MHz, $D_2O$-$d_2$) δ=9.00 (s, 1H), 8.30-8.29 (m, 1H), 8.24 (s, 2H), 7.84 (s, 1H), 7.81-7.79 (m, 1H), 7.54 (s, 1H) 7.71 (s, 5H), 2.42 (s, 3H).

Embodiment 27: Synthesis of Compound WX027

WX027

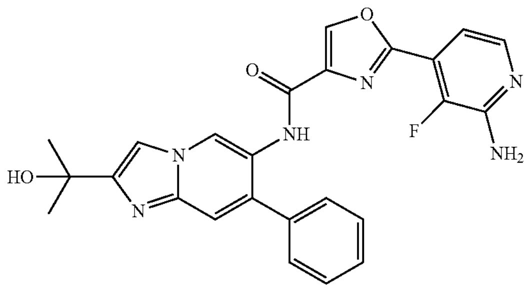

Synthetic Route:

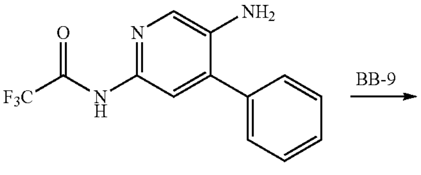

22-2

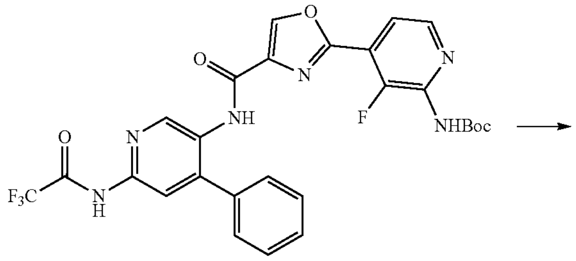

27-1

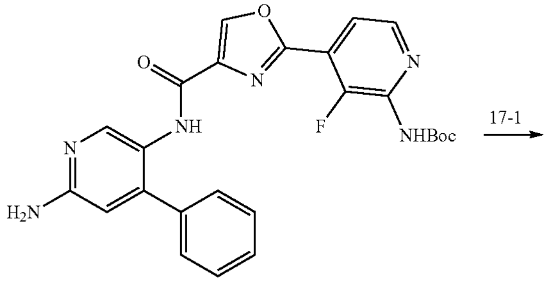

27-2

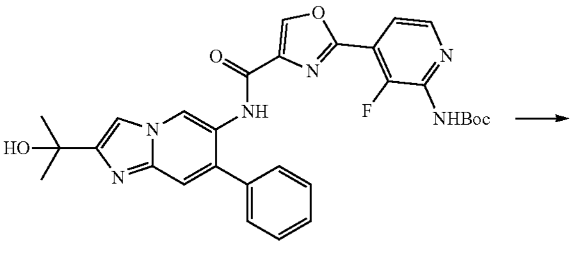

27-3

-continued

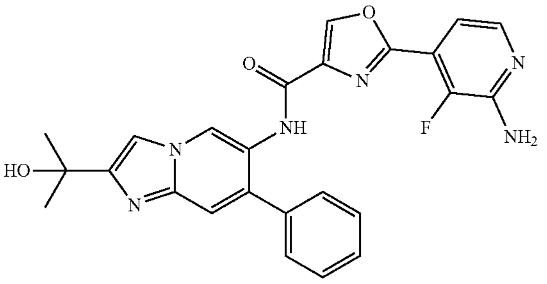

WX027

Step 1: Synthesis of Compound 27-1

Compound BB-9 (0.44 g), compound 22-2 (459.33 mg), N,N dimethylformamide (5 mL), 2-(7-azobenzotriazole)-N, N,N,N-tetramethyluronium hexafluorophosphate (776.28 mg), diisopropylethylamine (527.71 mg) were added to the reaction flask and reacted at 40° C. for 12 h. The reaction solution was added with saturated ammonium chloride solution (15 mL), stirred for 10 min, filtered, and the filter cake was concentrated to remove water to obtain the crude compound 27-1.

LCMS: m/z (ESI)=587.2[M+H]$^+$

Step 2: Synthesis of Compound 27-2

Compound 27-1 (0.7 g), methanol (15 mL), and potassium carbonate (412.40 mg) were added to the reaction flask and reacted at 60° C. for 1 h. The reaction solution was added with water (20 mL) and solids were precipitated, after filtration, and the filter cake was concentrated to remove water to obtain the crude product, and the crude product was separated and purified by silica gel column chromatography (eluent: dichloromethane:methanol=96:4 to 95:5 to 90.10) to give compound 27-2.

LCMS: m/z (ESI)=491.1[M+H]$^+$

Step 3: Synthesis of Compound 27-3

Compound 27-2 (260 mg), compound 17-1 (160.06 mg), 1,4 dioxane (3 mL), and sodium bicarbonate (111.42 mg) were added to the reaction flask and reacted at 75° C. for 3 h. Water (15 mL) was added to the reaction solution and after filtration, solids were obtained, and the filter cake was concentrated to remove water to obtain compound 27-3.

LCMS: m/z (ESI)=573.3[M+H]$^+$

Step 4: Synthesis of Compound WX027

Compound 27-3 (0.18 g), dichloromethane (2 mL) and trifluoroacetic acid (0.5 mL) were added into a reaction flask and reacted at 25° C. for 12 hours. The reaction solution was concentrated to obtain a crude product, which was separated and purified by preparative HPLC (column: Phenomenex C18 (80*30 mm*3 um); mobile phase: [water (ammonium bicarbonate)-acetonitrile]; gradient: acetonitrile %: 15%-45%, 8 min) to obtain compound WX027.

LCMS: m/z (ESI)=473.2[M+H]$^+$ $^1$H NMR (400 MHz, DMSO-d$_6$) δ=9.67 (s, 1H), 9.04 (s, 1H), 8.92 (s, 1H), 7.93-7.87 (m, 2H), 7.57-7.45 (m, 6H), 6.96-6.92 (m, 1H), 6.62 (s, 2H), 5.17-5.04 (m, 1H), 1.51 (s, 6H).

Embodiment 28: Synthesis of Compound WX028

WX028

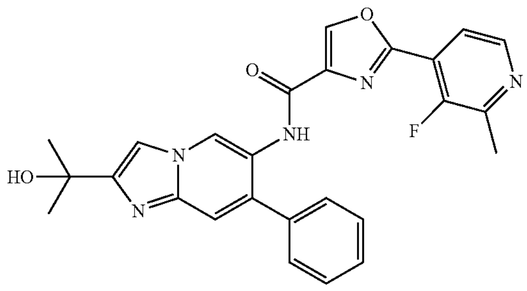

Synthetic Route:

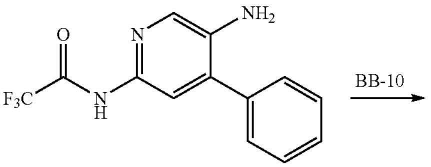

22-2

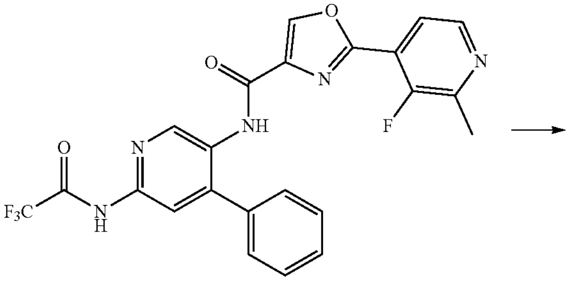

28-1

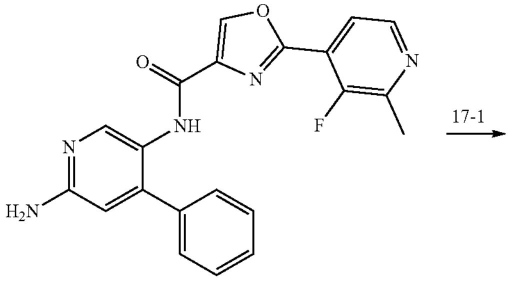

28-2

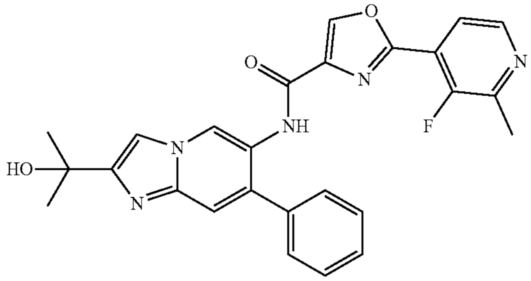

WX028

Step 1: Synthesis of Compound 28-1

Compound BB-10 (0.89 g), compound 22-2 (1.02 g), N,N dimethylformamide (10 mL), 2-(7-azobenzotriazole)-N,N,N,N-tetramethyluronium hexafluorophosphate (2.08 g), and diisopropylethylamine (1.41 g) were added to the reaction flask and reacted at 40° C. for 12 h. After the reaction, water (15 mL) was added to the reaction solution, stirred for 10 min, filtered, and the filter cake was concentrated to remove water to obtain compound 28-1.

LCMS: m/z (ESI)=486.1[M+H]$^+$ $^1$H NMR (400 MHz, DMSO-$d_6$) δ=12.17 (d, J=3.60 Hz, 1H), 9.93 (s, 1H), 9.00 (s, 1H), 8.81 (s, 1H), 8.49 (d, J=4.80 Hz, 1H), 8.00 (s, 1H), 7.76 (t, J=5.20 Hz, 1H), 7.59-7.48 (m, 5H), 2.56 (d, J=3.20 Hz, 3H).

Step 2: Synthesis of Compound 28-2

Compound 28-1 (1.1 g), methanol (15 mL) and potassium carbonate (626.41 mg) were added to the reaction flask and reacted at 25° C. for 12 hours. Water (30 mL) was added to the reaction solution, and dichloromethane (20 mL) was added for extraction and separation. The aqueous phase was extracted and separated with dichloromethane:methanol=10:1 (30 mL*3), and the organic phases were combined and concentrated to obtain compound 28-2.

LCMS: m/z (ESI)=390.1[M+H]$^+$ $^1$H NMR (400 MHz, DMSO-$d_6$) δ=9.57 (s, 1H), 8.87 (s, 1H), 8.47 (d, J=5.20 Hz, 1H), 8.03 (s, 1H), 7.78 (t, J=5.20 Hz, 1H), 7.47-7.36 (m, 5H), 6.46 (s, 1H), 6.06 (s, 2H), 2.54 (d, J=3.20 Hz, 3H).

Step 3: Synthesis of Compound WX028

Compound 28-2 (0.15 g), 1,4 dioxane (2 mL), compound 17-1 (106.18 mg) and sodium bicarbonate (82.12 mg) were added to the reaction flask and reacted at 75° C. for 3 h. The reaction solution was cooled to 25° C., added with water (15 mL) and stirred for 10 min, filtered and the filter cake was concentrated to obtain the crude product, which was added with methanol (5 mL) and stirred at 70° C. for 2 h, filtered while hot, and the filter cake was homogenized with ethanol (3 mL) at 25° C. for 1 hour and then filtered to obtain compound WX028.

MeOH=20: m/z (ESI)=472.2[M+H]$^+$ $^1$H NMR (400 MHz, DMSO-$d_6$) δ=9.71 (s, 1H), 8.98 (d, J=10.00 Hz, 2H), 8.49 (d, J=5.20 Hz, 1H), 7.85 (s, 1H), 7.74 (t, J=5.20 Hz, 1H), 7.57-7.52 (m, 2H), 7.51-7.42 (m, 4H), 5.08 (s, 1H), 2.56 (d, J=3.20 Hz, 3H), 1.51 (s, 6H).

Embodiment 29: Synthesis of Compound WX029

WX029

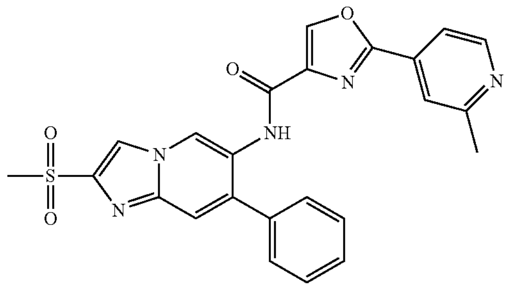

Synthetic Route:

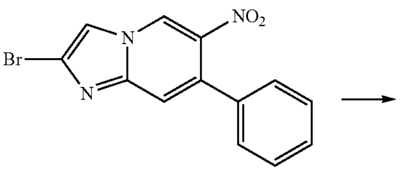

24-2

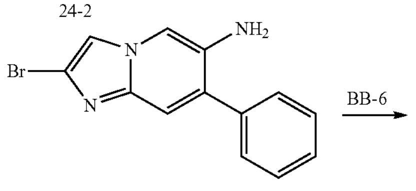

29-1

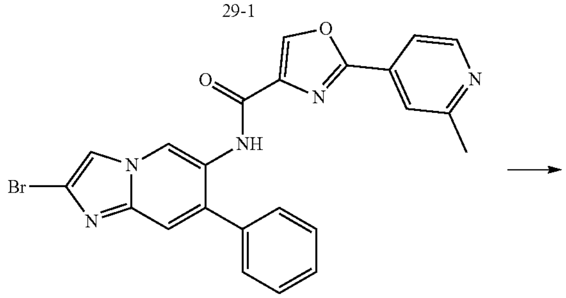

29-2

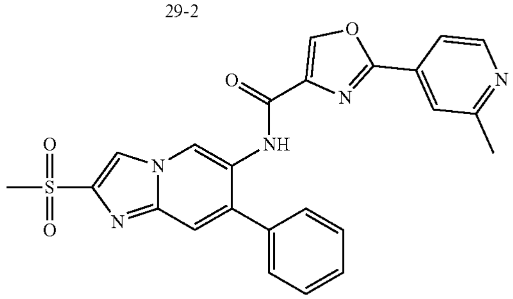

WX029

Step 1: Synthesis of Compound 29-1

Compound 24-2 (1 g) was dissolved in ethyl acetate (5 mL), and then tin dichloride dihydrate (4.26 g) was added, and the reaction was carried out at 50° C. for 16 hours. Ethyl acetate (50 mL) was added into the reaction solution, then the pH value was adjusted to 7 with 25% ammonia water, after filtration, the filtrate was concentrated under reduced pressure to obtain a crude product, and the crude product was separated and purified by silica gel column chromatography (eluent: petroleum ether:ethyl acetate=50:50 to 25:75) to obtain compound 29-1.

LCMS: m/z (ESI)=288.1[M+H]$^+$

Step 2: Synthesis of Compound 29-2

Compound 29-1 (0.7 g) was dissolved in N,N-dimethylformamide (14 mL), then 2-(7-azobenzotriazole)-N,N,N,N-tetramethyluronium hexafluorophosphate (1.39 g), diisopropylethylamine (941.93 mg) and compound BB-6 (595.24 mg) were added and the reaction solution was stirred at 40° C. for 16 h. Water (30 mL) and ethyl acetate (30 mL) were added to the reaction solution, after filtration, and the filter cake was stirred with 0.1 M aqueous sodium hydroxide (20 mL) for 0.5 h. The filter cake was concentrated under reduced pressure to remove water to obtain compound 29-2.

$^{1}$H NMR (400 MHz, $CDCl_3$) δ=9.57 (s, 1H), 9.08 (s, 1H), 8.66-8.65 (m, 1H), 8.33 (s, 1H), 7.66-7.64 (m, 4H), 7.56-7.52 (m, 4H), 7.44 (s, 1H), 2.68 (s, 3H).

Step 3: Synthesis of Compound WX029

Compound 29-2 (0.4 g) was dissolved in dimethyl sulfoxide (1 mL), then cuprous iodide (481.84 mg) and sodium methyl sulfite (258.28 mg) were added, and the reaction was carried out under microwave at 120° C. for 1 hour. Water (50 mL) was added to the reaction solution, after filtration, ethyl acetate (20 mL) was added to the filtrate, after liquid separation, and the organic phase was concentrated under reduced pressure to obtain crude compound, and the obtained crude product was separated and purified by preparative HPLC (column: Waters Xbridge BEH C18 (100*30 mm*10 Wm); mobile phase: [water (ammonium bicarbonate)-acetonitrile]; acetonitrile %: 20%-50%, 8 min) to obtain compound WX029.

LCMS: m/z (ESI)=474.2[M+H]$^+$ $^{1}$H NMR (400 MHz, $D_2O$) δ=9.02 (s, 1H), 9.37 (s, 1H), 8.30-8.28 (m, 1H), 8.21 (s, 1H), 7.81-7.77 (m, 2H), 7.54 (s, 1H), 7.21-7.16 (m, 5H), 3.07 (s, 3H), 2.41 (s, 3H).

Embodiment 30: Synthesis of Compound WX032

WX032

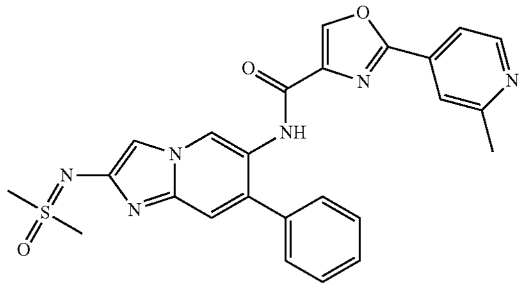

Synthetic Route:

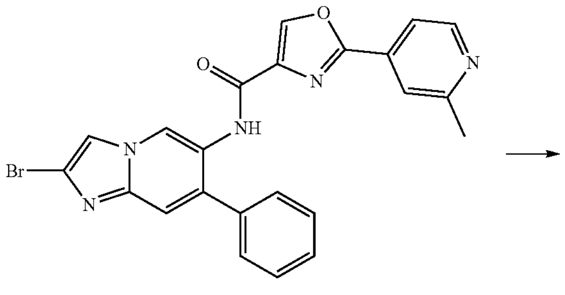

29-2

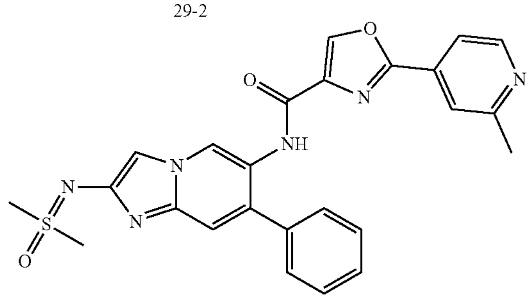

WX032

Step 1: Synthesis of Compound WX032

Compound 29-2 (0.2 g) and dimethylsulfimide (58.92 mg) were added to dioxane (4 mL), then sodium tert-butoxide (81.05 mg), 2-di-tert-butylphosphino-2',4',6'-triisopropylidene (17.91 mg) and methanesulfonic acid (2-di-tert-butylphosphino-2,4,6-triisopropyl-1,1-biphenyl) (2-amino-1,1-biphenyl-2-yl) palladium (II) (33.50 mg) were added, and the mixture was reacted at 100° C. for 16 hours. The reaction solution was added to water (50 mL), then extracted with ethyl acetate (30 mL*3), the organic phases were combined and dried with anhydrous sodium sulfate, filtered, and the filtrate was concentrated under reduced pressure. The crude product was separated and purified by preparative HPLC (column: Waters Xbridge BEH C18 (100*30 mm*10 μm); mobile phase: [water (ammonium bicarbonate)-acetonitrile]; gradient: acetonitrile %: 30%-50%, 8 min) to obtain compound WX032.

LCMS (ESI) m/z: 487.2[M+H]$^+$ $^{1}$H NMR (400 MHz, DMSO-$d_6$) δ=9.68 (s, 1H), 8.92 (s, 1H), 8.88 (s, 1H), 8.68 (s, 1H), 7.73 (s, 1H), 7.57-7.55 (m, 1H), 7.52-7.50 (m, 2H), 7.48-7.45 (m, 3H), 7.40 (s, 1H), 7.35 (s, 1H), 3.37 (s, 6H), 2.60 (s, 3H).

Embodiment 31: Synthesis of Compound WX033

WX033

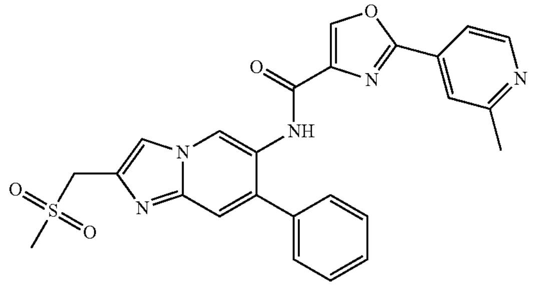

Synthetic Route:

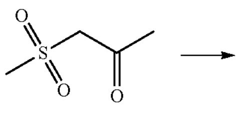

33-1

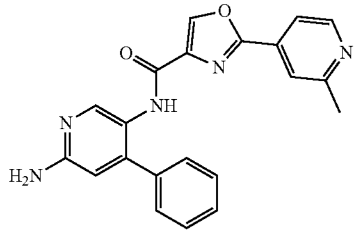

25-5

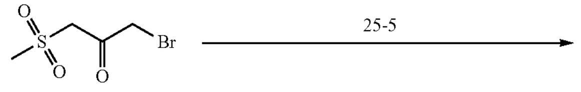

33-2

-continued

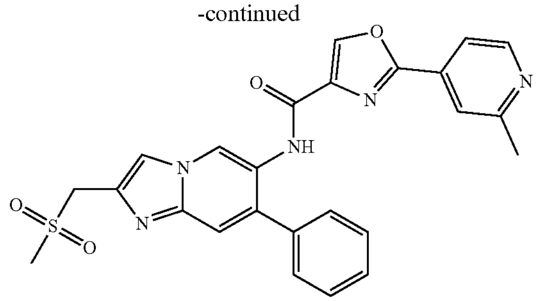

WX033

Step 1: Synthesis of Compound 33-2

Compound 33-1 (2.0 g) was dissolved in chloroform (20.0 mL), and the reaction system was replaced with nitrogen for three times, aluminum trichloride (33.33 mg) and bromine (2.58 g) were added, and the reaction solution was reacted at 25° C. for 16 hours. Water (20 mL) was added to the reaction solution, the mixture was extracted with dichloromethane (10 mL*3), the organic phases were combined, dried with anhydrous sodium sulfate, filtered by suction and concentrated under reduced pressure, and purified by column chromatography (eluent: petroleum ether:ethyl acetate=100:0 to 0:100) to obtain compound 33-2.

Step 2: Synthesis of Compound WX033

Compound 25-5 (0.1 g), compound 33-2 (86.86 mg), sodium bicarbonate (67.86 mg) and 1,4-dioxane (3 mL) were added into the reaction flask, the reaction system was replaced with nitrogen for three times, and react at 100° C. for 16 hours. The reaction solution was directly concentrated, the crude product was dissolved in methanol (5 mL) and dichloromethane (5 mL), filtered, and the filtrate was concentrated under reduced pressure to obtain the crude product, which was separated and purified by preparative HPLC (column: Phenomenex Luna C18 (75*30 mm*10 μm); mobile phase: [water (formic acid)-acetonitrile]; gradient: acetonitrile %: 1%-45%, 8 min) to obtain the compound WX033.

LCMS (ESI) m/z: 488.1 $[M+H]^+$ $^1H$ NMR (400 MHz, DMSO-$d_6$) δ=9.75 (s, 1H), 9.13 (s, 1H), 8.94 (s, 1H), 8.68-8.66 (m, 1H), 8.13 (s, 1H), 7.72 (s, 1H), 7.66-7.64 (m, 1H), 7.59-7.56 (m, 3H), 7.54-7.47 (m, 3H), 4.64 (s, 2H), 3.08 (s, 3H), 2.59 (s, 3H).

Embodiment 32: Synthesis of Compound WX036

WX036

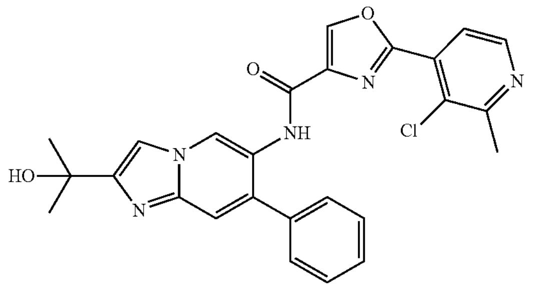

Synthetic Route:

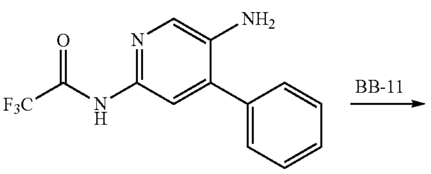

22-2

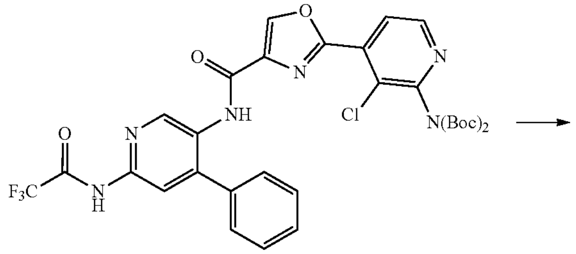

36-1

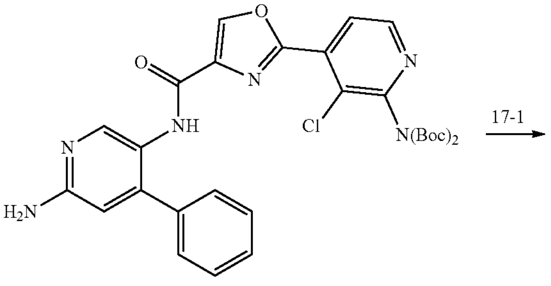

36-2

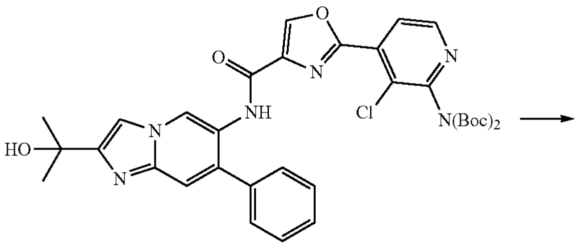

36-3

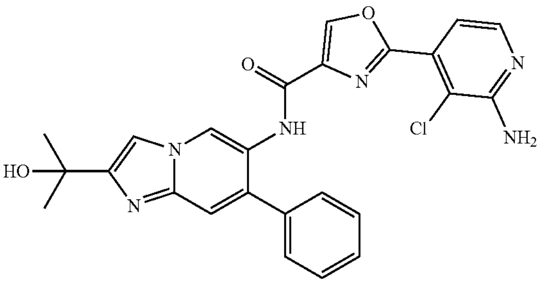

WX036

Step 1: Synthesis of Compound 36-1

Compound 22-2 (0.85 g), compound BB-11 (486.20 mg), N,N-dimethylformamide (5 mL), O-(7-azabenzotriazole-1-yl)-N,N,N,N-tetramethylurea hexafluorophosphate (1.31 g) and diisopropylethylamine (1.12 g) were added to the reaction flask and reacted at 40° C. for 12 hours. Water (20 mL) was added to the reaction solution, the mixture was stirred for 10 minutes, filtered, and the filter cake was concentrated to remove water to obtain a crude product. The crude product was separated and purified by silica gel column chromatography (gradient eluent: dichloromethane:methanol=94:6 to 91:9) to obtain compound 36-1.

LCMS: m/z (ESI)=703.2[M+H]$^+$

Step 2: Synthesis of Compound 36-2

Compound 36-1 (0.22 g), methanol (5 mL) and potassium carbonate (129.74 mg) were added to the reaction flask and reacted at 25° C. for 24 hours. Water (10 mL) was added to the reaction solution, the reaction solution was filtered, the filter cake was dissolved with dichloromethane:methanol=5:1 (30 mL), the organic phase was dried with anhydrous sodium sulfate, filtered and the filtrate was concentrated to obtain compound 36-2.

LCMS: m/z (ESI)=507.3[M+H−100]$^+$

Step 3: Synthesis of Compound 36-3

Compound 36-2 (0.122 g) 1,4-dioxane (2 mL), compound 17-1 (72.76 mg) and sodium bicarbonate (50.65 mg) were added into a reaction flask and reacted at 75° C. for 3 hours. Water (20 mL) was added to the reaction solution, dichloromethane:methanol=6:1 (70 mL*2) was added for extraction and liquid separation, the organic phases were combined, and concentrated to obtain compound 36-3.

LCMS: m/z (ESI)=589.2[M+H−100]+

Step 4: Synthesis of Compound WX036

Compound 36-3 (0.12 g) and dichloromethane (1 mL) were added to the reaction flask, and the temperature was lowered to 0° C., and trifluoroacetic acid (1 mL) was added dropwise, and the reaction was carried out at 25° C. for 12 hours. The reaction solution was concentrated to obtain a crude product, which was separated and purified by preparative HPLC (column: Phenomenex Luna C18 (75*30 mm*3 μm); mobile phase: [water (formic acid)-acetonitrile]; gradient: acetonitrile %: 1%-40%, 8 min) to obtain the compound WX036.

$^1$H NMR (400 MHz, DMSO-$d_6$) δ=9.56 (s, 1H), 9.12 (s, 1H), 8.95 (s, 1H), 8.06 (d, J=4.80 Hz, 1H), 7.90 (s, 1H), 7.57-7.53 (m, 2H), 7.51-7.44 (m, 4H), 7.02 (d, J=4.80 Hz, 1H), 6.70 (s, 2H), 5.14 (s, 1H), 1.52 (s, 6H).

Embodiment 33: Synthesis of Compound WX038

WX038

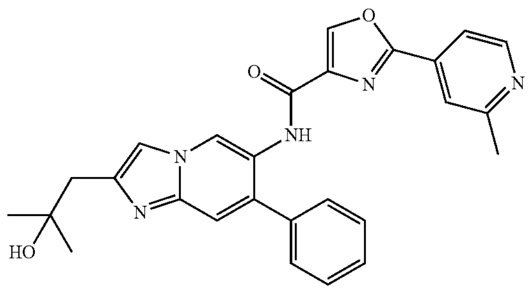

Synthetic Route:

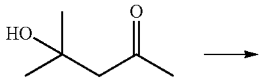

38-1

-continued

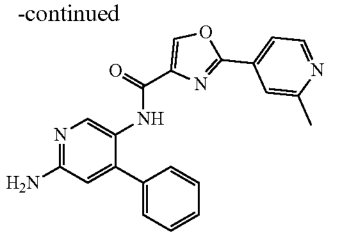

25-5

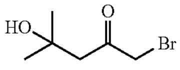

38-2

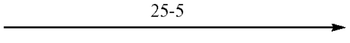

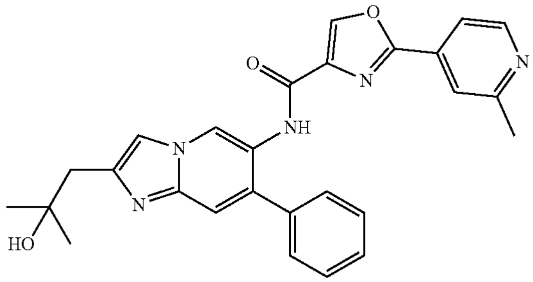

WX038

Step 1: Synthesis of Compound 38-2

Compound 38-1 (0.5 g) was added to anhydrous methanol (3 mL), then the temperature was lowered to 0° C., and then bromine (687.89 mg) was slowly added dropwise, and the reaction was continued to react at 0° C. for 3 hours. After the reaction solution was added into water (30 mL), then extracted with dichloromethane (40 mL*3), and the organic phases were combined, dried with anhydrous sodium sulfate and filtered, and the filtrate was concentrated under reduced pressure to obtain compound 38-2.

$^1$H NMR (400 MHz, $CDCl_3$) δ=3.86 (s, 2H), 2.77 (s, 2H), 1.23 (s, 6H).

Step 2: Synthesis of Compound WX038

Compound 25-5 (0.11 g) and compound 38-2 (103.99 mg) were added to anhydrous dioxane (2 mL), and then sodium bicarbonate (62.20 mg) was added and the reaction was carried out at 75° C. for 16 hours. The reaction solution was added into water (30 mL), then extracted with ethyl acetate (30 mL*3), the organic phases were combined, dried with anhydrous sodium sulfate, filtered, and the filtrate was concentrated under reduced pressure. The crude product was separated and purified by preparative HPLC (column: Waters Xbridge Prep OBD (150*40 mm*10 μm); mobile phase: [water (ammonium bicarbonate)-acetonitrile]; gradient: acetonitrile %: 30%-55%, 8 min) to obtain compound WX038.

LCMS (ESI) m/z: 468.2[M+H]$^+$ $^1$H NMR (400 MHz, DMSO) δ=9.72 (s, 1H), 9.02 (s, 1H), 8.93 (s, 1H), 8.68 (s, 1H), 7.86 (s, 1H), 7.72 (s, 1H), 7.57 (s, 1H), 7.51-7.50 (m, 2H), 7.49-7.48 (m, 4H), 4.71 (s, 1H), 2.82 (s, 2H), 2.60 (s, 3H), 1.16 (s, 6H).

Embodiment 34: Synthesis of Compound WX039
WX039
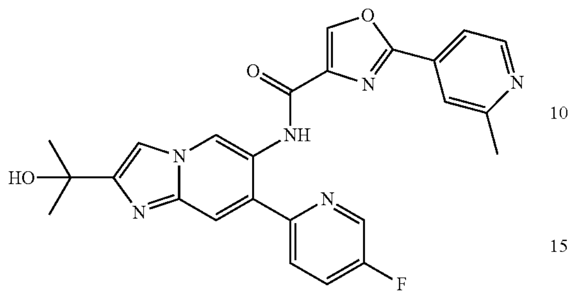
Synthetic Route:
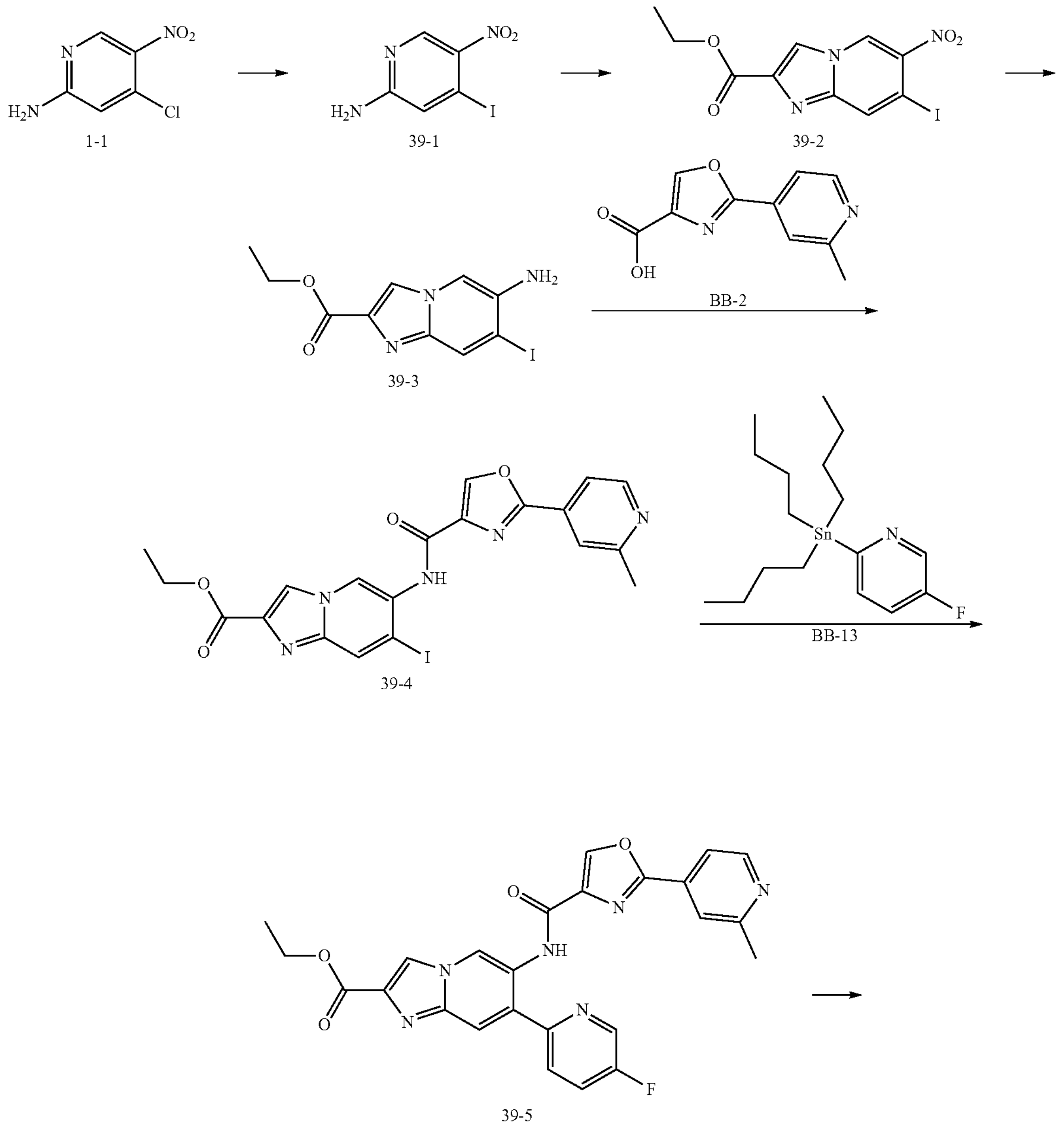

-continued

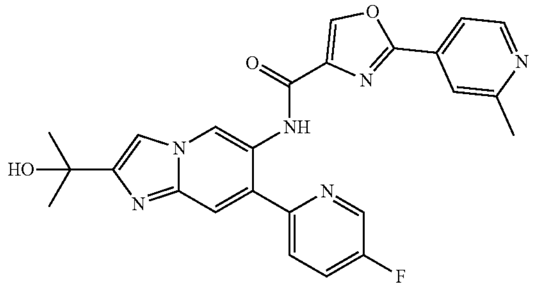

WX039

Step 1: Synthesis of Compound 39-1

Compound 1-1 (10.0 g) was dissolved in 2-butanone (100.0 mL), then hydroiodic acid (8.84 g) and sodium iodide (25.91 g) were added, and the reaction solution was stirred at 85° C. for 12 hours. The reaction solution was directly concentrated under reduced pressure, and the crude product was added with water (250.0 mL) and stirred for 15 minutes, then filtered to obtain the crude product. 15 g sodium sulfite was prepared into saturated aqueous solution, and the crude product was mixed with saturated sodium sulfite solution, stirred for 1 hour, and filtered to obtain compound 39-1.

LCMS (ESI) m/z: 265.9 $[M+H]^+$ $^1$H NMR (400 MHz, DMSO) δ=8.72 (s, 1H), 7.42 (s, 2H), 7.12 (s, 1H).

Step 2: Synthesis of Compound 39-2

Compound 39-1 (5.0 g) was added to the reaction flask and dissolved in 1,4-dioxane (75.0 mL), then ethyl bromopyruvate (5.52 g) and sodium bicarbonate (4.76 g) were added, and the reaction solution was reacted at 70° C. for 16 hours. The reaction solution was concentrated under reduced pressure, dissolved with water (50 mL) and ethyl acetate (50 mL), separated, the aqueous phase was extracted with ethyl acetate (50 mL), the organic phases were combined, dried with anhydrous sodium sulfate, filtered, and the filtrate was concentrated under reduced pressure and purified by column chromatography (eluent: petroleum ether/ethyl acetate=100:0 to 50:50) to obtain compound 39-2.

LCMS (ESI) m/z: 362.0 $[M+H]^+$

Step 3: Synthesis of Compound 39-3

Compound 39-2 (2.0 g), tin dichloride dihydrate (7.50 g) and ethyl acetate (30 mL) were added to the reaction flask, and the reaction was carried out at 50° C. for 16 hours after the reaction system was replaced with nitrogen. Ethyl acetate (30.0 mL) was added to the reaction solution, the pH value was adjusted to 7-8 with 25% ammonia water, after filtration, the filtrate was collected, concentrated under reduced pressure, and purified by column chromatography (eluent: petroleum ether/ethyl acetate=100:0 to 50:50) to obtain compound 39-3.

LCMS (ESI) m/z: 332.1 $[M+H]^+$

Step 4: Synthesis of Compound 39-4

Compound 39-3 (1.0 g), compound BB-2 (739.99 mg), N,N-diisopropylethylamine (975.83 mg), O-(7-azabenzotriazole-1-yl)-N,N,N,N-tetramethylurea hexafluorophosphate (1.72 g) and N, N-dimethylformamide (5 mL) were added into the reaction flask, the reaction was carried out at 40° C. for 16 hours after the reaction system was replaced with nitrogen. Water (10 mL) and ethyl acetate (10 mL) were added to the reaction solution, the mixture was stirred for 0.5 hour, filtered, the filter cake was collected with 0.1 M sodium hydroxide aqueous solution (20 mL), stirred for 1 hour, filtered and the filter cake was collected to obtain compound 39-4.

LCMS (ESI) m/z: 518.1 $[M+H]^+$

Step 5: Synthesis of Compound 39-5

Compound 39-4 (0.44 g), compound BB-13 (492.47 mg), bis (tri-tert-butylphosphine) palladium (43.47 mg) and dioxane (5 mL) were added into the reaction flask, the reaction system was replaced with nitrogen and reacted at 100° C. for 16 hours. The reaction solution was concentrated under reduced pressure and purified by column chromatography (eluent: petroleum ether/ethyl acetate=100:0 to 90:10) to obtain compound 39-5.

LCMS (ESI) m/z: 487.2 $[M+H]^+$

Step 6: Synthesis of Compound WX039

3 M tetrahydrofuran solution of methylmagnesium chloride (2.06 mL) was slowly added into tetrahydrofuran (4 mL) dropwise at 0° C., and then tetrahydrofuran (1 mL) solution of compound 39-5 (0.05 g) was added and the mixture was reacted at 25° C. for 1 hour. The reaction solution was slowly added into saturated ammonium chloride aqueous solution (30 mL), extracted with ethyl acetate (30 mL*3), the organic phases were combined, dried with anhydrous sodium sulfate and filtered, and the filtrate was spin-dried under reduced pressure, and the obtained crude product was separated and purified by preparative HPLC (column: Waters Xbridge Prep OBD C18 (150*40 mm*10 μm); mobile phase: [water (ammonium bicarbonate)-acetonitrile]; gradient: acetonitrile %: 10%-40%, 8 min) to obtain compound WX039.

LCMS (ESI) m/z: 473.2 $[M+H]^+$ $^1$H NMR (400 MHz, DMSO-$d_6$) δ=10.00 (s, 1H), 8.87-8.84 (m, 2H), 8.68-8.64 (m, 2H), 8.48-8.46 (m, 1H), 7.92 (s, 1H), 7.77 (s, 1H), 7.70-7.68 (m, 1H), 7.67 (s, 1H), 7.55-7.50 (m, 1H), 5.13 (s, 1H), 2.58 (s, 3H), 1.51 (s, 6H).

Biological Test Data

Test Embodiment 1: Evaluation of IRAK4 Kinase Activity In Vitro

The $IC_{50}$ values were determined using $^{33}$P isotope-labeled kinase activity assay (Reaction Biology Corp) to evaluate the inhibitory ability of the tested compounds on human IRAK4.

Buffer conditions: 20 mM Hepes (pH 7.5), 10 mM $MgCl_2$, 1 mM EGTA, 0.02% Brij35, 0.02 mg/mL BSA, 0.1 mM $Na_3VO_4$, 2 mM DTT, 1% DMSO.

Test procedure: At room temperature, the tested compound was dissolved in DMSO and a 10 mM solution was prepared for use. The substrate was dissolved in a newly prepared buffer solution, and the tested IRAK4 kinase was added thereto and mixed evenly. The DMSO solution dissolved with the tested compound was added to the above mixed evenly reaction solution using acoustic technique (Echo 550). After incubation for 15 minutes, $^{33}$P-ATP was added to initiate the reaction. The reaction was carried out at room temperature for 120 minutes, and the reaction mixture was dropped on P81 ion exchange filter paper (Whatman #3698-915). The filter paper was washed repeatedly with 0.75% phosphoric acid solution, and the radioactivity of phosphorylated substrate residues on the filter paper was determined. The kinase activity data were expressed by comparing the kinase activity of the group containing the tested compound with the kinase activity of the blank group (only containing DMSO), and the $IC_{50}$ value was obtained by curve fitting by Prism4 software (GraphPad), the experimental results were shown in Table 2.

TABLE 2

In vitro IRAK4 kinase activity screening test results of the compounds of the present disclosure

| Number of the compound | IRAK4/$IC_{50}$(nM) |
|---|---|
| WX001 | 1.8 |
| WX002 | 6.6 |
| WX003 | 0.6 |
| WX004 | 12 |
| WX005 | 1.5 |
| WX006 | 1.0 |
| WX007 | 0.4 |
| WX008 | 4.3 |
| WX009 | 0.9 |
| WX010 | 2.1 |
| WX011 | 4.7 |
| WX012 | 0.4 |
| WX013 | 1.8 |
| WX014 | 2.5 |
| WX015 | 0.4 |
| WX016 | 2.0 |
| WX017 | 0.1 |
| WX018 | 5.1 |
| WX021 | 0.3 |
| WX022 | 0.1 |
| WX023 | 0.1 |
| WX025 | 0.1 |
| WX027 | 0.1 |
| WX028 | 0.1 |
| WX029 | 0.1 |
| WX032 | 0.9 |
| WX036 | 0.4 |
| WX038 | 0.3 |

Conclusion: The compound of the present disclosure generally exhibited good inhibitory activity against IRAK4.

Conclusion: The compound of the present disclosure generally exhibited good inhibitory activity against IRAK4.

Test Embodiment 2: Evaluation of BTK Kinase Activity In Vitro

The $IC_{50}$ values were determined using $^{33}$P isotope-labeled kinase activity assay (Reaction Biology Corp) to evaluate the inhibitory ability of the tested compounds on human BTK.

Buffer conditions: 20 mM Hepes (pH 7.5), 10 mM $MgCl_2$, 1 mM EGTA, 0.02% Brij35, 0.02 mg/mL BSA, 0.1 mM $Na_3VO_4$, 2 mM DTT, 1% DMSO.

Test procedure: At room temperature, the tested compound was dissolved in DMSO and a 10 mM solution was prepared for use. The substrate was dissolved in a newly prepared buffer solution, and the BTK kinase was added thereto and mixed evenly. The compound dissolved in DMSO was added to the kinase reaction mixture through Echo 550 (Acoustic technology; Nanoliter range). After incubation for 20 minutes at room temperature, $^{33}$P-ATP was added to initiate the reaction. The reaction was carried out at room temperature for 2 hours, and the radioactivity of the reaction solution drop was detected by filtration-binding method with P81 ion exchange filter paper. The kinase activity data were expressed by comparing the kinase activity of the group containing the tested compound with the kinase activity of the blank group (only containing DMSO), and the $IC_{50}$ value was obtained by curve fitting by Prism4 software (GraphPad), the experimental results were shown in Table 3.

TABLE 3

In vitro BTK kinase activity screening test results of the compounds of the present disclosure

| Number of the compound | BTK/$IC_{50}$(nM) |
|---|---|
| WX001 | 7.9 |
| WX003 | 15.4 |
| WX005 | 0.6 |
| WX006 | 0.7 |
| WX007 | 4.1 |
| WX008 | 71 |
| WX009 | 20.1 |
| WX010 | 21.2 |
| WX011 | 1.3 |
| WX012 | 14.4 |
| WX013 | 2.9 |
| WX014 | 0.5 |
| WX015 | 5.6 |
| WX016 | 1.6 |
| WX017 | 5.2 |
| WX021 | 19.8 |
| WX022 | 45 |
| WX023 | 1.0 |
| WX027 | 2.9 |

Conclusion: The compound of the present disclosure generally exhibited good inhibitory activity against BTK.

Conclusion: The compound of the present disclosure generally exhibited good inhibitory activity against BTK.

Test Embodiment 3: Evaluation of THP-1 Cytological Activity In Vitro

TNF-α ELISA Experiment of THP-1 Cytology

1. Experimental Materials:

THP-1 human acute single cell leukemia cells were purchased from ATCC (Cat #TIB-202) and cultured at 37° C. in 5% $CO_2$ incubator. The composition of medium was RPMI1640 (Gibco, Cat #22400-105), and the supplementary compositions were 10% FBS (Gibco, Cat #10091148); 1% PenStrep (Gibco, Cat #15140); 0.05 mM β-mercaptoethanol (Sigma, Cat #M6250).

2. Experimental Methods:

TNF-α Elisa kit was used to detect the content of TNF-α in cell culture supernatant samples. TNF-α was produced by stimulating THP-1 cells with 150 ng/mL LPS (Sigma, Cat #L6529).

THP-1 cells cultured normally at logarithmic growth period were seeded in a 96-well plate (Corning #3599) at a certain concentration ($1*10^5$/100 μL) and then put into a cell incubator for incubation. After two hours, 16.7 μL of different concentrations of the compound to be tested (8*final concentration) were added and incubated in an incubator. After one hour, 16.7 μL of 1200 ng/mL LPS was added and incubated in an incubator. After 18 hours, the culture supernatant samples were collected by centrifugation, and the content of TNF-α could be detected by TNF-α Elisa kit. Finally, OD signals (OD450-OD570) were read on envision board reader.

3. Data Analysis:

The OD450-OD570 signal value was converted into a percentage inhibition rate.

$$\text{Inhibition rate }\%=(ZPE-\text{sample})/(ZPE-HPE)*100.$$

"HPE" referred to the OD450-OD570 signal value of the control well without LPS stimulated cells, and "ZPE" referred to the OD450-OD570 signal value of the control well with LPS stimulated cells. The $IC_{50}$ value of the compound was calculated by XLFit in the excel add-in.

Equation:

$$Y=\text{Bottom}+(\text{Top}-\text{Bottom})/(1+(IC_{50}/X)^\wedge\text{HillSlope}).$$

A summary of the test results was shown in Table 4.

TABLE 4

In vitro screening test results of the compounds of the present disclosure

| Number of the compound | THP-1/$IC_{50}$(nM) |
|---|---|
| WX001 | 20 |
| WX002 | 116 |
| WX005 | 171 |
| WX006 | 94 |
| WX009 | 60 |
| WX013 | 6 |
| WX015 | 60 |
| WX017 | 15.9 |
| WX027 | 41.9 |
| WX036 | 57.1 |

Conclusion: The compound of the present disclosure generally exhibited better activity of inhibiting cell TNF-α generation in THP-1 cell activity experiment.

Conclusion: The compound of the present disclosure generally exhibited better activity of inhibiting cell TNF-α generation in THP-1 cell activity experiment.

Test Embodiment 4: Evaluation of OCI-LY10 and TMD-8 Cytological Activity In Vitro 1. Experimental Objectives:

The tumor cell lines OCI-LY10 and TMD-8 were used to detect the effect of the compound of the disclosure on inhibiting tumor cell proliferation in vitro.

2. Materials and Methods 2.1 Cell Line

OCI-LY10 human diffuse large B lymphoma cells, from Nanjing Cobioer Biotechnology Co., Ltd TMD-8 human diffuse large B lymphoma cells, from Nanjing Cobioer Biotechnology Co., Ltd 2.2 Reagents and Consumables Cell Titer Glo (Cat #G7571, Promega)

96-well Transparent bottom white cell culture plate (Cat #3610, Corning Costar)

Fetal Bovine Serum (Cat #10099-141, GIBCO)

Culture medium (Invitrogen)

Benchtop Enzyme Labeler ENVISION (PE, 2104)

3. Experimental Steps:

3.1 Reagent Preparation a). Preparation of Culture Medium

| Cell lines | Culture medium |
|---|---|
| TMD-8 | MEM + 10% FBS |
| OCI-LY10 | IMDM + 20% FBS + 55 μM 2-mercaptoethanol |

b). Preparation of Compounds

The compound was diluted with DMSO to a final concentration of 10 mM. The compound was freshly prepared and ready for use.

3.2 Experimental Process a) Logarithmic growth period cells were collected, counted, resuspended with complete culture medium, the cell concentration was adjusted to an appropriate concentration (determined according to the results of cell density optimization test), inoculated on 96-well plates, and 100 μL of cell suspension was added to each well. Cells were incubated in an incubator with 37° C., 100% relative humidity and 5% $CO_2$ for 24 hours.

b) The compound to be tested was diluted to 50 μM with culture medium and then gradient diluted for 8 times. Cells were added with 25 μL/well. The final concentrations of the compound were from 10 M to 0 M, 3-fold gradient dilution, with a total of 9 concentration points.

c) Cells were incubated in an incubator with 37° C., 100% relative humidity and 5% $CO_2$ for 72 hours;

d) 60 μL of CTG test reagent was added to the culture medium.

e) Shaked fully and reacted in the dark for 10 min. Luminescence was measured on ENVISION and the inhibition rate was calculated.

3.3 Data Processing $$\text{Cell growth inhibition rate }\%=[(RLUv-RLUs)/(RLUv-RLUb)]\times 100\%$$

RLUs: RLU (cell+compound to be tested+CTG) of sample-treated cells (sample-treated group)

RLUv: RLU (cell+DMSO+CTG) of solvent treated cells (solvent control group)

RLUb: RLU (culture medium+DMSO+CTG) of cell-free blank control (blank group)

4. Experimental Results

Experimental results were shown in Table 5.

TABLE 5

In vitro screening test results of the compounds of the present disclosure

| Number of the compound | OCI-LY10/$IC_{50}$(nM) | TMD-8/$IC_{50}$(nM) |
|---|---|---|
| WX001 | 29 | 10 |
| WX002 | 125 | / |
| WX005 | / | 325 |
| WX006 | 36 | 183 |
| WX009 | 48 | 37 |
| WX011 | 6 | 28 |
| WX012 | 20 | |
| WX013 | 8 | 20 |
| WX014 | 18 | 40 |
| WX015 | 36 | / |
| WX016 | 3 | 6 |
| WX017 | 7 | 10 |
| WX023 | 14 | / |
| WX027 | 26 | 32.2 |
| WX029 | 48 | / |
| WX036 | 15.2 | 16.7 |

Conclusion: The compounds of the present disclosure exhibited good inhibitory activity on cell proliferation in OCI-LY10 and TMD-8 cell lines, respectively.

Conclusion: The compounds of the present disclosure exhibited good inhibitory activity on cell proliferation in OCI-LY10 and TMD-8 cell lines, respectively.

Test Embodiment 5: Evaluation of OCI-LY3 Cytological Activity In Vitro

1. Experimental Objectives:

The tumor cell line OCI-LY3 was used to detect the effect of the compound of the disclosure on inhibiting tumor cell proliferation in vitro.

2. Experimental Cell Line Information and Cell Culture

The tumor cell line used in this experiment was provided by Nanjing Cobioer Biotechnology Co., Ltd. See Table 6 below for specific information.

TABLE 6

Experimental cell line information

| Cell name | Cell source | Cell culture medium |
|---|---|---|
| OCI-LY3 | Nanjing Cobioer Biotechnology Co., Ltd | IMDM + 20% FBS + 0.05 mM 2-mercaptoethanol + 1% penicillin/streptomycin |

3. Experimental Methods

The OCI-LY3 cell line was cultured in the corresponding medium at 37° C. and 5% $CO_2$, and the logarithmic growth period cells were used for experimental planking. The cells were collected and centrifuged at 800 rpm for 5 minutes, and the culture medium was re-suspended and spread in a 96-well plate. After being cultured overnight in 37° C., 5% $CO_2$ incubator, drugs with different concentration gradients (10 μL of prepared diluent of test compound was added) were added, and incubated in 37° C., 5% $CO_2$ incubator for 72 hours. The cell culture plate was incubated with CTG reagent at room temperature in the dark for 30 minutes and return to room temperature. CTG solution was added into the biosafety cabinet in the dark 100 μL/well, and was shaken and mixed evenly on plate shaker in the dark for 2 minutes, and incubated at room temperature in the dark for 10 minutes. The luminous value was read and recorded with Perkin Elmer Envision instrument.

4. Data Processing and Analysis

The luminous value of the blank control group was subtracted from the luminous value measured at each drug concentration, the ratio of this value to DMSO group was taken as the cell inhibition rate (%). GraphPad software was used, the logarithm of drug concentration (log drug concentration) versus inhibition rate was plotted, and the $IC_{50}$ value and 95% confidence value were automatically fitted and calculated by log (inhibitor) vs. response-variable slop (four parameters) algorithm of nonlinear regression by software.

5. Experimental Results

Experimental results were shown in Table 7.

TABLE 7

In vitro screening test results of the compounds of the present disclosure

| Number of the compound | OCI-LY3/ $IC_{50}$(nM) |
|---|---|
| WX001 | 57 |
| WX009 | 121 |
| WX011 | 26 |
| WX013 | 34 |
| WX014 | 41 |
| WX016 | 37 |
| WX017 | 18 |
| WX027 | 48 |
| WX036 | 42 |

Conclusion: The compound of the disclosure had a significant inhibition effect on cell proliferation on OCI-LY3 cell line.

Conclusion: The compound of the disclosure had a significant inhibition effect on cell proliferation in OCI-LY3 cell line.

Experimental Example 6: Pharmacokinetic Study of Mice

Experimental Objectives:

The purpose of this experiment was to study the pharmacokinetics of the test compound in the plasma of CD-1 male mice after intravenous injection and oral administration.

Experimental Operation:

Intravenous injection group: the tested compound was weighed and dissolved with 5% DMSO/10% Solutol/85% $H_2O$, and the pH was adjusted to 4-5 with 6M hydrochloric acid, and a clear solution of 1.5 mg/mL was prepared by vortex, which was filtered by 0.22 m microporous membrane for later use. CD-1 male mice from 6 to 10 weeks old were selected and the test compound solution was injected intravenously at a dose of 3 mg/kg. The sample collection time was: 0.083, 0.25, 0.5, 1, 2, 4, 6, 8, 24 hours.

Oral administration group: the tested compound was weighed and dissolved with 5% DMSO/10% Solutol/85% $H_2O$, the pH was adjusted to 3-4 with 6M hydrochloric acid, and a clear solution of 2.0 mg/mL was prepared by vortex for later use. CD-1 male mice from 6 to 10 weeks old were selected and the test compound was administered orally at a dose of 10 mg/kg. The sample collection time was: 0.25, 0.5, 1, 2, 4, 6, 8, 10, 24 hours.

Approximately 50 μL of whole blood was collected through the jugular vein at each time point for plasma preparation for concentration determination by high performance liquid chromatography-tandem mass spectrometry (LC-MS/MS). All animals were euthanized by $CO_2$ anesthesia after collecting PK samples at the last time point. The non-atrioventricular model of WinnonLin™ Version 6.3 (Pharsight, Mountain View, CA) pharmacokinetic software was used to process the plasma concentration, and the pharmacokinetic parameters were calculated by linear logarithmic trapezoid method. The experimental results were shown in Table 8.

TABLE 8

Pharmacokinetic results of the tested compounds

| Dose | Pharmacokinetic parameters | Compound WX009 | Compound WX017 | Compound WX027 |
|---|---|---|---|---|
| IV | Half-life $T_{1/2}$ (h) | 8.1 | 2.3 | 1.9 |
| | Clearance rate CL (ml/min/kg) | 5.9 | 15.1 | 28.2 |
| | Apparent volume of distribution Vdss (L/kg) | 1.5 | 0.5 | 0.8 |

TABLE 8-continued

| Pharmacokinetic results of the tested compounds | | | | |
|---|---|---|---|---|
| Dose | Pharmacokinetic parameters | Compound WX009 | Compound WX017 | Compound WX027 |
| | Area under the plasma concentration-time curve $AUC_{0-24h}$ (nM · h) | 17877 | 7672 | 3766 |
| PO | Peak time $T_{max}$ (h) | 0.5 | 0.8 | 0.3 |
| | Peak concentration $C_{max}$ (nM) | 17800 | 6520 | 4930 |
| | Area under the plasma concentration-time curve AUC (nM · h) | 47983 | 10432 | 8079 |
| | Bioavailability (%) | 78% | 41% | 64% |

Conclusion: The pharmacokinetic study of the present disclosure in CD-1 mice showed a low drug clearance rate, and after oral administration, the peak could be quickly reached, and showed a high oral absorption bioavailability.

Conclusion: The pharmacokinetic study of the compound of the present disclosure in CD-1 mice showed a low drug clearance rate, and after oral administration, the peak could be quickly reached, and showed a high oral absorption bioavailability.

Experimental Example 7: Pharmacokinetics of Rats

Experimental Objectives:

The purpose of this experiment was to study the pharmacokinetics of the tested compound in the plasma of SD male rats after intravenous injection and oral administration.

Experimental Operation:

SD male rats from 7 to 10 weeks old were selected, and the dosage of intravenous and oral administration was 1 mg/kg and 3 mg/kg respectively. Rats in the gavage group fasted for at least 12 hours before administration, and feeding was resumed after administration for 4 hours. Intravenous injection group was free to eat and drink during the whole experiment.

Drug preparation operation: in the intravenous injection group, the compound was weighed and dissolved with 5% DMSO/10% Solutol/85% $H_2O$, and a clear solution of 0.5 mg/mL was prepared by vortex, which was filtered by a 0.22 m microporous membrane for later use. In the gavage group, the compound was dissolved in 5% DMSO/10% Solutol/85% $H_2O$, and a uniform suspension was prepared by vortex. On the day of the experiment, the animals in the intravenous group were given the corresponding compound by a single injection through the tail vein, and the dosage volume was 2 mL/kg. In the oral group, the corresponding compounds were given by single gavage, and the dosage volume was 5 mL/kg. The animals before administration were weighed, and the administration volume was calculated according to the weight. The sampling time was 0.083 (injection group), 0.25, 0.5, 1, 2, 4, 6, 8, 10 (gavage group), 24 hours. Approximately 250 μL of whole blood was collected through the jugular vein at each time point for plasma preparation for concentration determination by high performance liquid chromatography-tandem mass spectrometry (LC-MS/MS). All animals were euthanized by $CO_2$ anesthesia after collecting PK samples at the last time point. The non-atrioventricular model of WinnonLin™ Version 6.3 (Pharsight, Mountain View, CA) pharmacokinetic software was used to process the plasma concentration, and the pharmacokinetic parameters were calculated by linear logarithmic trapezoid method. The experimental results were shown in Table 9.

TABLE 9

| Pharmacokinetic results of compounds | | | | |
|---|---|---|---|---|
| Dose | Pharmacokinetic parameters | Compound WX009 | Compound WX017 | Compound WX027 |
| IV | Half-life $T_{1/2}$ (h) | 2.5 | 4.1 | 1.4 |
| | Clearance rate CL (ml/min/kg) | 1.1 | 7.0 | 4.0 |
| | Apparent volume of distribution Vdss (L/kg) | 0.2 | 0.8 | 0.3 |
| | Area under the plasma concentration-time curve $AUC_{0-24h}$ (nM · h) | 35541 | 5513 | 8838 |
| PO | Peak time $T_{max}$ (h) | 1.3 | 0.8 | 0.3 |
| | Peak concentration $C_{max}$ (nM) | 10080 | 1016 | 4329 |
| | Area under the plasma concentration-time curve AUC (nM · h) | 59138 | 4769 | 10168 |
| | Bioavailability (%) | 55% | 29% | 38% |

Conclusion: The pharmacokinetic study of the compound of the present disclosure in SD rats showed a low drug clearance rate, and after oral administration, the peak could be quickly reached, and showed a high oral absorption bioavailability.

Conclusion: The pharmacokinetic study of the compound of the present disclosure in SD rats showed a low drug clearance rate, and after oral administration, the peak could be quickly reached, and showed a high oral absorption bioavailability.

Experimental Example 8: Activity Evaluation of TNF-α Secretion Model Induced by LPS in SD Rats 1. Experimental Objectives:

a) The pharmacokinetic effect of compound WX009 on TNF-α secretion model induced by LPS in SD rats.

2. Materials and Method

Female SD rats were randomly divided into four groups according to the animal weight, namely Sham group, Model group and Dexamethasone (dosage: 0.5 mpk, DEX-0.5 mpk) group and tested drug WX009 (dosage: 25 mpk, WX009-25 mpk) group, with 6-9 animals in each group. The model was established by a single intraperitoneal injection of 1 mg/kg LPS. Dexamethasone and tested drug were given orally by gavage 0.5 h before modeling. After modeling for 2 hours, the animals were weighed, and all the experimental animals were anesthetized by intraperitoneal injection of pentobarbital sodium. An anticoagulant whole blood was collected through sublingual vein, anticoagulant: EDTA-K2, the plasma was separated, and the plasma volume was about 200 μL, which was used to detect the content of inflammatory factor, TNF-α.

3. Results

At the end of the experiment, the test results of TNF-α concentration in animal plasma were showed (FIG. 1). Compared with the Sham group, the TNF-α content in the plasma in the Model group increased significantly ($p<0.001$). Compared with the Model group, the TNF-α content in the plasma in Dexamethasone-0.5 mpk group decreased significantly ($p<0.01$). The tested compound WX009-25 mpk group could significantly reduce the content of TNF-α in animal plasma, with significant statistical difference ($p<0.01$).

Experimental Example 9: Pharmacodynamic Study of Test Compound WX009 on Subcutaneous Xenograft Tumor Model of Human Diffuse Large B Lymphoma TMD8 Cells In Vivo 1. Purpose of the Experiment The antitumor effects of the compounds ibrutinib, BAY-1, ibrutinib in combination with BAY-1, and WX009 at high, medium, and low doses were evaluated using in vivo efficacy of human diffuse large B lymphoma TMD8 cell subcutaneous xenografts in a female SCID mouse model.

2. Experimental Methods:

2.1 Modeling

TMD8 cells were cultured in RPMI-1640 medium containing 10% FBS and maintained in a 37° C. saturated humidity incubator with 5% $CO_2$. TMD8 cells in logarithmic period were collected, resuspended in RPMI-1640 basal medium, and Matrigel was added at 1:1, and the cell concentration was adjusted to $4\times10^7$/mL. Under aseptic conditions, 0.1 mL of cell suspension was inoculated under the skin of the right back of SCID mice, and the inoculation concentration was $4\times10^6$/0.1 mL/mouse.

2.2 Grouping and Drug Administration Observation

When the tumor grew to a certain size, the animals with too large, too small or irregular tumor shape were excluded, and the animals with tumor volume of 100.72-184.05 $mm^3$ were selected. According to the tumor volume, the animals were divided into 7 groups by random block method, with 8 mice in each group, and the average tumor volume was about 140.82 $mm^3$. The health status and death of animals were monitored every day, and routine examinations included observing the effects of tumor growth and drug treatment on daily behaviors of animals, such as behavioral activities, food intake and water intake, weight change (weight was measured twice a week), tumor size (tumor volume was measured twice a week), appearance signs or other abnormal conditions.

TABLE 10

Research scheme of human diffuse large B lymphoma TMD8 SCID mouse xenograft tumor model

| Group | Test compound | Number of animals | Dose (mg/kg) | Route of administration | Frequency of administration |
|---|---|---|---|---|---|
| 1 | Vehicle | 8 | / | PO | QD |
| 2 | ibrutinib | 8 | 20 | PO | QD |
| 3 | BAY-1 | 8 | 50 | PO | QD |
| 4 | BAY-1 in combination of ibrutinib | 8 | 50<br>20 | PO<br>PO | QD<br>QD |
| 5 | WX009 | 8 | 20 | PO | BID |
| 6 | WX009 | 8 | 10 | PO | BID |
| 7 | WX009 | 8 | 5 | PO | BID |

2.3 Evaluation Indicator

The formula for calculating tumor volume (TV) was: ½×a×$b^2$, where a and b were the measured length and width of the tumor respectively. The formula for calculating the tumor inhibition rate TGI (%)=[1−(average tumor volume at the end of administration in a treatment group-average tumor volume at the beginning of administration in the treatment group))/(average tumor volume at the end of treatment in solvent control group-average tumor volume at the beginning of treatment in solvent control group)]×100%.

2.4 Data Analysis:

In this study, the experimental data were all expressed by Mean±SEM. Statistical analysis was based on the data of RTV at the end of the experiment and analyzed by IBM SPSS Statistics software. T test was used to analyze the comparison between two groups, and one-way ANOVA was used to analyze the comparison between three or more groups. If the variance was even (there was no significant difference in F value), Tukey's method was used to analyze it, and if the variance was uneven (there was significant difference in F value), Games-Howell method was used to test it. $p<0.05$ was deemed to a significant difference.

3. Experimental Results and Discussion

Figure 2:
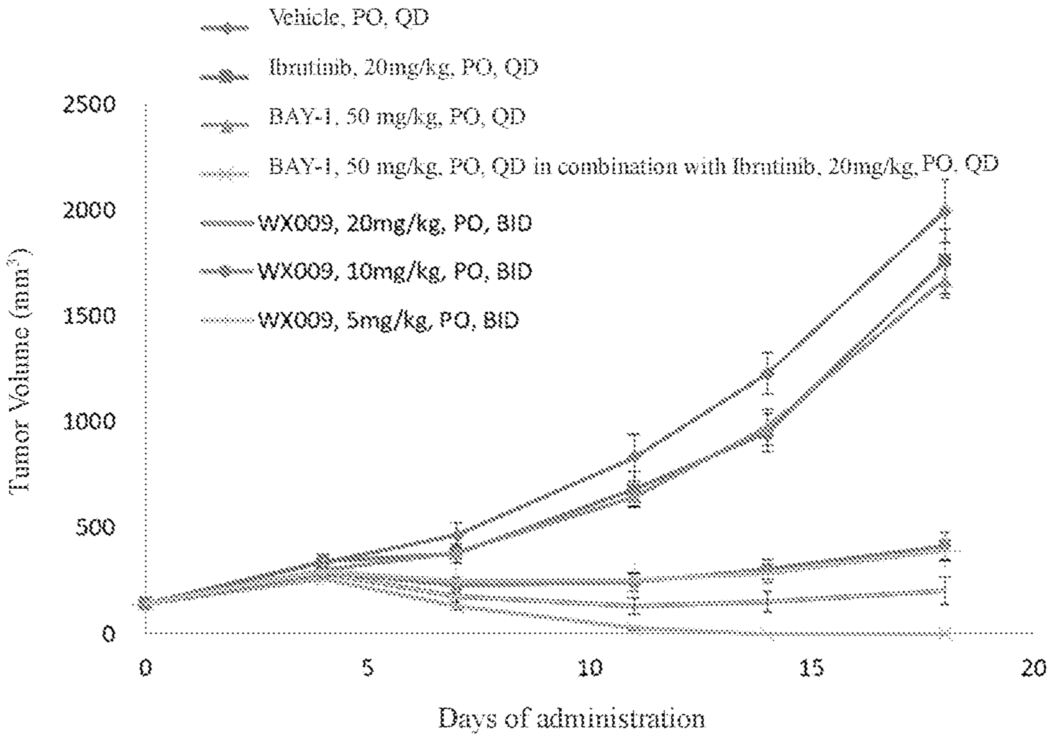
FIG. 2 shows the tumor growth curve of human diffuse large B lymphoma TMD8 cell subcutaneous xenograft tumor model tumor bearing mice after administration of the test compound WX009.

This experiment evaluated the efficacy of compound ibrutinib, BAY-1, BAY-1 in combination with ibrutinib and WX009 at high, medium, and low doses in subcutaneous xenograft tumor of human diffuse large B lymphoma TMD8 cells in female SCID mouse model. In this experiment, the average body weight of animals in all experimental groups did not decrease significantly during the whole administration period, and the mice were well tolerated. The experimental results were shown in Table 11 and FIG. 2.

TABLE 11

Evaluation of the antitumor efficacy of the compound in the subcutaneous xenograft tumor model of human diffuse large B lymphoma TMD8 cells (Calculated based on tumor volume on 18th day after administration)

| Test compound | TGI (%) |
|---|---|
| Vehicle | — |
| ibrutinib 20 mg/kg QD | 12.95 |
| BAY-1 50 mg/kg QD | 17.65 |
| BAY-1 50 mg/kg QD in combination with ibrutinib 20 mg/kg QD | 107.56 |
| WX009 20 mg/kg BID | 96.55 |
| WX009 10 mg/kg BID | 85.10 |
| WX009 5 mg/kg BID | 86.28 |

Experimental conclusion: In the low-dose group of IRAK4 and BTK double-target inhibitor WX009, a single drug of 5 mg/kg (BID) showed significant antitumor effect (TGI=86%), which was significantly better than the single drug efficacy of BTK inhibitor Ibrahim (20 mg/kg, QD) (TGI=13%) and the single drug efficacy of IRAK4 inhibitor BAY-1 (50 mg, QD) (TGI=18%), and showed the remarkable effect of simultaneous inhibition of IRAK4 and BTK.

Experimental Example 10: Pharmacodynamic Study of Test Compound WX017 and WX027 on Subcutaneous Xenograft Tumor Model of Human Diffuse Large B Lymphoma TMD8 Cells In Vivo 1. Purpose of the Experiment The antitumor effects of the compounds ibrutinib, BAY-1, ibrutinib in combination with BAY-1, and WX017 and WX027 at high, medium, and low doses were evaluated using in vivo efficacy of human diffuse large B lymphoma TMD8 cell subcutaneous xenografts in a female SCID mouse model.

2. Experimental Methods:

2.1 Modeling a) TMD8 cells were cultured in RPMI-1640 medium containing 10% FBS and maintained in a 37° C. saturated humidity incubator with 5% $CO_2$. TMD8 cells in logarithmic period were collected, resuspended in RPMI-1640 basal medium, and Matrigel was added at 1:1, and the cell concentration was adjusted to $4\times10^7$/mL. Under aseptic conditions, 0.1 mL of cell suspension was inoculated under the skin of the right back of SCID mice, and the inoculation concentration was $4\times10^6$/0.1 mL/mouse.

2.2 Grouping and Drug Administration Observation

When the tumor grew to a certain size, the animals with too large, too small or irregular tumor shape were excluded, and the animals with tumor volume of 108.76-188.11 $mm^3$ were selected. According to the tumor volume, the animals were divided into 10 groups by random block method, with 6 mice in each group, and the average tumor volume was about 152.11 $mm^3$. The health status and death of animals were monitored every day, and routine examinations included observing the effects of tumor growth and drug treatment on daily behaviors of animals, such as behavioral activities, food intake and water intake, weight change (weight was measured twice a week), tumor size (tumor volume was measured twice a week), appearance signs or other abnormal conditions.

TABLE 12

Research scheme of human diffuse large B lymphoma TMD8 SCID mouse xenograft tumor model

| Group | Test compound | Number of animals | Dose (mg/kg) | Route of administration | Frequency of administration |
|---|---|---|---|---|---|
| 1 | Vehicle | 6 | / | PO | QD |
| 2 | ibrutinib | 6 | 20 | PO | QD |
| 3 | BAY-1 | 6 | 50 | PO | QD |
| 4 | BAY-1 in combination of ibrutinib | 6 | 50<br>20 | PO<br>PO | QD<br>QD |
| 5 | WX017 | 6 | 3 | PO | BID |
| 6 | WX017 | 6 | 10 | PO | BID |
| 7 | WX017 | 6 | 20 | PO | BID |
| 8 | WX027 | 6 | 3 | PO | BID |
| 9 | WX027 | 6 | 10 | PO | BID |
| 10 | WX027 | 6 | 20 | PO | BID |

2.3 Evaluation Indicator

The formula for calculating tumor volume (TV) was: $\frac{1}{2}\times a\times b^2$, where a and b were the measured length and width of the tumor respectively. The formula for calculating the tumor inhibition rate TGI (%)=[1−(average tumor volume at the end of administration in a treatment group-average tumor volume at the beginning of administration in the treatment group))/(average tumor volume at the end of treatment in solvent control group-average tumor volume at the beginning of treatment in solvent control group)]×100%.

2.4 Data Analysis:

In this study, the experimental data were all expressed by Mean±SEM. Statistical analysis was based on the data of RTV at the end of the experiment and analyzed by IBM SPSS Statistics software. T test was used to analyze the comparison between two groups, and one-way ANOVA was used to analyze the comparison between three or more groups. If the variance was even (there was no significant difference in F value), Tukey's method was used to analyze it, and if the variance was uneven (there was significant difference in F value), Games-Howell method was used to test it. $p<0.05$ was deemed to a significant difference.

3. Experimental Results and Discussion

Figure 3:
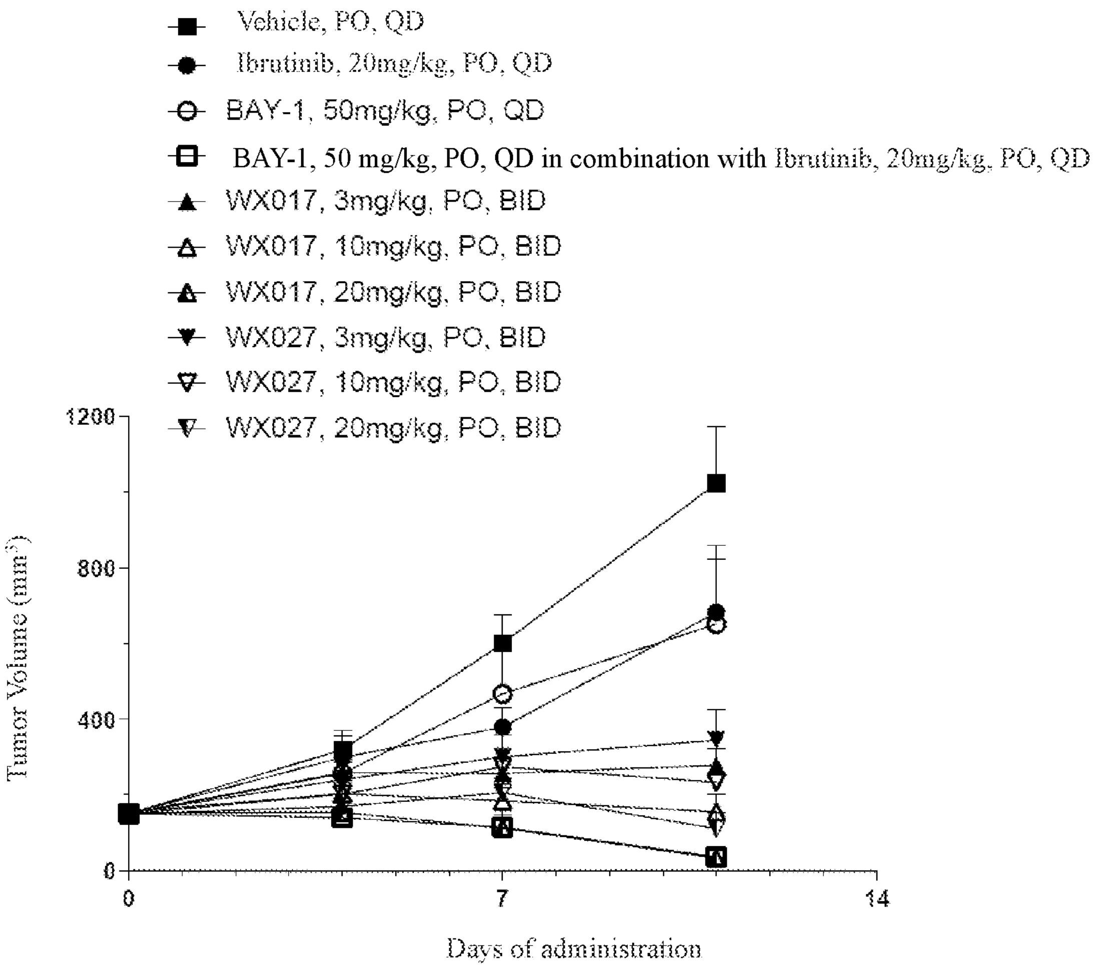
FIG. 3 shows the tumor growth curve of human diffuse large B lymphoma TMD8 cell subcutaneous xenograft tumor model tumor bearing mice after administration of the test compounds WX017 and WX027.

This experiment evaluated the efficacy of compound ibrutinib, BAY-1, BAY-1 in combination with ibrutinib and WX017 and WX027 at high, medium, and low doses in subcutaneous xenograft tumor of human diffuse large B lymphoma TMD8 cells in female SCID mouse model. In this experiment, the average body weight of animals in all experimental groups did not decrease significantly during the whole administration period, and the mice were well tolerated. The experimental results were shown in Table 13 and FIG. 3.

TABLE 13

Evaluation of the antitumor efficacy of the compound in the subcutaneous xenograft tumor model of human diffuse large B lymphoma TMD8 cells (Calculated based on tumor volume on 11th day after administration)

| Test compound | TGI (%) |
|---|---|
| Vehicle | — |
| ibrutinib 20 mg/kg QD | 39 |
| BAY-1 50 mg/kg QD | 43 |
| BAY-1 50 mg/kg QD in combination with ibrutinib 20 mg/kg QD | 113 |
| WX017 3 mg/kg BID | 86 |
| WX017 10 mg/kg BID | 100 |
| WX017 20 mg/kg BID | 114 |
| WX027 3 mg/kg BID | 78 |
| WX027 10 mg/kg BID | 90 |
| WX027 20 mg/kg BID | 104 |

Experimental conclusion: In the low-dose group of IRAK4 and BTK double-target inhibitor WX017 and WX027, a single drug of 3 mg/kg (BID) showed significant antitumor effect (TGI=86% and 78% respectively), which was significantly better than the single drug efficacy of BTK inhibitor Ibrahim (20 mg/kg, QD) (TGI=39%) and the single drug efficacy of IRAK4 inhibitor BAY-1 (50 mg, QD) (TGI=43%), and showed the remarkable effect of simultaneous inhibition of IRAK4 and BTK.

The invention claimed is:

1. A compound represented by formula (II-1), formula (II-2), formula (II-3) or formula (I), or a pharmaceutically acceptable salt thereof, (II-1)

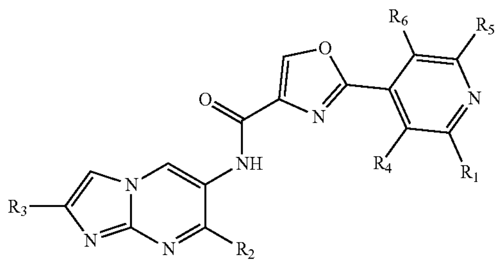

(II-2)

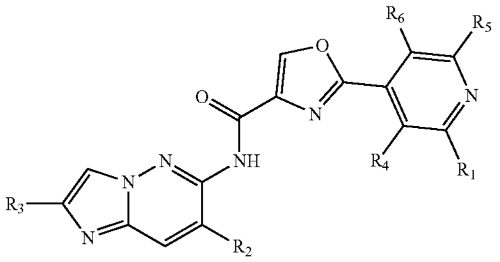

and

-continued (II-3)

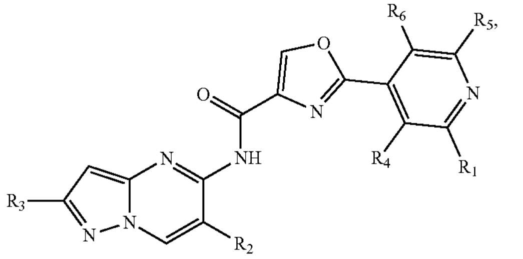

(I)

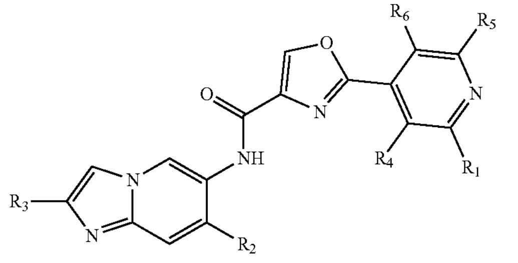

wherein, $R_1$ is selected from the group consisting of H, F, Cl, Br, I, OH, CN, —$NR_aR_b$, $CH_3$, —C(=O)—$C_{1-3}$ alkyl and $C_{1-3}$ alkoxy, and the $C_{1-3}$ alkyl and $C_{1-3}$ alkoxy are independently and optionally substituted with 1, 2 or 3 halogens;

$R_4$ is selected from the group consisting of H, F, Cl, Br, I, OH, CN, —$NR_aR_b$, $C_{1-3}$ alkyl and —C(=O)—$C_{1-3}$ alkyl, and the $C_{1-3}$ alkyl is optionally substituted with 1, 2 or 3 halogens;

or, $R_1$ and $R_4$ are attached to form pyrrolyl with the attached atoms;

$R_2$ is selected from the group consisting of

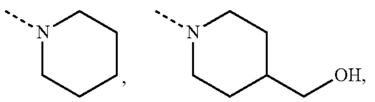

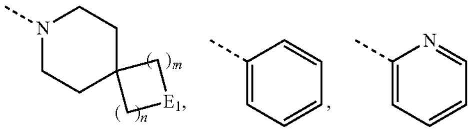

and

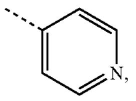

and the

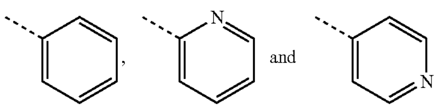

are optionally substituted with one F;

$R_3$ is selected from the group consisting of

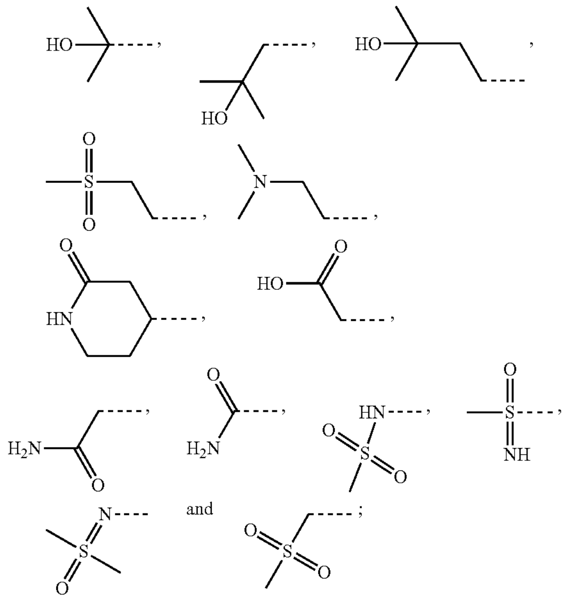

$E_1$ is selected from the group consisting of NH, O and S;

$R_5$ and $R_6$ are independently selected from the group consisting of H, F, Cl, Br, I, OH, CN, —C(=O)—$C_{1-3}$ alkyl and $C_{1-3}$ alkyl, and the $C_{1-3}$ alkyl is optionally substituted with 1, 2 or 3 halogens;

m is 1 or 2;

n is 1 or 2;

$R_a$ is independently selected from the group consisting of H and $C_{1-3}$ alkyl; and $R_b$ is independently selected from the group consisting of H, $C_{1-3}$ alkyl and —C(=O)—$C_{1-3}$ alkyl.

2. A compound represented by the following formula or a pharmaceutically acceptable salt thereof, wherein the compound is selected from:

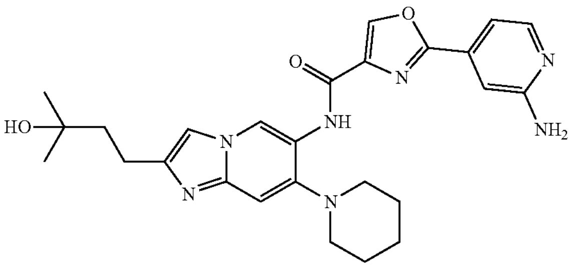

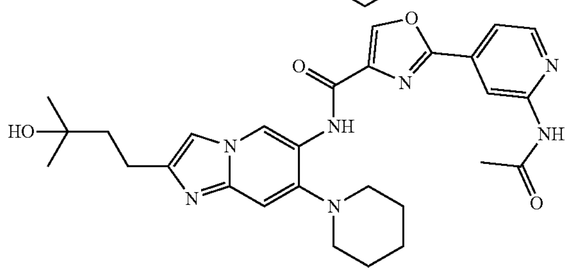

-continued
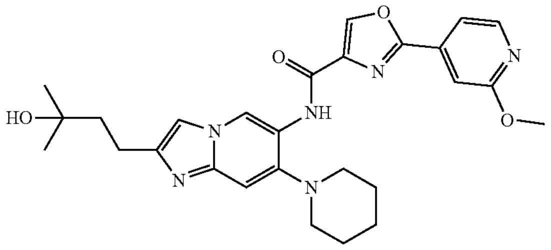
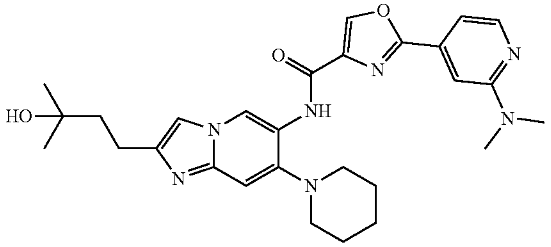
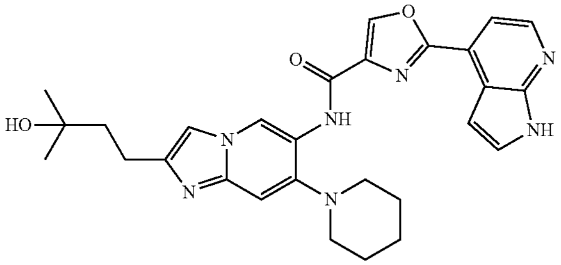
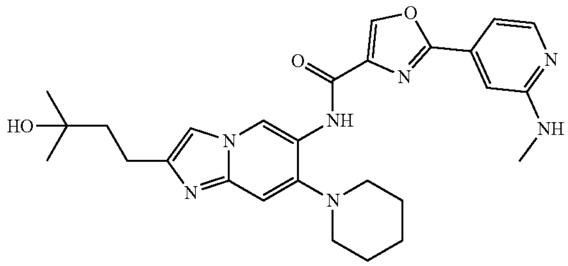
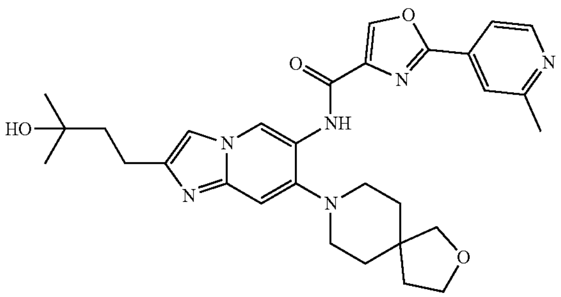
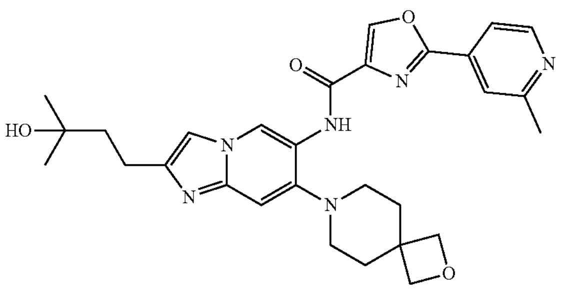
-continued
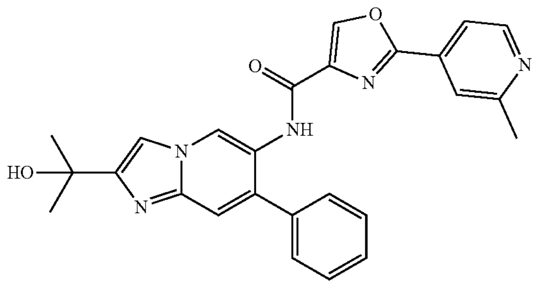
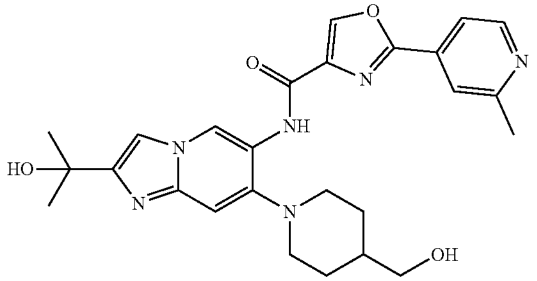
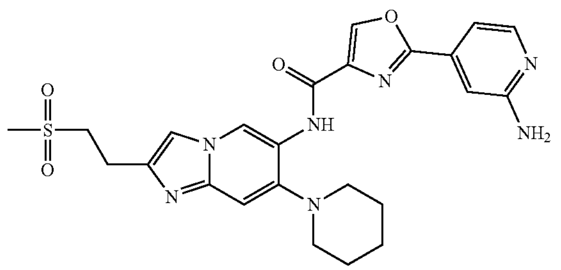
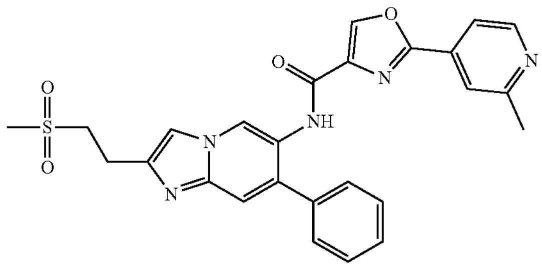
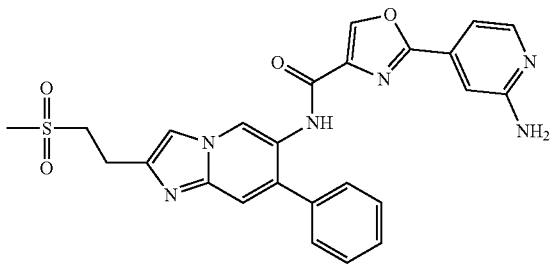
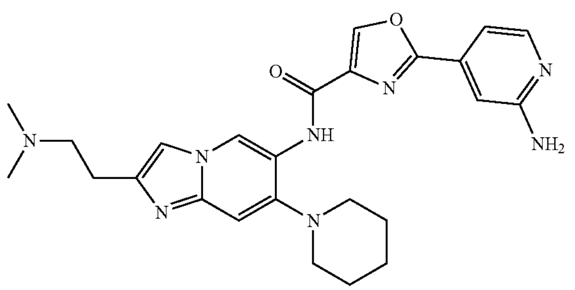

-continued
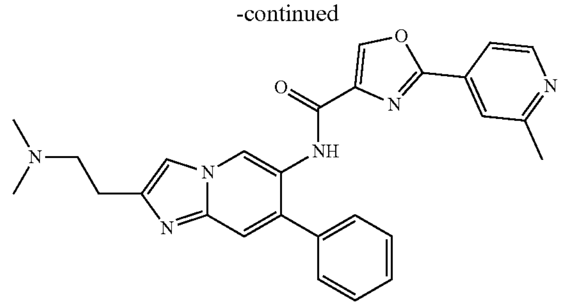
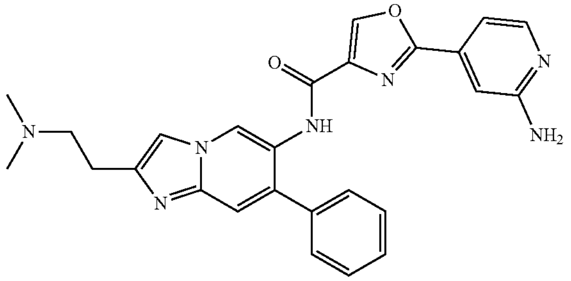
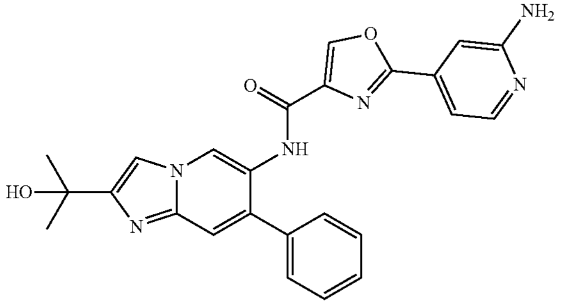
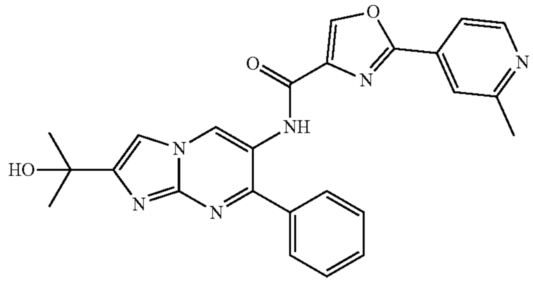
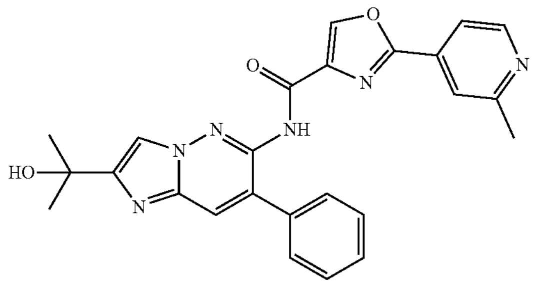
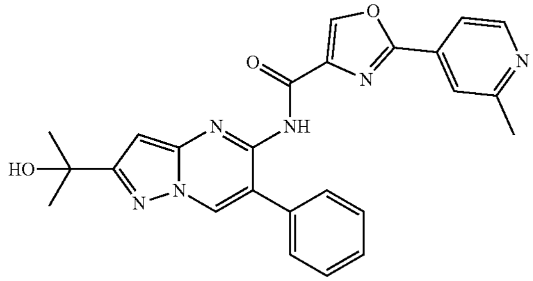
-continued
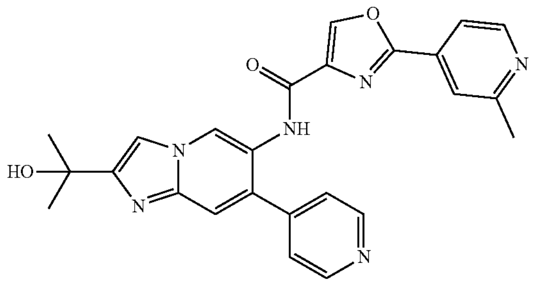
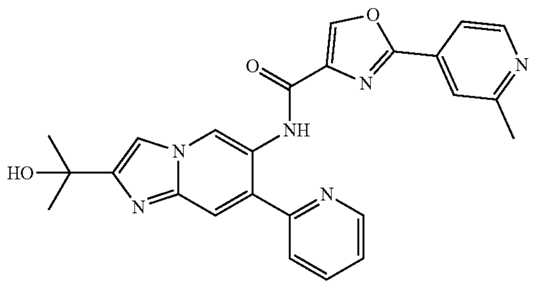
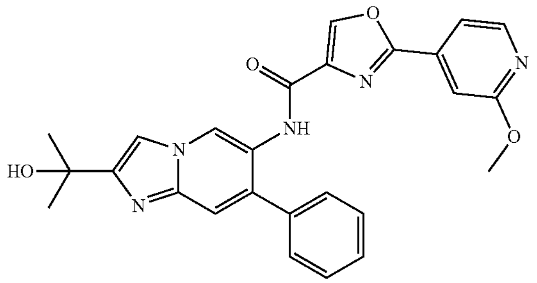
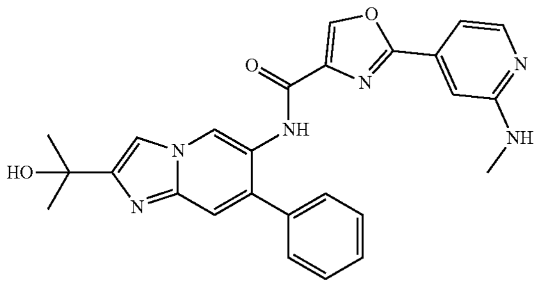
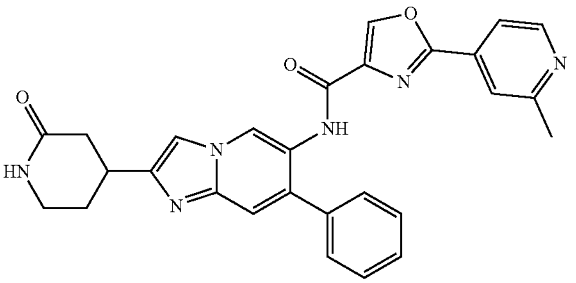
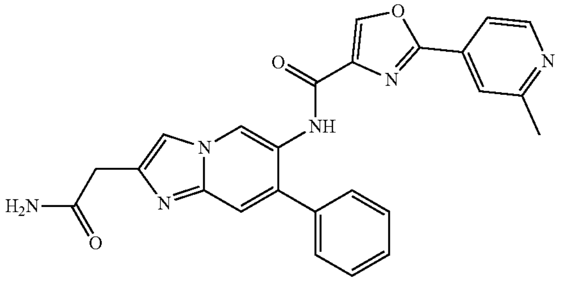

-continued
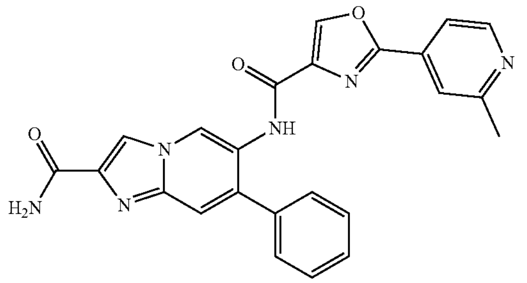
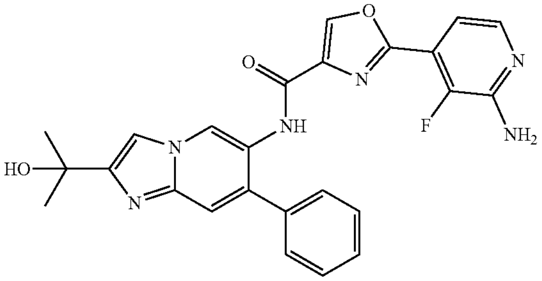
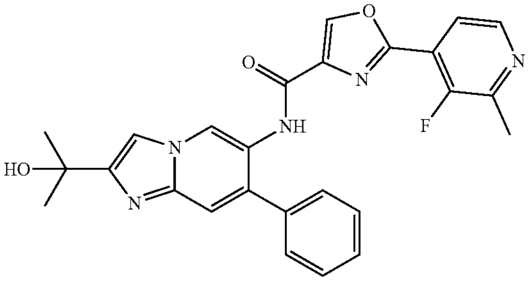
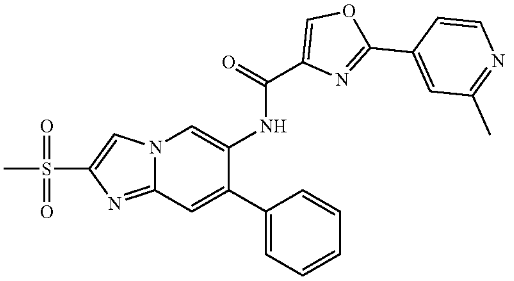
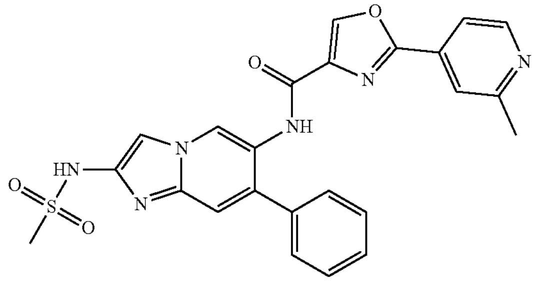
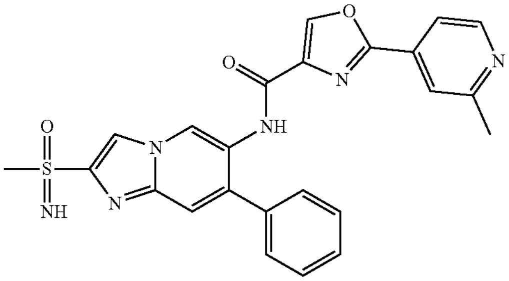
-continued
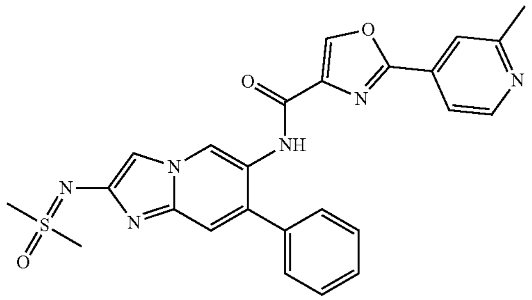
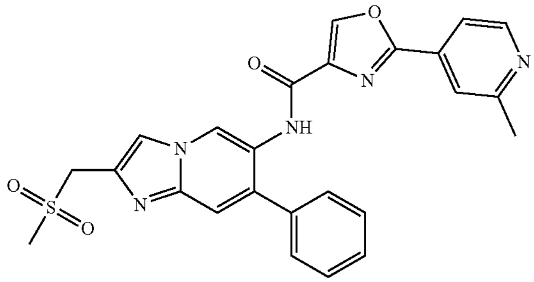
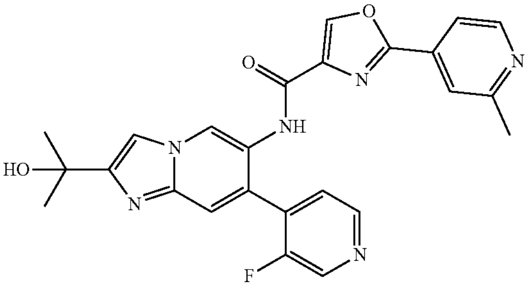
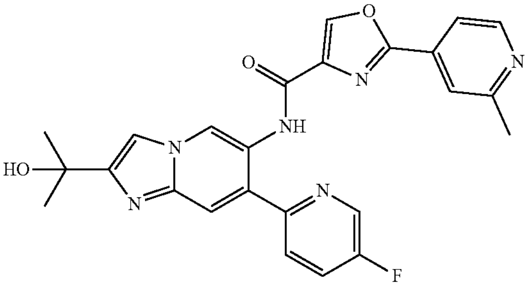
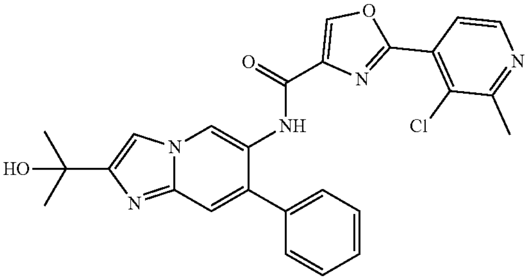
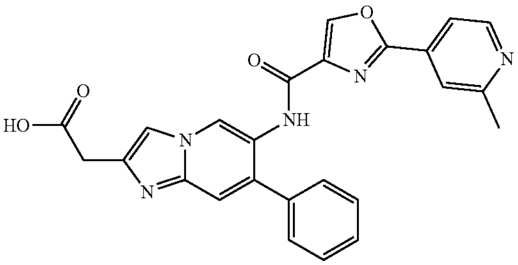 and -continued
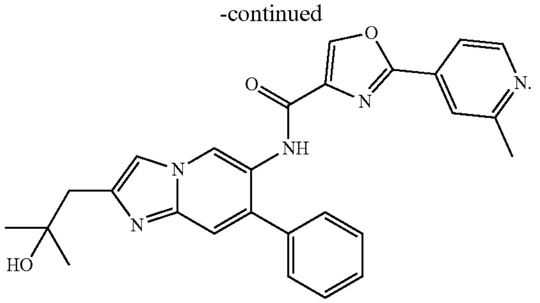
3. A method for treating hematoma in a subject in need thereof, comprising: administering the compound or the pharmaceutically acceptable salt thereof as defined claim 1 to the subject.
4. The method as defined in claim 3, wherein the hematoma is a diffuse large B-cell lymphoma.
* * * * *